(12) United States Patent
De Wever et al.

(10) Patent No.: US 9,279,812 B2
(45) Date of Patent: Mar. 8, 2016

(54) NEUREGULIN-1-BASED PROGNOSIS AND THERAPEUTIC STRATIFICATION OF COLORECTAL CANCER

(75) Inventors: Olivier De Wever, Destelbergen (BE); Astrid De Boeck, Buggenhout (BE)

(73) Assignee: UNIVERSITEIT GENT, Ghent (BE)

( * ) Notice: Subject to any disclaimer, the term of this patent is extended or adjusted under 35 U.S.C. 154(b) by 76 days.

(21) Appl. No.: 14/343,071

(22) PCT Filed: Sep. 12, 2012

(86) PCT No.: PCT/EP2012/067758
§ 371 (c)(1),
(2), (4) Date: Mar. 6, 2014

(87) PCT Pub. No.: WO2013/037789
PCT Pub. Date: Mar. 21, 2013

(65) Prior Publication Data
US 2014/0220597 A1    Aug. 7, 2014

(30) Foreign Application Priority Data
Sep. 12, 2011   (EP) .................................... 11180878

(51) Int. Cl.
*G01N 33/574* (2006.01)
(52) U.S. Cl.
CPC .. *G01N 33/57419* (2013.01); *G01N 2333/4756* (2013.01); *G01N 2800/52* (2013.01)
(58) Field of Classification Search
None
See application file for complete search history.

(56) References Cited

U.S. PATENT DOCUMENTS

2008/0176229 A1 * 7/2008 Agus et al. .................... 435/6

OTHER PUBLICATIONS

Harrison et al. (Biol. Psychiatry, 60: 132-140, 2006).*
Bates et al. (Cancer Biology and Therapy, 4: 365-370, 2005).*
Hardy et al. (J Mammary Gland Biol. Neoplasia, 15: 191-199, Apr. 2010).*
The PCT International Search Report, dated Jan. 16, 2013 in connection with PCT International Patent Application No. PCT/EP2012/067758, 4 pages.
PCT Notification Concerning Transmittal of International Preliminary Report on Patentability dated Aug. 12, 2013 in connection with PCT International Patent Application No. PCT/EP2012/067758, 10 pages.
Depypere, B entitled "De Rol Van Mesenchymale Stromale Cellen Bij Tumorprogressie in Colorectaalkanker," May 6, 2011, retrieved from the Internet: URL:http://lib.ugent.be/fulltxt/RUG01/001/787/901/RUG01-001787901_2012_0001_AC.pdf, 74 pages.
Venkateswarlu, S et al., Entitled "Autocrine heregulin generates growth factor independence and blocks apoptosis in colon cancer cells," Oncogene 2002 21, Jan. 3, 2002, pp. 78-86.
Tatsuguchi A, et al., Entitled "Clinical Significance of Heregulin and Phosphorylated ERBB Receptor Family Expression in Colorectal Cancer," Gastroenterology, May 2011; Digestive Disease Week 2011, vol. 140, NR-5, Suppl. 1, Apr. 11, 2011, p. S340.
Yonezawa M, et al., Entitled "ErbB kinase and heregulin signaling and their role on VEGF secretion in colon cancer cells," Gastroenterology Apr. 2004, Digestive Disease Week/105th Annual Meeting of the American-Gastroenterological-Association, May 16-20, 2004, vol. 126, NR-4, Suppl. 2, Jan. 1, 2004, p. A263.
Kapitanovic S, et al., Entitled "The expression of p185(HER-2/neu) correlates with the stage of disease and survival in colorectal cancer," Gastroenterology, vol. 112, No. 4, Apr. 1, 1997, pp. 1103-1113.
De Boeck A, et al., Entitled "Resident and bone marrow-derived mesenchymal stem cells in head and neck squamous cell carcinoma," Oral Oncology, vol. 46, No. 5, May 1, 2010, pp. 336-342.
De Wever O, et al., Entitled "Modeling and quantification of cancer cell invasion through collagen type 1 matrices," The International Journal of Developmental Biology Spain 2010, vol. 54, No. 5, Jan. 1, 2010, pp. 887-896.
Hannelore D, et al., Entitled "The extracellular matrix regulates cancer progression and therapy response: implications for prognosis and treatment," Current Pharmaceutical Design, vol. 15, No. 12, Jan. 1, 2009, pp. 1373-1384.
Yonezawa M, et al., Entitled "Heregulin-Induced VEGF Expression via the ErbB3 Signaling Pathway in Colon Cancer," Digestion, vol. 80, No. 4, Jan. 1, 2009, pp. 215-225.

* cited by examiner

*Primary Examiner* — Brad Duffy
*Assistant Examiner* — Nelson B Moseley, II
(74) *Attorney, Agent, or Firm* — Amster, Rothstein & Ebenstein LLP

(57) ABSTRACT

The present invention relates to the prognosis, therapeutic stratification and treatment of colorectal cancer. More in particular, the present invention discloses that significantly increased levels of transmembrane type 1 neuregulin-1 in tumor-associated mesenchymal cells present in a sample of a patient indicate that the patient has a worse prognosis when compared to patients having low levels of transmembrane type 1 neuregulin-1 in tumor-associated mesenchymal cells. Moreover, the present invention relates to the usage of transmembrane type 1 neuregulin-1 expression in tumor-associated mesenchymal cells to predict resistance to HER1 inhibitors during colorectal cancer therapy and/or to predict whether a patient would benefit from a therapy based on the prevention of neuregulin-1 and/or HER3 activity.

8 Claims, 36 Drawing Sheets

| Condition | Animals inoculated | Animals presenting tumors | Tumor take rate (%) |
|---|---|---|---|
| HCT-8/E11 | 10 | 2 | 20 |
| HCT-8/E11 + BM-MSC | 10 | 10 | 100 |
| HCT-8/E11 CM$^{BM-MSC}$ | 10 | 6 | 60 |
| HCT116 | 10 | 10 | 100 |
| HCT 116 + BM-MSC | 10 | 10 | 100 |
| SW480 | 10 | 2 | 20 |
| SW480 + BM-MSC | 10 | 10 | 100 |
| BM-MSC | 10 | 0 | 0 |

Figure 4 B
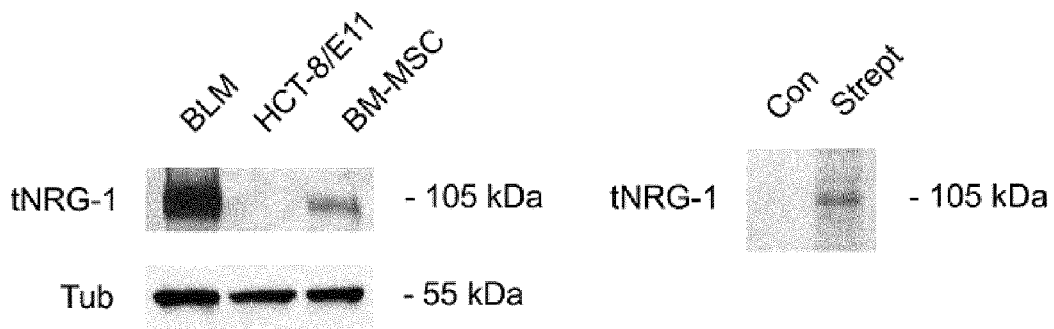
Figure 4 C
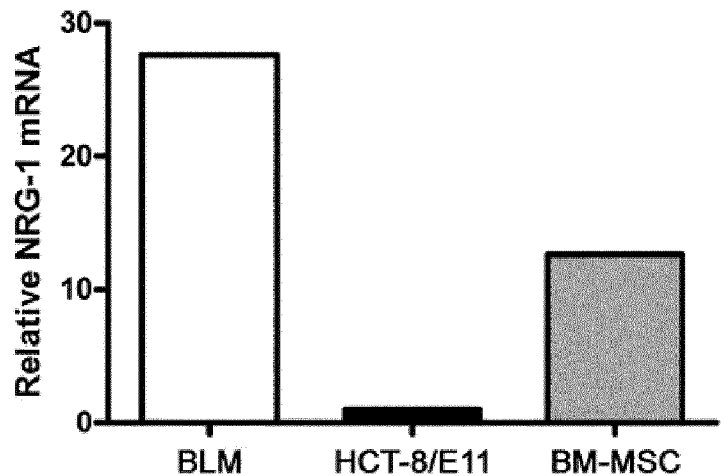
Figure 4 D
| Peptide | Pept Hits (exp1) | Pept Hits (exp2) | Domain |
|---|---|---|---|
| ASLADSGEYMCK | 3 | 2 | Ig-like |
| CETSSEYSSLR | 3 | 4 | Ig-like |
| LVLRCETSSEYSSLR | / | 1 | Ig-like |
| TFCVNGGECFMVK | 3 | 1 | EGFc |

|  | Stromal tNRG-1 expression | | |
|---|---|---|---|
|  | Low | High | *P*-value |
| Primary tumor | 13 | 41 | .006 |
| Adjacent normal | 4 | 0 |  |
| Invasion depth | *n* = 13 | *n* = 33 |  |
| Submucosa (T$_1$) | 1 | 1 | .04 |
| Muscularis propria (T$_2$) | 5 | 4 |  |
| Subserosa (T$_3$) | 6 | 21 |  |
| Visceral peritoneum (T$_4$) | 1 | 7 |  |
| UICC stage | *n* = 13 | *n* = 41 |  |
| I | 6 | 4 | .005 |
| II | 3 | 12 |  |
| III | 4 | 17 |  |
| IV | 0 | 8 |  |
| 5-year PFS | 8/10 (80%) | 6/28 (21%) | .002 |

NEUREGULIN-1-BASED PROGNOSIS AND THERAPEUTIC STRATIFICATION OF COLORECTAL CANCER

CROSS-REFERENCE TO RELATED APPLICATIONS

This application is a U.S. national stage entry under 35 U.S.C. §371 of PCT International Patent Application No. PCT/EP2012/67758, filed Sep. 12, 2012, which claims priority to European Patent Application No. 11180878.8, filed Sep. 12, 2011, the contents of which are incorporated herein by reference in their entirety.

TECHNICAL FIELD OF INVENTION

The present invention relates to the prognosis and/or therapeutic stratification of colorectal cancer. More in particular, the present invention discloses that significantly increased levels of transmembrane type 1 neuregulin-1 in tumor-associated mesenchymal cells present in a sample of a patient are associated with a worse prognosis when compared to patients having low levels of transmembrane type 1 neuregulin-1 in tumor-associated mesenchymal cells. Moreover, the present invention relates to the usage of transmembrane type 1 neuregulin-1 expression in tumor-associated mesenchymal stem cells to predict resistance to HER1 inhibitors during colorectal cancer therapy and/or to predict whether a patient would benefit from a therapy based on the prevention of neuregulin-1 and/or HER3 activity.

BACKGROUND ART

Colorectal cancer (CRC) is the third most common cancer in both men and women and accounts for 9% of all new cancer cases and cancer deaths in the United States (1). Upon diagnosis, 19% of CRC cases are metastatic and while the overall 5-year survival rate for patients with CRC is 65%, in metastatic disease it is only 12% (1). Emerging evidence demonstrates that tumor progression involves complex heterotypic multicellular interactions between cancer cells and tumor-associated mesenchymal cells (2). CRC is often accompanied by a well-orchestrated desmoplastic reaction, which involves the distant recruitment of bone marrow-derived mesenchymal stem cells (BM-MSC) in growing tumors. BM-MSC have the potential to differentiate into multiple cell lineages such as osteoblasts, chondrocytes and adipocytes (3). Mouse models reveal that BM-MSC migrate to colon tumor xenografts (4, 5) and are precursors of tumor-associated mesenchymal cells (6-8), which in turn stimulate cancer progression (9, 10). The tropism of MSC for tumors is thought to recapitulate their migration into wounds during wound healing and tissue repair (11, 12).

The human epidermal growth factor receptor (HER/ErbB) tyrosine kinases (RTKs) and their ligands are involved in cancer cell proliferation, survival, motility, invasion and metastasis. The following four HER receptors have been described in mammals: HER1 (ErbB1 or epidermal growth factor receptor [EGFR], HER2 [ErbB2 or neu], HER3 [ErbB3], and HER4 [ErbB4]). Activation of these receptors can occur by the following three different mechanisms: interaction with specific HER ligands, overexpression of the receptor, and molecular alterations such as point mutations or truncations. It is through dimerization and transphosphorylation that HER receptors perform their signaling functions. About 80% of all CRCs exhibit HER1 expression or overexpression correlating with increased metastasis and reduced patient's survival (13, 14). It has been indicated that HER3 expression is involved in CRC progression and that its phosphorylation is of prognostic value (15-17).

The neuregulin (NRG) family of growth factors comprises numerous heparin-binding glycoproteins that arise via alternative splicing off four distinct genes (NRG-1, NRG-2, NRG-3, and NRG-4). NRG-1 and NRG-2 are the most closely related: both interact with HER3. NRG-1 has a high binding affinity for HER3 and preferentially acts through HER2-dependent recruitment of PI3K (18-20). Alternative splicing and regulation through multiple promoters produce at least 15 different NRG-1 isoforms; most are synthesized as transmembrane precursors and released as soluble factors by action of cell surface proteases, such as tumor necrosis factor-alpha converting enzyme (TACE) (21, 22). NRGs are produced by epithelial cells in melanoma, breast and ovarian tumors (23, 24), but also by tumor-associated mesenchymal cells in gastric and breast tumors (25-27). US 2007/0275404 and Eschrich et al. (28) disclose that expression of the NRG-2 gene might be used as a prognostic marker for breast and colorectal cancer, respectively.

Yoshioka et al. (29) further disclose that NRG-1 (heregulin) might participate in a highly liver metastatic phenotype of a human colon cancer cell line via HER2/HER3 signalling. Liles et al. (30) disclose that fibroblast-derived NRG-1 promote proliferation of a pancreatic cancer cell line via phosphorylation of HER3 and that said proliferation can be best disrupted through combined HER1 (EGFR)-HER3(erbB3) inhibition. Venkateswarlu et al. (Oncogene 2002: 78-86) disclose that autocrine heregulin is responsible for cell cycle re-entry of colon cancer cells and that heregulin neutralizing antibody treatment generates apoptosis of the latter cells. Tatsuguchi et al. (Gastroenterology 2011, vol 140 N° 5 suppl 1: S340) further disclose that significantly higher expression levels of heregulin are found in CRC tissue samples (i.e. predominantly in the cytoplasm of cancer cells) compared to normal tissue counterparts and concludes that heregulin may be a useful marker of prognostic significance in CRC patients. Yonezawa et al. (Gastroenterology 2004, vol 126 N° 4 suppl 2: A263) disclose that heregulin overexpression was immunohistochemically observed in cancer cells and mesenchymal cells and that heregulin might regulate VEGF secretion through autocrine and paracrine mechanisms. However, no correlation has been described or suggested between high expression of transmembrane heregulin in solely mesenchymal cells and a worse prognosis.

About 19% of CRC patients present initially with metastatic disease and the standard chemotherapy regimen for these patients are the chemotherapeutic agents 5-fluorouracil, irinotecan, and oxaliplatin, often in combination with the monoclonal antibodies cetuximab or panitumumab (31, 32) (NCCN Clinical Practice Guidelines in Oncology. Colon Cancer. Version 3.2011). Cetuximab and panitumumab bind to HER1 (EGFR) on cancer cells, thereby blocking the downstream intracellular signaling pathways. One member of this cascade is KRAS, and over the recent years increasing evidence suggested that patients with KRAS mutations do not benefit from the addition of cetuximab or panitumumab to standard chemotherapy (33). KRAS mutations are found in approximately 40-60% of all CRC specimens. As a consequence, KRAS testing is mandatory for patients with metastatic CRC before receiving cetuximab or panitumumab (33).

Pertuzumab is a recombinant, humanized mAb that specifically binds HER2 (34) and prevents HER2 homo- and HER2/HER3 heterodimerisation (35). Because of this mechanism of action, pertuzumab antitumor activity is not restricted to tumors with HER2 overexpression and therefore differs from the therapeutic monoclonal antibody trastuzumab, which binds to a non-overlapping juxtamembrane region of HER2's extracellular domain and cannot inhibit HER2/HER3 heterodimerisation. In addition, a phase I/II clinical trial is currently ongoing in Canada and the United States to study the effectiveness of pertuzumab combined with cetuximab in patients with locally advanced or metastatic CRC who did not respond to cetuximab (36).

The present invention discloses that increased levels of transmembrane type 1 neuregulin-1 in tumor-associated mesenchymal cells in a sample of human colorectal cancer patients surprisingly and significantly correlate with a worse prognosis of said patients in terms of tumor stage, invasion depth and 5-year progression-free survival. The latter prognosis further indicates that these patients would benefit from a therapy based on the prevention of neuregulin-1 and/or HER3 activity. The latter prognosis is thus valuable to fine tune therapy of colorectal cancer by predicting whether a patient would benefit from a combined treatment of—for example—pertuzumab with cetuximab and/or whether a patient has resistance to HER1 inhibitors such as cetuximab.

DESCRIPTION OF THE INVENTION

Figure 1:
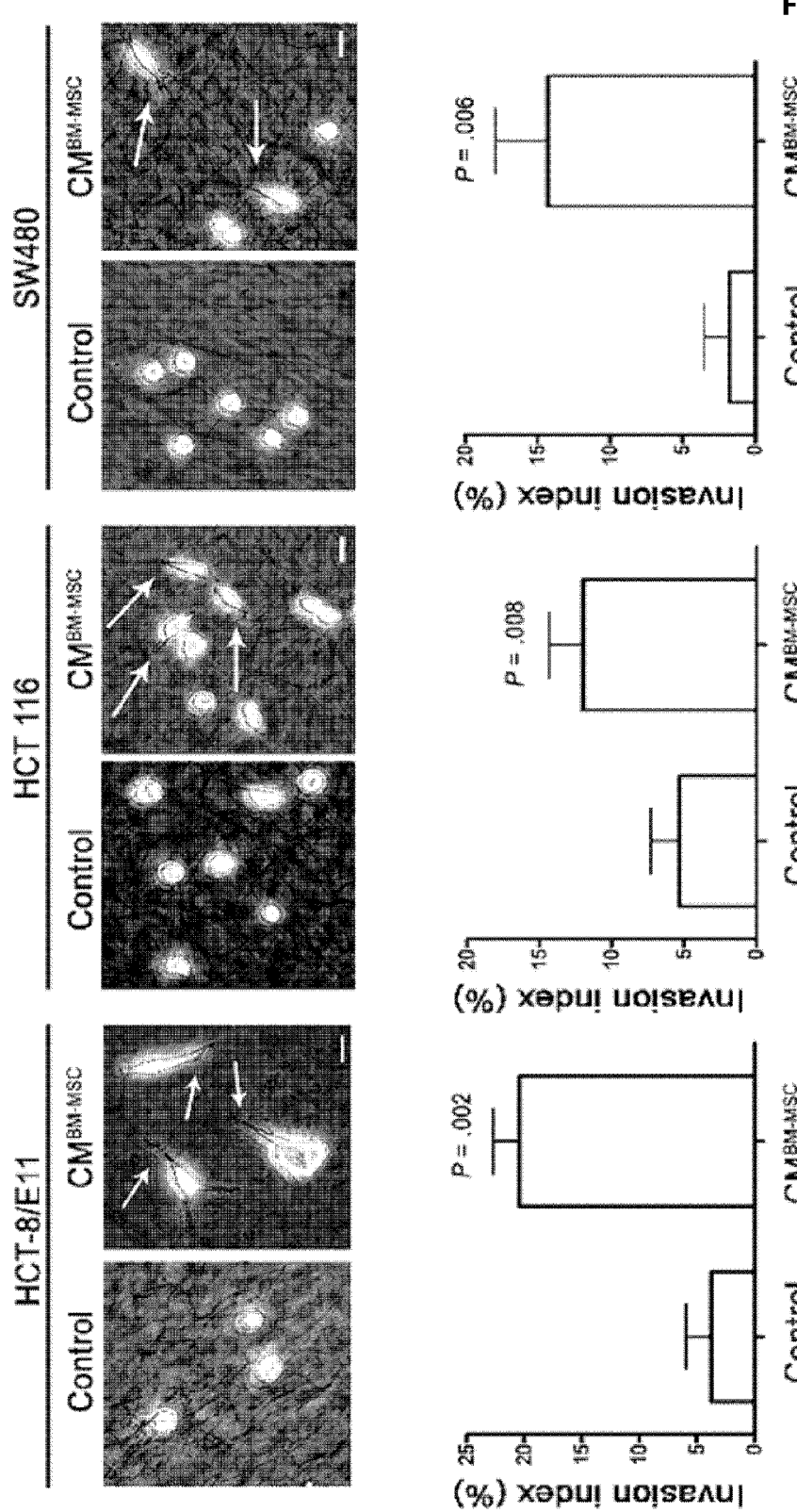
FIG. 1. Effect of BM-MSC on morphology and matrix invasion of cultured CRC cells. (A) Phase-contrast images showing morphology of single HCT-8/E11, HCT 116 and SW480 CRC cells on collagen type I after treatment with $CM^{BM-MSC}$ for 24 hours. Arrows indicate invasive extensions. Scale bar, 20 µm (upper panel). Quantification of collagen invasion by calculating the invasion index which is the ratio of the number of cells containing invasive extensions over the total number of cells counted in each field, for a total of 10 fields. Results are expressed as mean and standard error from three independent experiments. P values were calculated using chi-square test; statistically significant P values are indicated (lower panel). (B) Laser scanning confocal images of representative phalloidin-Alexa Fluor 594 stained HCT-8/E11 cells on collagen type I after treatment with $CM^{BM-MSC}$ for 24 hours. Scale bar, 20 µm (upper panel). Box and whisker plot showing quantification of the morphology with the factor shape from 25 HCT-8/E11 cells for each condition. Median, quartiles and highest and lowest values are indicated on box and whisker plots. Factor shape was calculated as $(perimeter)^2/(4\pi area)$. P values were calculated using Mann-Whitney test; statistically significant P values are indicated (lower panel). (C) Combined bright-field and GFP-fluorescence images of a representative HCT-8/E11-GFP spheroid followed at different time intervals under control and BM-MSC co-culture conditions. Scale bar, 300 µm. (D and E) Image J-assisted calculation of the factor shape (ratio of $perimeter^2/4\pi$ to area) (D, left panel) and area (E, left panel) from HCT-8/E11-GFP spheroids followed at different time intervals under control and BM-MSC co-culture conditions. Results are expressed as mean and standard error from 6 spheroids from three independent experiments. P values were calculated using two-way repeated measures ANOVA test; statistically significant P values are indicated. Confocal images of a typical invasion front from a phalloidin-Alexa Fluor 594 stained HCT-8/E11-GFP spheroid cultured for 96 hours under control or BM-MSC co-culture conditions. Scale bar, 50 µm; inset shows whole spheroid, scale bar, 300 µm (D, right panel). Paraffin-embedded sections of HCT-8/E11-GFP spheroids cultured for 96 hours under control or BM-MSC co-culture conditions were immunostained for the proliferation marker Ki67. The mean number of proliferating cells and standard error calculated from 12 images of three spheroids per condition is indicated. Scale bar, 100 µm; inset scale bar, 50 µm (E, right panel).
Figure 1:
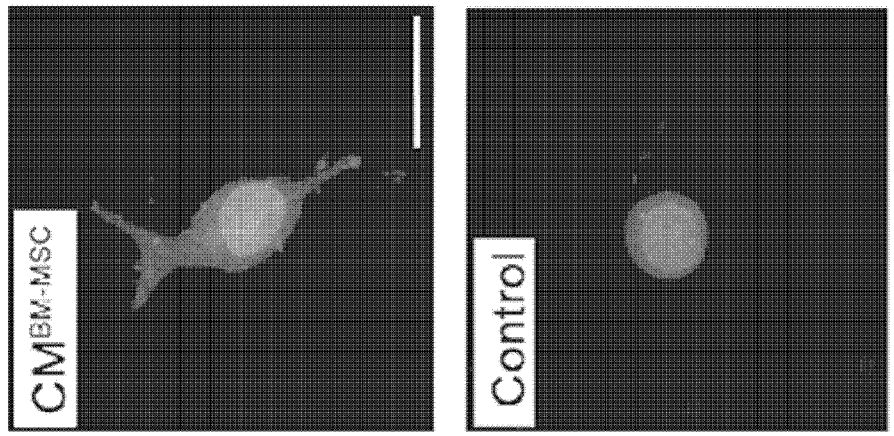
Figure 1:
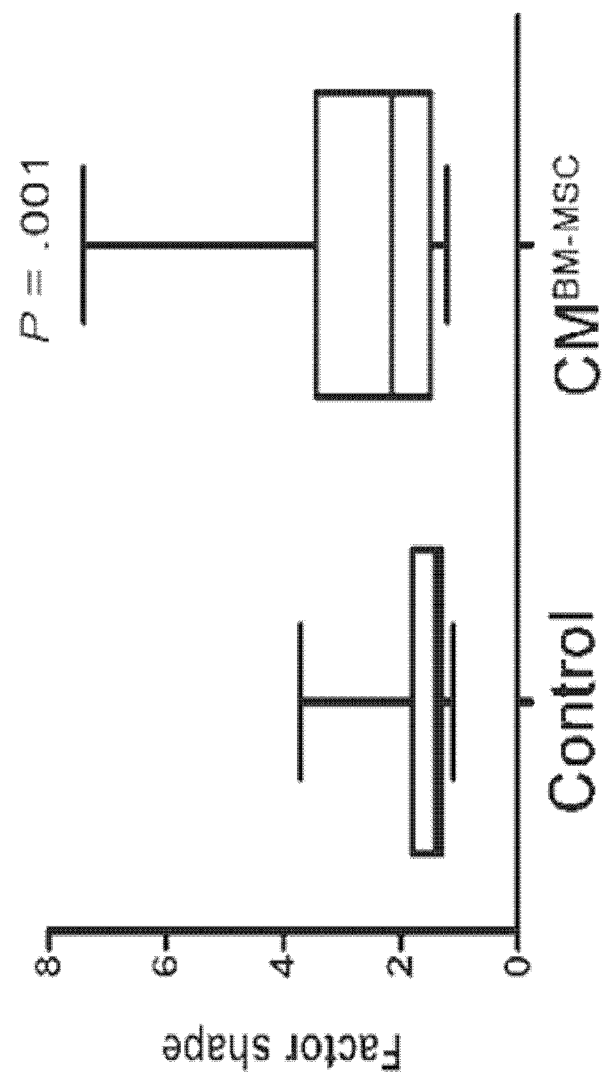
Figure 1:
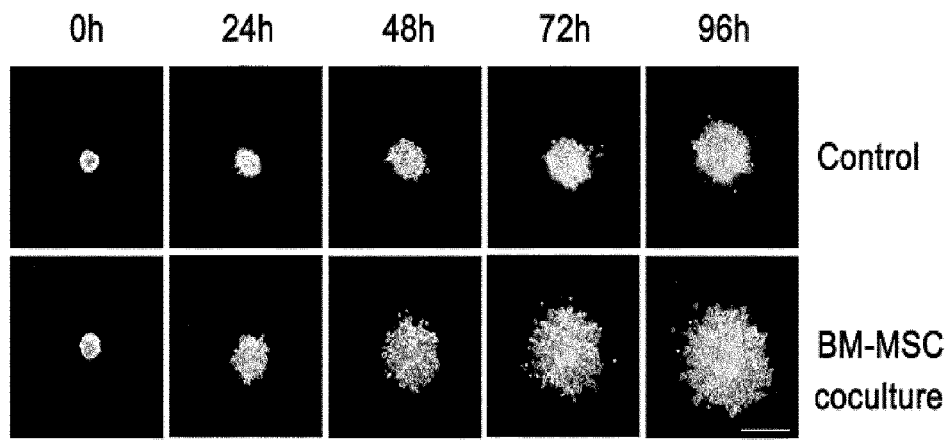
Figure 1:
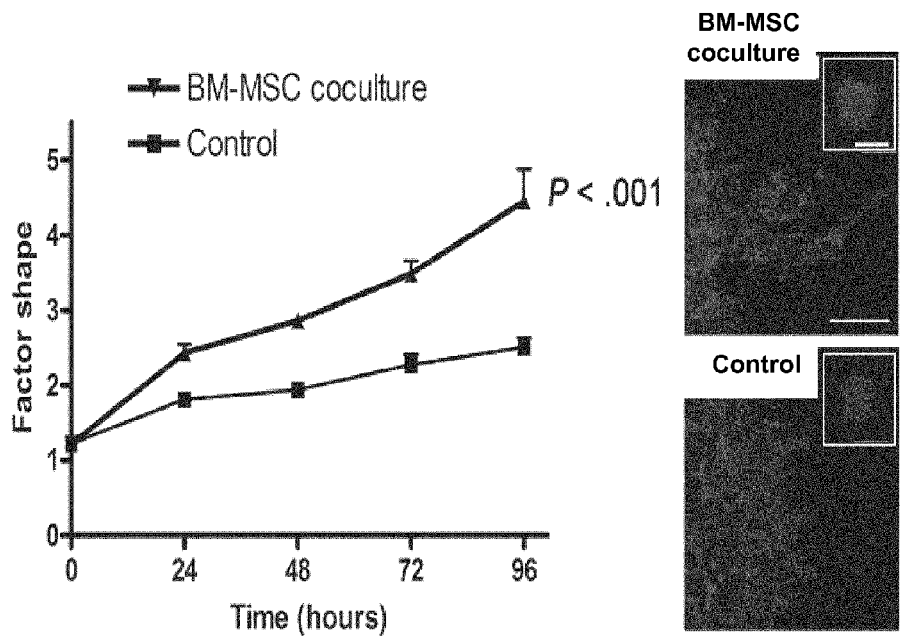
Figure 1:
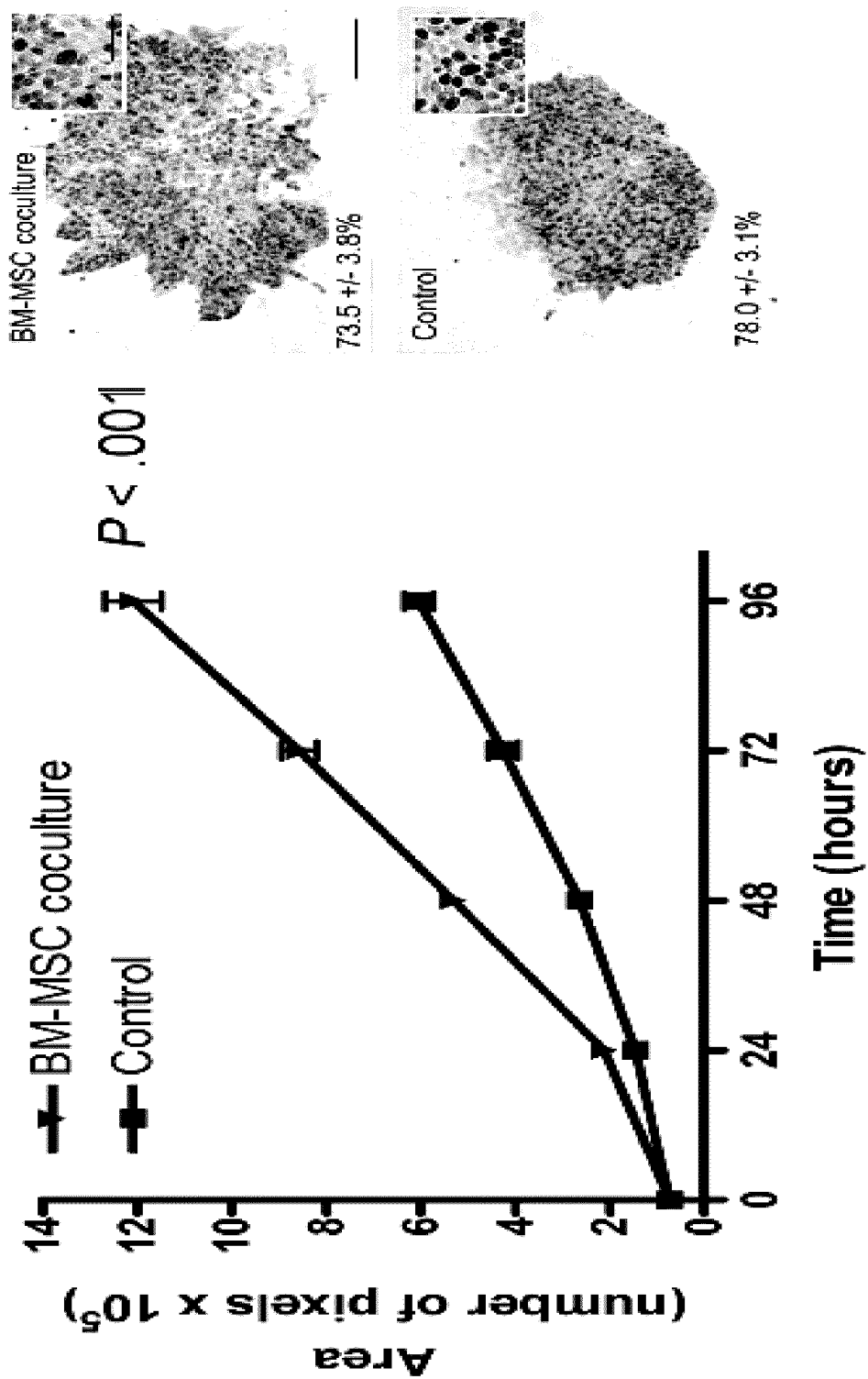

The present invention discloses that significantly increased levels of transmembrane type 1 neuregulin-1 in tumor-associated mesenchymal cells (also denominated as tumor-associated fibroblasts which are characterized by the expression of α-smooth muscle actin (α-SMA)) present in a sample of human colorectal cancer patients significantly correlate with a worse prognosis in terms of tumor stage, invasion depth and 5-year progression-free survival. Therefore, the present invention relates to an in vitro method for the prognosis of colorectal cancer in a test subject comprising:
  measuring the level of transmembrane type 1 neuregulin-1 in tumor-associated mesenchymal cells present in a biological sample taken from said test subject, and
  comparing said level of transmembrane type 1 neuregulin-1 with a reference level of transmembrane type 1 neuregulin-1 obtained from a sample of healthy tissue of a subject, wherein
  a significantly increased level of transmembrane type 1 neuregulin-1 in tumor-associated mesenchymal cells present in a sample of the test subject as compared to that of said healthy tissue indicates that the test subject has a worse prognosis.

In other words, the present invention relates to the usage of transmembrane type 1 neuregulin-1 present in tumor-associated mesenchymal cells as a biomarker to evaluate the prognosis of a patient with colorectal cancer in vitro. More particularly, the present invention relates to the use of transmembrane type 1 neuregulin-1 in tumor-associated mesenchymal cells as a biomarker to evaluate the prognosis of a patient with colorectal cancer in vitro, wherein a significantly increased level of transmembrane type 1 neuregulin-1 in tumor-associated mesenchymal cells present in a biological sample taken from the patient compared to that of a reference level of transmembrane type 1 neuregulin-1 obtained from a sample of healthy tissue of a subject indicates that the patient has a worse prognosis.

With the term 'biomarker' is meant a characteristic that is objectively measured and evaluated as an indicator of normal biologic processes, pathogenic processes, or pharmacologic responses to a therapeutic intervention. Hence, the biomarker transmembrane type 1 neuregulin-1, more particularly transmembrane type 1 neuregulin-1 in tumor-associated mesenchymal cells, can be used, among other uses, to: 1) diagnose colorectal cancer with the potential to metastasize, to invade deeply into surrounding tissues and/or to result in a poor 5-year progression-free survival; 2) evaluate the prognosis of said colorectal cancer which encompasses predictions about the likely course of disease or disease progression, particularly with respect to the likelihood of metastasis, disease remission, disease relapse, tumor recurrence and death; 3) therapeutically stratify patients with colorectal cancer in order to decide which therapy, such as a therapy based on the prevention of neuregulin-1 and/or HER3 activity, should be given to said patient and/or to determine which patients are resistant to a certain therapy such as therapy with cetuximab based on the prevention of HER1 activity; and 4) monitor disease progression once a particular therapy has been administered to said patients.

The latter prognosis thus indicates that these patients would benefit from a therapy based on the prevention of neuregulin-1 and/or HER3 activity. The latter prognosis is thus valuable to fine tune therapy of colorectal cancer by predicting whether a patient would benefit from a combined treatment of—for example—pertuzumab with cetuximab. Cetuximab and panitumumab bind to HER1 whereas pertuzumab inhibits HER2/HER3 dimerization and thus prevents the tyrosine kinase activity of HER3. A patient which resists therapy with HER 1 inhibitors might thus benefit from a treatment with HER 3 inhibitors or from a combined treatment with both HER 1 and HER3 inhibitors. The present invention thus relates to the prediction of resistance to a therapy based on the prevention of HER1 activity.

The present invention thus particularly relates to an in vitro method as indicated above wherein said prognosis incorporates the decision or determination whether a patient having colorectal cancer would benefit from a therapy based on the prevention of the activity of neuregulin-1 and/or the tyrosine kinase activity of HER3, and wherein said significantly increased level of transmembrane type 1 neuregulin-1 in tumor-associated mesenchymal cells present in a sample of the patient as compared to that of said healthy tissue indicates that said patient would benefit from a therapy based on the prevention of the activity of neuregulin-1 and/or the tyrosine kinase activity of HER3. Accordingly, also disclosed herein is the use of transmembrane type 1 neuregulin-1 present in tumor-associated mesenchymal cells, to determine whether a patient having colorectal cancer would benefit from a therapy based on the prevention of the activity of neuregulin-1 and/or the tyrosine kinase activity of HER3. More particularly, the present invention also relates to the use of transmembrane type 1 neuregulin-1 in tumor-associated mesenchymal cells to determine whether a patient having colorectal cancer would benefit from a therapy based on the prevention of the activity of neuregulin-1 and/or the tyrosine kinase activity of HER3, wherein a significantly increased level of transmembrane type I neuregulin-1 in tumor-associated mesenchymal cells present in a biological sample taken from the patient compared to that of a reference level of transmembrane type 1 neuregulin-1 obtained from a sample of healthy tissue of a subject indicates that the patient would benefit from a therapy based on the prevention of the activity of neuregulin-1 and/or the tyrosine kinase activity of HER3.

Also disclosed herein is a method to determine whether a patient having colorectal cancer would benefit from a therapy based on the prevention of the activity of neuregulin-1 and/or the tyrosine kinase activity of HER3 comprising:
measuring the level of transmembrane type 1 neuregulin-1 in tumor-associated mesenchymal cells present in a biological sample taken from said patient, and
comparing said level of transmembrane type 1 neuregulin-1 with a reference level of transmembrane type 1 neuregulin-1 obtained from a sample of healthy tissue of a subject, wherein
a significantly increased level of transmembrane type I neuregulin-1 in tumor-associated mesenchymal cells present in a sample of the patient as compared to that of said healthy tissue indicates that the patient would benefit from a therapy based on the prevention of the activity of neuregulin-1 and/or the tyrosine kinase activity of HER3.

Also disclosed herein is a method for treating colorectal cancer in a patient comprising preventing the activity of neuregulin-1 and/or the tyrosine kinase activity of HER3, wherein said patient has significantly increased levels of transmembrane type 1 neuregulin-1 in tumor-associated mesenchymal cells present in a biological sample taken from the patient as compared to a reference level of transmembrane type 1 neuregulin-1 obtained from a sample of healthy tissue of a subject.

Also disclosed herein is the use of inhibitors of neuregulin-1 activity and/or inhibitors of HER3 tyrosine kinase activity for the preparation of a medicament for treating colorectal cancer in a patient, wherein said patient has significantly increased levels of transmembrane type 1 neuregulin-1 in tumor-associated mesenchymal cells present in a biological sample taken from the patient as compared to a reference level of transmembrane type 1 neuregulin-1 obtained from a sample of healthy tissue of a subject.

Also disclosed herein are inhibitors of neuregulin-1 activity and/or inhibitors of HER3 tyrosine kinase activity for use in treating colorectal cancer in a patient, wherein said patient has significantly increased levels of transmembrane type 1 neuregulin-1 in tumor-associated mesenchymal cells present in a biological sample taken from the patient as compared to a reference level of transmembrane type 1 neuregulin-1 obtained from a sample of healthy tissue of a subject.

The present invention thus also relates to an in vitro method as indicated above wherein said prognosis incorporates the decision or determination whether a patient having colorectal cancer has or developed resistance to a therapy based on the prevention of HER1 activity, and wherein said significantly increased level of transmembrane type 1 neuregulin-1 in tumor-associated mesenchymal cells present in a sample of the patient as compared to that of said healthy tissue indicates that said patient has resistance to a therapy based on the prevention of the tyrosine kinase activity of HER1. Accordingly, also disclosed herein, is the use of transmembrane type 1 neuregulin-1 in tumor-associated mesenchymal cells to predict resistance to a therapy based on the prevention of HER1 activity in a patient having colorectal cancer in vitro. More particularly, the invention also relates to the use of transmembrane type 1 neuregulin-1 in tumor-associated mesenchymal cells to predict resistance to a therapy based on the prevention of HER1 activity in a patient having colorectal cancer in vitro, wherein a significantly increased level of transmembrane type I neuregulin-1 in tumor-associated mesenchymal cells present in a biological sample taken from the patient compared to that of a reference level of transmembrane type 1 neuregulin-1 obtained from a sample of healthy tissue of a subject would indicate that the patient has resistance to a therapy based on the prevention of HER1 activity.

Also disclosed herein is a method to predict resistance to a therapy based on the prevention of HER1 activity in a patient having colorectal cancer comprising:
measuring the level of transmembrane type 1 neuregulin-1 in tumor-associated mesenchymal cells present in a biological sample taken from said patient, and
comparing said level of transmembrane type 1 neuregulin-1 with a reference level of transmembrane type 1 neuregulin-1 obtained from a sample of healthy tissue of a subject, wherein
a significantly increased level of transmembrane type I neuregulin-1 in tumor-associated mesenchymal cells present in a sample of the patient as compared to that of said healthy tissue indicates that the patient has resistance to a therapy based on the prevention of HER1 activity.

The term 'a biological sample' relates to a primary tumor sample (also denominated as colorectal cancer tissue or biopsy), circulating mesenchymal precursor cells or a biofluid such as blood, serum, plasma lymph, urine, saliva or any other bodily secretion or derivative thereof. Methods for collecting various samples are well known in the art. The present invention specifically relates to an in vitro method as indicated above wherein said biological sample is colorectal cancer tissue taken from said test subject or said patient having colorectal cancer.

The term 'neuregulin-1' relates to type I neuregulin-1, also known as heregulin, with at least 7 different isoforms as a result of alternative splicing (37, 38).

It should be noted that neuregulin-1 protein can be detected intracellularly (often as part of a membrane and more particularly as a transmembrane protein), or, extracellularly as a secreted (soluble) form. The latter soluble form might correspond to the extracellular part of the transmembrane protein which is cleaved of by a protease such as the tumor necrosis factor converting enzyme (TACE).

The term 'transmembrane type 1 neuregulin-1 (tNRG-1)' or 'type 1 neuregulin-1 precursor' relates to the type 1 neuregulin-1 protein that can be detected intracellularly, in particular as part of a membrane and more particularly as a transmembrane protein.

As indicated above, the present invention relates to an in vitro method wherein said transmembrane type 1 neuregulin-1 is measured in tumor-associated mesenchymal cells present in a biological sample of a test subject or a patient having colorectal cancer.

The term 'tumor-associated mesenchymal cells (T-MC)' or 'tumor-associated fibroblasts' or 'myofibroblasts' refer to spindle-shaped mesenchymal cells that may be present around the neoplastic tubules or glands. They can be characterized by the expression of α-smooth muscle actin (α-SMA). They are bone-marrow derived or can be recruited from other compartments and tissues within the human body.

The terms 'increased level of transmembrane type 1 neuregulin-1 in tumor-associated mesenchymal cells present in a sample of the test subject as compared to that of said healthy tissue' depends on which level of transmembrane type 1 neuregulin-1 is measured and how this level is measured. The term 'reference level of transmembrane type 1 neuregulin-1 obtained from a sample of healthy tissue of a subject' may refer to the level of transmembrane type 1 neuregulin-1 that is measured in said sample of healthy tissue of a subject.

With 'healthy tissue' is meant a 'control sample' or 'a similar biological sample as indicated above taken from a healthy patient or healthy tissue, such as healthy tissue taken from the test subject or the patient having colorectal cancer'.

The level of transmembrane type 1 neuregulin-1 may be determined by measuring the expression of transmembrane type 1 neuregulin-1 protein or nucleic acids such as mRNA expression of neuregulin-1. Measuring proteins and nucleic acid levels (such as mRNA levels) are well known in the art and can be undertaken by any method known in the art including but not limited to Western blots, Northern blots, Southern blots, ELISA, immunoprecipitation, immunofluorescence, flow cytometry, immunohistochemistry, nucleic acid hybridization techniques, nucleic acid reverse transcription methods, and nucleic acid amplification methods such as qPCR. The latter techniques are, for example, described in detail in US 2007/0218512. In particular embodiments, expression of a biomarker is detected on a protein level using antibodies that are directed against specific biomarker proteins. These antibodies can be used in various methods such as Western blot, ELISA, immunoprecipitation or immunohistochemistry.

Likewise, immunostaining of tumor tissue can be combined with assessment of clinical information, conventional prognostic methods, and expression of other molecular markers known in the art.

The present invention relates in particular to an in vitro method as indicated above wherein said transmembrane type 1 neuregulin-1 in tumor-associated mesenchymal cells is measured by immunohistochemistry on frozen samples. The present invention particularly discloses that significantly increased levels of transmembrane type 1 neuregulin-1 are found in tumor-associated mesenchymal cells in frozen samples from cancer patients having a worse prognosis when compared to transmembrane type 1 neuregulin-1 expression in frozen samples from healthy patients or healthy tissue. Antibodies which are particularly useful and validated for their specificity in immunohistochemistry on frozen samples as described above are rabbit polyclonal anti-tNRG1 obtainable from Santa Cruz Biotechnology, CA or Atlas Antibodies AB, Stockholm, Sweden.

The present invention further specifically concerns an in vitro method as indicated above wherein said level of transmembrane type 1 neuregulin-1 in tumor-associated mesenchymal cells is significantly increased when more than 25% of said tumor-associated mesenchymal cells within said sample contain transmembrane type 1 neuregulin-1 staining. The term 'more than 25%' indicates that 25, 26, 27, 28, 29, 30, 35, 40, 45, 50, 55, 60, 65, 70, 75, 80, 85, 90, 95 or 100% of said tumor-associated mesenchymal cells contain a clearly visible and specific staining for transmembrane type 1 neuregulin-1.

The term 'worse prognosis' indicates that a patient has a significantly increased chance to belong to the higher cancer stages according to the Union for International Cancer Control (Table 1), and/or, has a significantly increased chance to have an increased invasion depth of the tumor, and/or, has a significantly increased chance to have a decreased progression-free survival.

TABLE 1

TNM staging system for colorectal cancer (adapted from (39)).

| | Primary tumor (T) |
|---|---|
| $T_x$ | Primary tumor cannot be assessed |
| $T_{is}$ | Carcinoma in situ |
| $T_1$ | Tumor invades submucosa |
| $T_2$ | Tumor invades muscularis propria |
| $T_3$ | Tumor invades through the muscularis propria into the subserosa |
| $T_4$ | Tumor directly invades other organs or structures, or perforates visceral peritoneum |

| | Regional lymph nodes (N) |
|---|---|
| $N_x$ | Regional lymph nodes cannot be assessed |
| $N_0$ | No regional lymph node metastases |
| $N_1$ | Metastases in 1-3 regional lymph nodes |
| $N_2$ | Metastases in ≥4 regional lymph nodes |

| | Distant metastases (M) |
|---|---|
| $M_x$ | Presence or absence of distant metastases cannot be determined |
| $M_0$ | No distant metastases detected |
| $M_1$ | Distant metastases detected |

| Stage grouping and 5-year survival | | |
|---|---|---|
| Stage | TNM classification | 5-year survival |
| I | $T_{1-2}, N_0, M_0$ | >90% |
| IIA | $T_3, N_0, M_0$ | 80%-85% |
| IIB | $T_4, N_0, M_0$ | 70%-80% |
| IIIA | $T_{1-2}, N_1, M_0$ | 65%-80% |
| IIIB | $T_{3-4}, N_1, M_0$ | 50%-65% |

TABLE 1-continued

TNM staging system for colorectal cancer (adapted from (39)).

| IIIC | $T_{1-4}$, $N_2$, $M_0$ | 25%-50% |
| IV | $T_{1-4}$, $N_{0-2}$, $M_1$ | 5%-8% |

The present invention thus relates to an in vitro method as indicated above wherein said worse prognosis corresponds to having a significantly increased chance to belong to the higher cancer stages according to the Union for International Cancer Control, and/or, to having a significantly increased chance to have an increased invasion depth of the tumor, and/or, to have a significantly increased chance to have a decreased progression-free survival.

A kit comprising reagents to perform an assay for measuring transmembrane type 1 neuregulin-1 levels in tumor-associated mesenchymal cells in a sample from a patient having colorectal cancer is thus useful to perform the present invention. The latter assay can be a neuregulin-1 immunohistochemistry assay or Quantitative RT-PCR assay on biopsies, primary cancer samples or circulating mesenchymal precursor cells of said patient, or, a sandwich-type ELISA on biofluids of said patient, preferably the assay is a transmembrane type 1 neuregulin-1 immunohistochemistry assay. The term 'kit' refers to any manufacture (e.g. a package or a container) comprising at least one reagent (e.g. an antibody, a nucleic acid probe, etc.) for performing an assay which specifically detects the expression of transmembrane type 1 neuregulin-1. Positive and/or negative controls can be included in the kits to validate the activity and correct usage of reagents employed in accordance with the present invention. The design and use of controls is standard and well known.

The following non-limitative examples are given in order to further illustrate the present invention.

EXAMPLES

Example 1

Material and Methods

Cell Culture

Human BM-MSC were isolated from sternal BM aspirates obtained in 10 cancer-free patients before cardiac surgery, as described (40). BM-MSC were cultured in Dulbecco's modified Eagle's medium with low glucose (LG-DMEM) containing 10% fetal bovine serum (FBS), penicillin (100 U/ml) and streptomycin (100 µg/ml) (Invitrogen, Carlsbad, Calif.) and incubated at 37° C. with 5% $CO_2$ in air. Medium was refreshed twice weekly. BM-MSC were used until passage 8.

Human T-MC were isolated from CRC tissue in 3 patients with colon adenocarcinoma, submitted to surgical resection for therapeutic purposes. Normal tissue-derived (N-MC) mesenchymal cells were obtained in the same patients from adjacent normal colorectal tissue at a distance of at least 5 cm from the tumor. Briefly, tissue fragments were cut in small pieces (2-3 $mm^3$) and transferred into a 6-well plate with 100 µl of FCS supplemented with antibiotics added on top of each fragment. Cultures were incubated at 37° C. with 10% $CO_2$ in air for 24 hours. After 24 hours, LG-DMEM containing 10% FBS was added into each well. Medium was refreshed every 3 to 4 days. Cell outgrowth was observed after 3 to 6 days. After 15 days, adherent cells were transferred to a 25 $cm^2$ tissue culture flask by trypsinization with a trypsin-EDTA (0.25%-1 mM) solution (Invitrogen).

Figure 9:
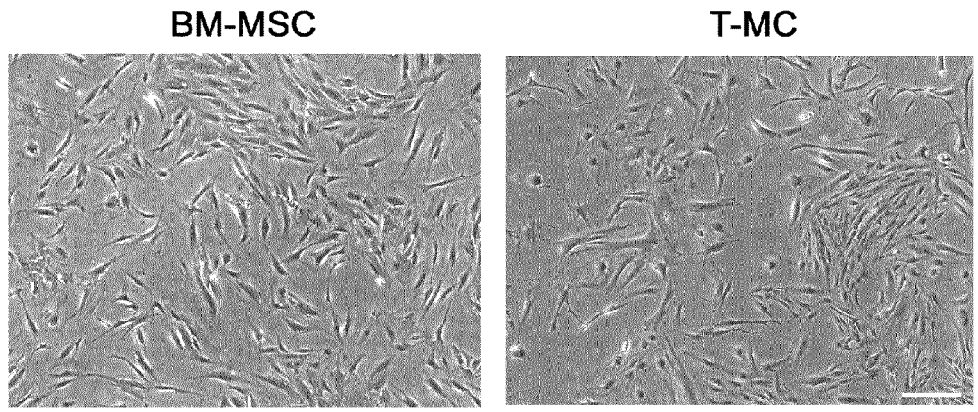
FIG. 9. Characterisation of BM-MSC and T-MC. (A) BM-MSC and T-MC display homogeneous populations of plastic-adherent spindle-shaped fibroblast-like cells. Scalebar, 200 µm. (B) Expression of surface antigens in BM-MSC and T-MC. BM-MSC and T-MC were positive for CD73, CD90 and CD105, and negative for CD34, CD45, CD19, CD11b and HLA-DR. (C) BM-MSC and T-MC were investigated for in vitro adipogenic (left panel) and osteogenic (right panel) differentiation markers. Cells were cultured in differentiation medium or control medium for 3 weeks. Accumulation of lipid droplets (indicating adipogenic differentiation) was demonstrated by staining with Oil red O. Osteogenic differentiation was indicated by calcium deposition as demonstrated by Alizarin red staining. A marked adipogenic and osteogenic differentiation was induced in BM-MSC, whereas only limited a adipogenic and osteogenic differentiation was induced in T-MC. Scalebar, 100 µm (left panel); 200 µm (right panel).
Figure 9:
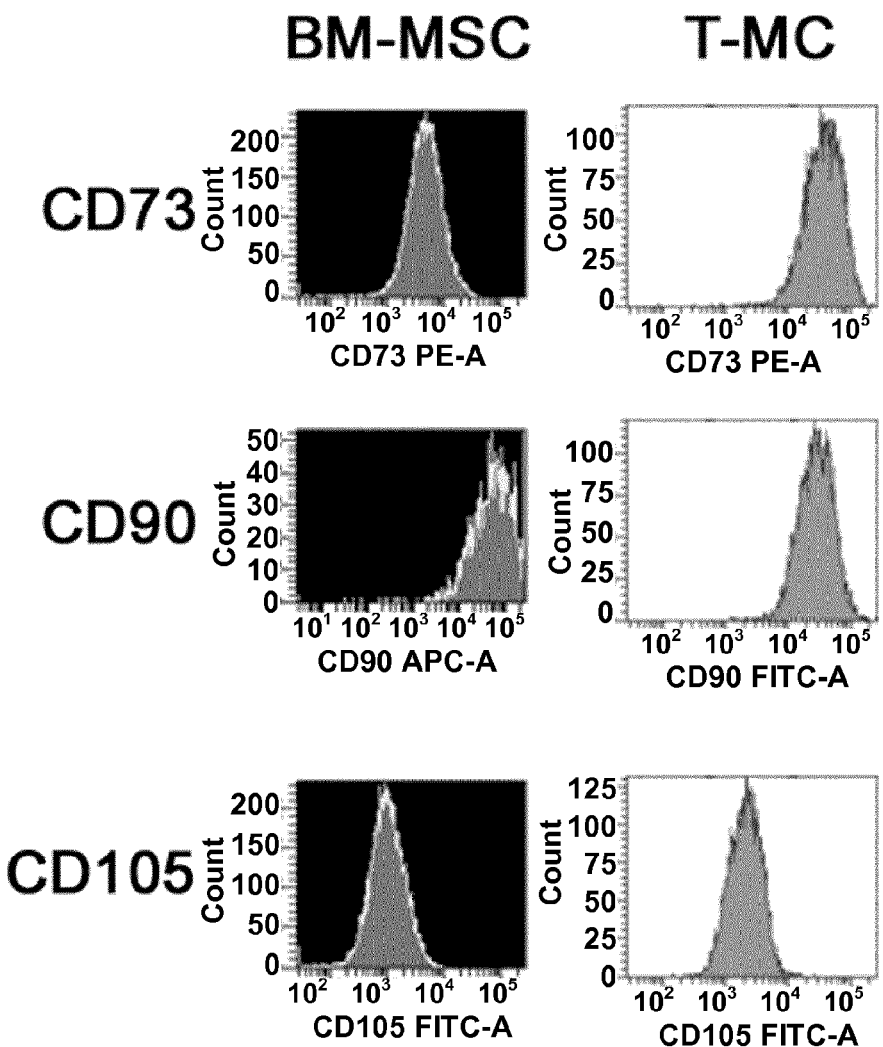
Figure 9:
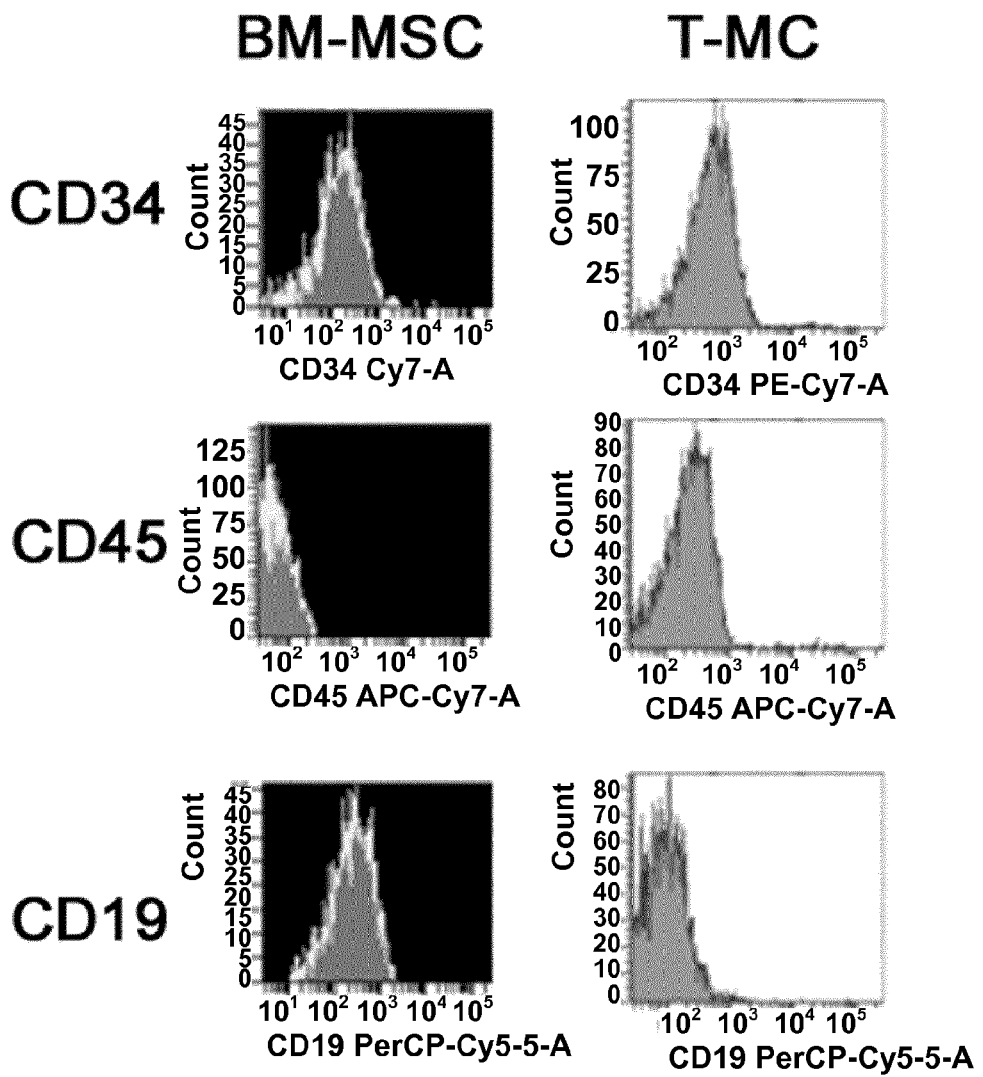
Figure 9:
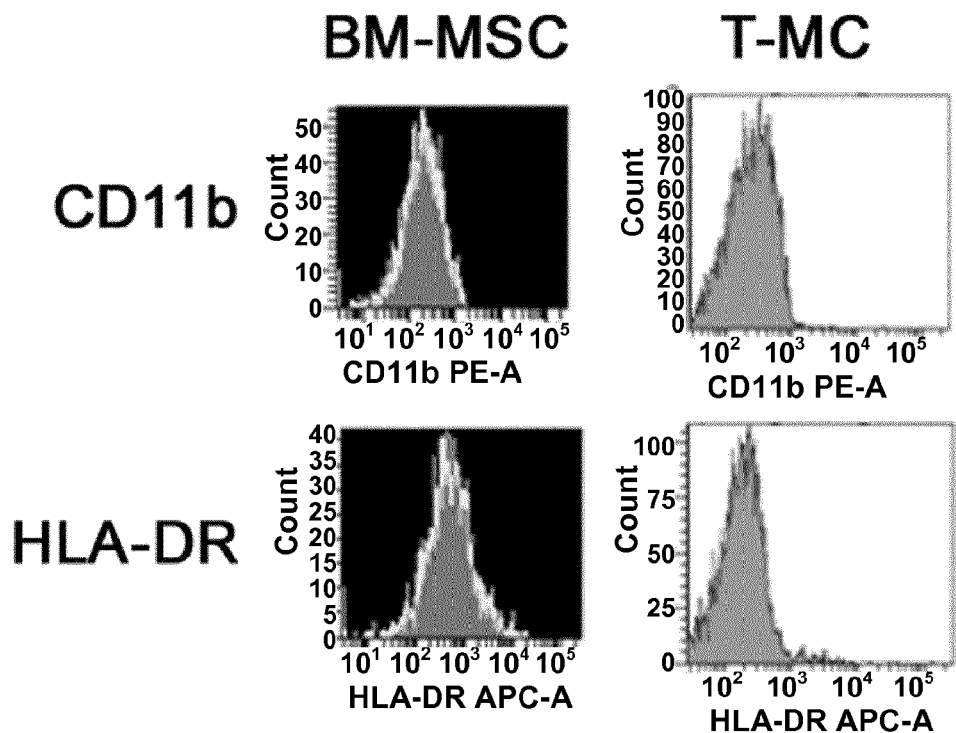
Figure 9:
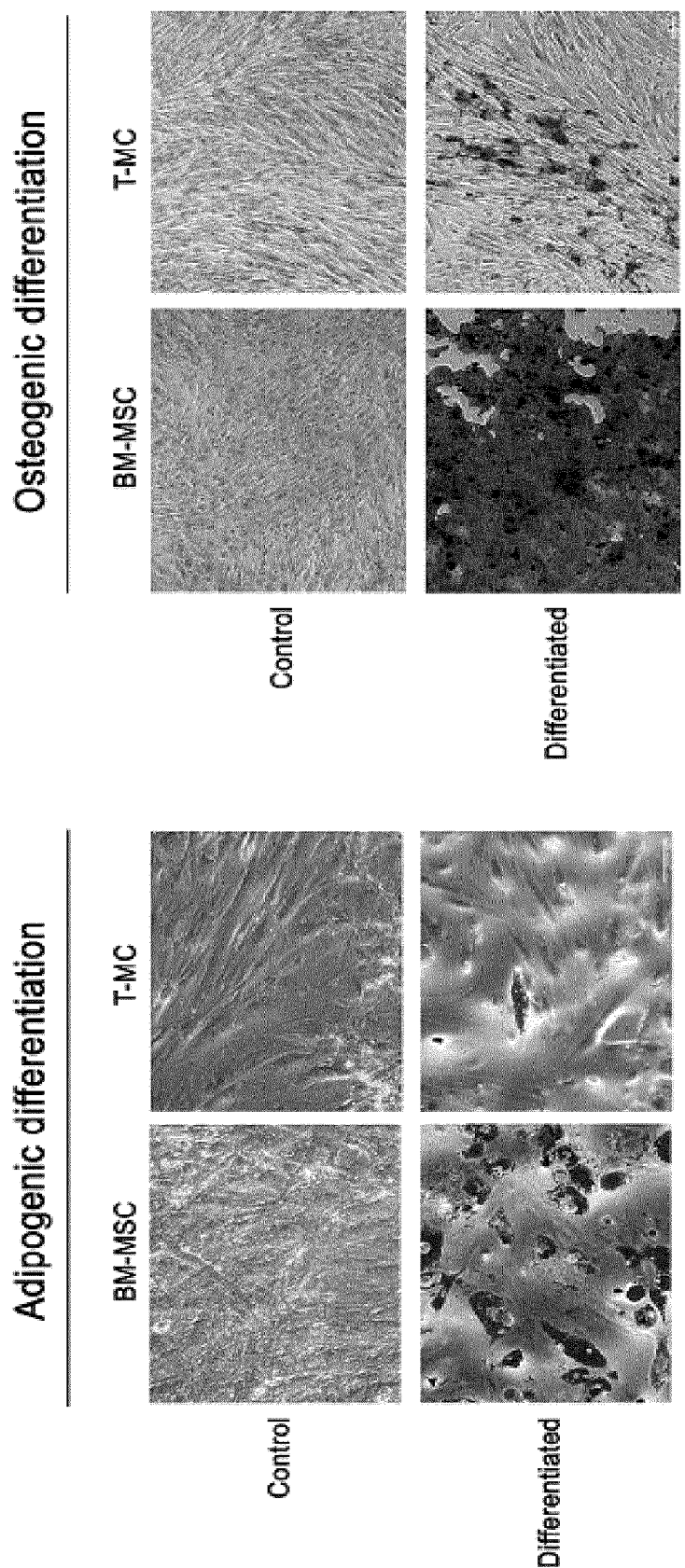

In FIG. 9, BM-MSC and T-MC were compared by phase contrast microscopy and analysed by flow cytometry for the presence of CD73, CD90, and CD105 and the absence of CD34, CD45, CD11b, CD19 and HLA-DR on a FACSAria® (BD Biosciences, San Diego, Calif.). Cells were tested by their capacity to differentiate into adipocytes, osteocytes and chondrocytes with use of a functional identification kit (R&D Systems, Minneapolis, Minn.), in accordance with the manufacturer's instructions.

Human CRC cell line HCT-8/E11 was obtained as described previously (41). HCT 116, SW480, HT-29, LoVo, T84 CRC cell lines and BLM melanoma cell line were purchased from ATCC (Manassas, Va.). All cancer cell lines were maintained in Dulbecco's modified Eagle's medium (DMEM) (Invitrogen) supplemented with 10% FBS and antibiotics (penicillin/streptomycin), and incubated at 37° C. with 10% $CO_2$ in air. Green fluorescent protein (peGFP-C1; Clontech, BD Biosciences) overexpressing HCT-8/E11 cells (HCT-8/E11-GFP) were generated by electroporation (Cell line nucleofector kit V, Lonza, Basel, Switzerland) and stable cell lines were selected in G418 (1 mg/ml). Small interfering RNAs (siRNAs) targeting HER1, HER2, HER3, AKT and NRG-1 and scrambled RNAi negative control were purchased from Qiagen (Venlo, The Netherlands) and were transfected by electroporation. (siHER1 target=5'-TAC GAA TAT TAA ACA CTT CAA-3' (SEQ ID NO:5) and 5'-ATA GGT ATT GGT GAA TTT AAA-3'(SEQ ID NO:6), siHER2 target=5'-CAC GTT TGA GTC CAT GCC CAA -3' (SEQ ID NO:7), siHER3 target=5'-CTT CGT CAT GTT GAA CTA TAA-3'(SEQ ID NO:8), siAKT target=5'-CAC GCT TGG TCC CGA GGC CAA-3'(SEQ ID NO:9), siNRG-1 target=5'-TCG GCT GCA GGT TCC AAA CTA-3'(SEQ ID NO:10)).

Antibodies and Reagents

The following primary antibodies against human epitopes were used: rabbit polyclonal anti-HER1, -2, -3, anti-tNRG-1, mouse monoclonal anti-BAX, anti-BCL-2 (Santa Cruz Biotechnology, Santa Cruz, Calif.), rabbit monoclonal anti-phospho-AKT (p-AKT) (S473), anti-p-BAD (S136), anti-p-HER3 (Y1289), rabbit polyclonal anti-AKT, anti-BAD, anti-p-HER1 (Y1068) (Cell Signalling Technology, Danvers, Mass.), mouse monoclonal anti-tubulin (Sigma-Aldrich, St.-Louis, Mo.), rabbit polyclonal anti-p-HER2 (Y1196 and Y1248), goat polyclonal anti-NRG-β1 EGF domain, anti-NRG-α1 EGF domain, mouse monoclonal anti-p-tyrosine (p-Tyr), anti-p27, (R&D Systems), rabbit polyclonal anti-Ki67 (NeoMarker, Fremint, Calif.,) mouse monoclonal anti-PARP (BD Biosciences), mouse monoclonal anti-cyclin E (Invitrogen), mouse monoclonal anti-cyclin A (Zymed Laboratories, San Francisco, Calif.), mouse monoclonal anti-α-SMA (Biogenex, San Ramon, Calif.) and mouse monoclonal anti-vimentin (Menarini Diagnostics, Zaventem, Belgium). For flow cytometric immunophenotyping, the following mouse and human monoclonal antibodies (Ab) and similarly conjugated isotype-matched control Ab (all from BD Biosciences, unless stated otherwise) were used: CD73-phycoerythrin (PE), CD90-allophycocyanine (APC), CD105-fluorescein isothiocyanate (FITC) (AbD Serotec, Oxford, UK), CD45 peridinyl chlorophyllin-Cy5 (PerCP-Cy5), CD34-PE-Cy7 CD19-PerpCP, CD11b-PE and HLA-DR-APC. LY294002 was purchased from Tocris Bioscience (Bristol, UK), wortmannin from Calbiochem (Meudon, France) and GSK2141795 from GlaxoSmithKline (Research Triangle Pek, N.C.). Pertuzumab (Omnitarg, 2C4) and trastuzumab (Herceptin) were provided by Genentech Inc. (San Fransisco, Calif.), lapatinib (GW572016) by GlaxoSmtihKline and cetuximab (C225, Erbitux) by ImClone Systems Inc. (New York, N.Y.). Secondary antibodies coupled to horseradish peroxidase and phalloidin-TRITC were purchased from Sigma-Aldrich. Recombinant human NRG-β1 EGF domain (rNRG-β1) was supplied by R&D Systems.

Preparation of Conditioned Medium (CM)

$1.5 \times 10^6$ of BM-MSC, T-MC or N-MC cells on 175-cm² flasks were washed three times with 10 ml of serum-free LG-DMEM and incubated for 48 hours at 37° C. with 20 ml serum-free LG-DMEM. The CM was harvested, centrifuged at 1,250 g for 5 minutes at 4° C. and passed through a 0.22 µm filter. The CM was concentrated in centriprep tubes YM-3 (Amicon, Millipore Corp., Bedford, Mass.), sterilized, and diluted with fresh serum-free LG-DMEM: 0.5 ml CM contained soluble factors derived from $5 \times 10^5$ cells. NRG-1-depleted CM was obtained by NRG-1 immunoprecipitation: CM was incubated overnight with a combination of 2.5 µg/ml anti-NRG-α1 and 2.5 µg/ml anti-NRG-β1 EGF domain at 4° C. Heparin-binding factors from the CM were obtained by precipitation with heparin-agarose beads (Pierce, Rockford, Ill.). Heparin-agarose beads were washed with heparin equilibration buffer (10 mM Tris, 50 mM NaCl, pH 7.0) and incubated overnight with CM. Bound proteins were eluted with Laemmli sample buffer (1 M Tris-HCl [pH 6.8], 30% glycerol, 6% SDS, 3% β-mercaptoethanol, 0.005% bromophenol blue) and heated for 5 minutes at 95° C., followed by centrifugation over a spin column.

Liquid Chromatography-Mass Spectrometry/Mass Spectrometry (LC-MS/MS)

The heparin-binding fraction derived from the CM was run on NuPAGE 4%-20% Bis-Tris gradient gels (Invitrogen) in denaturating SDS buffer, stained with 0.5% Coomassie Brilliant Blue (Bio-Rad, Hercules, Calif.) in 40% methanol and 10% acetic acid, and destained in a solution composed of 40% methanol and 10% acetic acid. Gel bands were processed and analyzed by LC-MS/MS as previously described (42). Raw MS/MS files were submitted to the NIH MASCOT Cluster (43) using MASCOT DAEMON. Data were searched against the UNIPROT-SPROT database as described (42). For each peptide identification, MASCOT reports a probability-based ion score, which is defined as $-10 \times \log 10(P)$, where P is the absolute probability that the observed match between the experimental data and the database sequence is a random event. The significance threshold for inclusion of each peptide in the output file is the individual ion score meeting or exceeding its MASCOT identity score threshold (P<0.05). MASS SIEVE was used to parse the MS/MS data from MASCOT and generate protein parsimony reports (http://www-.proteomecommons.org/dev/masssieve). Only peptides that were detected in two separate experiments were considered.

Western Blotting and RTK Array

Cells were harvested with Laemmli lysis buffer (0.125M Tris-HCl (pH=6.8), 10% glycerol, 2.3% sodium dodecyl sulfate [SDS]). Cell surface proteins were isolated by biotinylation (Pierce). For the detection of phosphorylated proteins, cells were grown at 70% confluence and treated for 15 minutes as indicated. Cells were harvested with NP-40 lysis buffer (1% Nonidet P-40 [NP-40][Sigma-Aldrich], 1% Triton X-100 [Bio-Rad] in phosphate-buffered saline [PBS]) and the following protease inhibitors: aprotinin (10 µg/mL), leupeptin (10 µg/mL) (ICN Biomedicals, Costa Mesa, Calif.), phenylmethylsulfonyl fluoride (1.72 mM), NaF (100 mM), NaVO3 (500 mM), and Na4P2O7 (500 mg/mL) (Sigma-Aldrich). Cell lysates (25 µg) and CM (20 µl) were suspended in Laemmli sample buffer and boiled for 5 minutes at 95° C. For immunoprecipitation, cells were harvested with NP-40 lysis buffer, and protease inhibitors. Anti-rabbit antibodies were covalently coupled to sheep anti-rabbit IgG dynabeads (Invitrogen) and then incubated for 2 hours at 4° C. with 500 µg of cell lysate or normal rabbit IgG antibody (R&D Systems) as a negative control. Immunoprecipitates were washed five times with lysis buffer, eluted with 100 µl of Laemmli lysis buffer, and boiled at 95° C. for 5 minutes. Samples were run on NuPAGE 4%-20% Bis-Tris gradient gels (Invitrogen), transferred to polyvinylidene fluoride membranes, blocked in 5% nonfat milk in PBS or 4% bovine serum albumin (BSA) in PBS for phosphorylated proteins with 0.5% Tween-20, and immunostained. Scanning densitometry was carried out with the Quantity One Program (Bio-Rad).

A human Phospho-RTK Array kit (R&D Systems) was used to simultaneously detect the relative tyrosine phosphorylation levels of 42 different RTKs (R&D Systems).

Flow Cytometric Cell Cycle Analysis

For analysis of cell cycle distribution, the DNA Reagent Kit was used (BD Biosciences) in accordance with the manufacturer's instructions. Cell cycle progression was analyzed by growing HCT-8/E11 and HCT 116 cells to 50% confluence, followed by serum starvation for 24 hours, and treatment with $CM^{BM-MSC}$ or serum-free control medium for 24 h. Cells were harvested by trypsinization, washed and frozen in buffer solution until the time of analysis. Cellular DNA content was monitored on a FACSCanto flow cytometer (BD Biosciences). DNA QC particles (BD Biosciences) were used for instrument set up and quality control. Mitotic index was calculated using ModFit LT software (Verity Software House).

Preparation of Interstitial Fluids from CRC Tissue and Adjacent Normal Colorectal Tissue Interstitial fluids from CRC tissue and adjacent normal colorectal tissue were prepared as described previously (44). Briefly, about 0.3 g of fresh tissue was collected in PBS, cut into pieces of 3 mm³ and placed in a 10-ml conical plastic tube containing 1.0 ml of PBS. Samples were incubated for 1 hour at 37° C. with 10% $CO_2$ in air, centrifuged at 1,000 rpm for 2 minutes followed by aspiration of the supernatant. Samples were further centrifuged for 20 minutes at 3,500 rpm at 4° C. The final supernatant with a protein concentration that ranged from 1 to 4 mg/ml was used for functional experiments.

Assessment of Cell Numbers

To assess the effect of rNRG-β1 or CM on cell numbers, a total of 9 wells of seeded cells were counted for each condition (triplicate samples×3 countings). First, $1 \times 10^4$ CRC cells were seeded on a 6-well plate in DMEM supplemented with 10% FCS. After 24 hours, cells were treated as indicated under serum-free conditions; medium was changed every 3 days. The total number of viable cells in each well was counted with a Countess automated cell counter (Invitrogen) every three days for 9 days; trypan blue staining was used for exclusion of dead cells.

Collagen Invasion Assays

Single Cell Collagen Invasion Assay

Collagen invasion assays were performed as described previously (45). Briefly, $1 \times 10^5$ CRC cells were seeded on type I collagen-coated 6-well plates and treated with CM derived from $5 \times 10^5$ BM-MSC or T-MC supplemented with DMEM 10% FBS and antibiotics as indicated.

Morphology and invasion into collagen was analysed after 24 hours and quantified by means of the factor shape ([perimeter]²/[4πarea]) and invasion index. The number of invasive and noninvasive cells was counted in 10 randomly selected microscopic fields with a 20× objective and 10× eye piece by two blinded observers using an inverted phase-contrast microscope (DMI 3000B; Leica, Wetzlar, Germany). The invasion index was calculated as the ratio of the number of cells that invaded the gel divided by the total number of cells counted in each field. Collagen matrices were fixed in 3% paraformaldehyde for 10 minutes and phalloidin-TRITC (Sigma-Aldrich) staining as described (45). Cells were imaged with a Zeiss 510 META confocal laser-scanning microscope (Carl Zeiss, Micro-imaging Inc., Heidelberg, Germany) using a 488 argon and a 543 HeNe laser. Images were acquired using a Plan Apochromat 63×/1.4 oil DIC or a Plan Apochromat 100×/1.4 oil DIC objective. All the images shown are collapsed z-stacks.

Heterotypic Spheroid Collagen Invasion Assay

A bottom gel layer of collagen type I solution was mixed with $1 \times 10^6$ BM-MSC and gelified. To form multicellular spheroids, $2 \times 10^5$ HCT-8/E11 GFP cells/ml in 6 ml DMEM+ 10% FCS were cultured for 72 hours at 37° C. in a 50-ml Erlenmeyer flask on a gyrotory shaker with 10% $CO_2$ and 70 rpm. Spheroids with a diameter of +/−300 µm were used. HCT-8/E11-GFP spheroids mixed up with collagen type I solution were gently poured on the preformed BM-MSC-containing gel layer. Every 24 hours bright field and GFP-fluorescence images were made of 10 spheroids on a Zeiss Axiovert 200M fluorescence microscope (Carl Zeiss Micro-Imaging GmbH, Göttingen, Germany) for a maximum of 96 hours. For haematoxylin and eosin (H&E) and Ki67 staining, collagen matrices were fixed in 4% buffered formol for 12 hours followed by a wash with PBS. Fixed matrices were transferred to 70% ethanol until use. Matrices were embedded in paraffin, sectioned and stained with H&E or anti-Ki67.

Matrigel Invasion Assay

Transwell chambers with polycarbonate membrane filters (6.5 mm diameter, 8 µm pore size) were coated with Matrigel. The filter was placed in a 6-well plate with control medium or $CM^{HCT-8/11}$ as chemo-attractant and $2 \times 10^4$ BM-MSC were added to the upper compartment of the Transwell chamber. After 48 hours, a cotton swab removed the cells that did not invade through the pores. Cells on the lower surface of the membrane were stained with DAPI (Sigma, 0.4 mg/ml). Fluorescent images (Axiovert 200M; Carl Zeiss) were converted into binary images and invasive cells were counted in 10 microscopic fields per filter by computerized Image J analysis.

Animal Studies

Animal studies were approved by the Local Ethical Committee for Animal Experiments, Faculty of Medicine and Health Sciences, Ghent University, Belgium. Four-week-old female Swiss nu/nu mice (10 animals per group) (Charles River Laboratories, Brussels, Belgium) were inoculated subcutaneously (s.c.) with $10^6$ CRC cells (HCT-8/E11, SW480 and HCT 116) either alone or combined with $2 \times 10^6$ BM-MSC suspended in 100 µl sterile PBS. To assess the effect of soluble factors on tumorigenesis, mice were inoculated s.c. with $10^6$ cancer cells in 100 µl sterile CM derived from 2.5× $10^6$ BM-MSC, or control medium. For these experiments, intratumoral injection of the CM (50 µl) was performed every three days. To assess the effect of pertuzumab on BM-MSC-induced tumorigenesis, $10^6$ HCT-8/E11 cells were injected s.c. alone or combined with $2 \times 10^6$ BM-MSC. After one week, mice were treated three times a week with intraperitoneal (i.p.) injection of vehicle (PBS) only or pertuzumab (600 µg/mouse). Tumor volume was estimated by using the equation, $V = 0.4 \times a \times b^2$, where V is the volume, a is the length of the major axis of the tumor, and b is the length of its minor axis. he animals were sacrificed when the tumors were approximately 1-1.5 $cm^3$, in compliance with regulations for the use of vertebrate animals in research. Primary tumors were extracted, weighted and fixed in 4% buffered formol for 12 hours, followed by a wash with PBS. Fixed tumors were transferred to 70% ethanol until use. Tumors were embedded in paraffin, sectioned and stained with H&E. Immunohistochemistry (IHC) using TUNEL, anti-α-SMA (Biogenex), anti-vimentin and anti-Ki67 antibodies was performed on paraffin sections, using a NexES automated slide staining system (Ventana Medical Systems, Tucson, Ariz.). Cell proliferation (Ki67 positivity) was quantified as % of positive cancer cells per high power field averaged across 12 images from 2 primary tumors per cell line.

Quantitative Real-Time PCR (qRT-PCR)

Total RNA from cells was isolated using the Trizol reagent (Invitrogen) according to the manufacturer's protocol. RNA was treated with a DNase kit (DNA-free) to remove all remaining DNA according to the manufacturer's protocol (Applied Biosystems, Austin, Tex.). RNA concentration and purity were measured on the Nanodrop ND-1000 (Nanodrop Technologies, Wilmington, Del.). First-strand cDNA was synthesized using a high-capacity RNA-to-cDNA kit (Applied Biosystems) according to the manufacturer's guidelines. Quantitative real-time PCR was performed using 100 ng cDNA, Taqman gene expression master mix reagent, and Assays-On-Demand (Applied Biosystems) for NRG1 (Assay ID Hs00247620_m1) and a control gene, B2M (Assay ID Hs00984230_m1), on an ABI PRISM 7900 HT Sequence Detection System (Applied Biosystems) using the comparative CT method (DDCT). The cycling conditions were 2 minutes at 50° C., 10 minutes at 95° C., and 40 cycles at 95° C. for 15 seconds and 60° C. for 60 seconds Patient Samples and Immunohistochemistry Primary CRC tissues (n=54 subjects; 26 male, 28 female; age range 41-94 years), adjacent normal colorectal tissues (n=4), liver metastases (n=3) and adjacent normal liver tissues (n=3) were collected between August 1996 and March 2000 at University Hospital Antwerp. Written informed consent was obtained from each patient according to the recommendations of the local ethics committee.

Tissues were snap frozen in liquid nitrogen immediately after resection and stored at −80° C. Tumor staging was performed according to Union for International Cancer Control (UICC): 10 tumors were staged as stage I ($T_{1-2}N_0M_0$), 15 tumors stage II ($T_{3-4},N_0,M_0$), 21 tumors stage III ($T_{1-4},N_{1-2},M_0$) and 8 tumors stage 1V ($T_x,N_x,M_1$). Subjects were at time of surgery. A comprehensive list of all primary tumors is presented in Table 2.

tNRG-1 IHC was performed on frozen sections. Frozen tissues were embedded in Optimal Cutting Temperature (OCT) compound on a metal block and 5 µm frozen sections were cut onto positively charged slides, air dried and fixed in methanol for 10 minutes, and then air dried again. Consecutive sections were blocked with 10% normal goat serum, rinsed with PBS and incubated with rabbit polyclonal anti-tNRG-1 (Santa Cruz) at a dilution of 1:250 (0.8 µg/ml) or mouse monoclonal anti-α-SMA (Biogenex) at a dilution of 1:100 (100 µg/ml) in buffer containing 10 mM Tris-HCl, pH7.5, 150 mM NaCl, 0.01% (v/v) Tween 20, 3% normal goat serum, and 0.1% BSA at room temperature for 1 hour. As negative staining controls, separate slides of tissue sections were incubated in PBS in absence of primary antibodies. After washing with PBS, all sections were incubated with a biotinylated goat anti-rabbit or anti-mouse secondary antibody (1:400 dilution) at room temperature for 45 minutes, followed by incubation with streptavidin-biotin peroxidase solution at 1:500 dilution. Colour reaction was developed in diaminobenzidine solution, and counterstaining was performed with Mayer's hematoxylin solution. The tNRG-1 protein IHC signal was scored taking into account both the percentage of cells stained and signal intensity: (i) score low: weak or absent tNRG-1 staining in less than 25% of stromal cells; (ii) score high: more than 25% of stromal cells containing strong tNRG-1 cytoplasmic and at plasma membrane staining. Two observers quantified independently five microscopic fields at magnification 100× of each patient sample.

Statistical Analysis

All statistical calculations were performed using MedCalc (Version 11.0; MedCalc Software, Mariakerke, Belgium). Comparisons were performed using a two-way repeated measures analysis of variance (ANOVA) test followed by a Student's t-test at individual time points (area and factor shape in heterotypic spheroid collagen invasion assays, cell number, and tumor volume), two-sided unpaired Student's t-test following D'Agostino-Pearson testing for normal distribution (Matrigel invasion, Ki67 proliferation index and TUNEL apoptotic index), chi-square test (invasion index) or Mann-Whitney test (factor shape in single cell collagen invasion assays, tumor weight). Comparison of tNRG-1 expression between normal versus tumor tissue and tNRG-1 association with 5-year PFS were performed using chi-square test. tNRG-1 association with clinicopathological parameters was analysed by the chi-square test for trend. All data presented are representative of at least three independent experiments and are expressed as mean and standard error. All statistical tests were two-sided. P-values less than 0.05 were considered to be statistically significant.

Results

The Role of BM-MSC in Invasion, Survival and Tumorigenesis of Human CRC Cells

To investigate the functional effect of soluble factors derived from naive BM-MSC on CRC cells, collagen invasion experiments were performed. HCT-8/E11, SW480 and HCT 116 cells were seeded on a collagen type I gel; treatment with $CM^{BM-MSC}$ induced robust morphological changes with formation of invasive extensions in HCT-8/E11, SW480 and HCT 116 CRC cells (FIG. 1A, upper panel). After 24 hours of treatment, the number of elongated, invasive CRC cells was 2.4-5,5-fold higher upon stimulation with $CM^{BM-MSC}$ (P=0.002 for HCT-8/E11, P=0.008 for HCT 118, and P=0.006 for SW480, chi-square test) (FIG. 1A, lower panel). F-actin staining by phalloidin-TRITC revealed a rounded appearance for HCT-8/E11 cells under control conditions, and an elongated morphology with multiple protrusions after treatment with $CM^{BM-MSC}$ (FIG. 1B, right panel). The mean factor shape of $CM^{BM-MSC}$-treated HCT-8/E11 cells was 1.8 times that of controls, and indicated statistically significant spreading (P=0.001; Mann-Whitney test) (FIG. 1B, left panel).

Coculture of BM-MSC with HCT-8/E11-GFP spheroids in a collagen type I gel, without physical contact between the spheroids and BM-MSC demonstrated more irregularity, as measured by the factor shape, and a higher increase in projected surface area of the HCT-8/E11-GFP spheroids over time (FIGS. 1C, D and E) (P<0.001, two-way repeated measures ANOVA). The spheroid factor shape had an initial mean value of 1.4±0.2 at 0 hours, indicating approximate circularity. At 96 hours, the spheroid factor shape was 2.5±0.1 in controls, compared to 4.5±0.4 in cocultures (difference=2.0, 95% of the difference CI=0.9 to 3.0, P=0.002, Student's t-test) (FIG. 1D, left panel). Investigation of the F-actin organisation by confocal microscopy revealed that the control spheroids had smooth edges with occasional invasive extension formation (FIG. 1D, right panel), whereas the spheroids in coculture had an irregular perimeter with cells invading the surrounding collagen matrix. The spheroid area was significantly higher after 24 hours of coculturing with BM-MSC (difference=6631, 95% CI of the difference=2965 to 10297, P=0.002, Student's t-test). At 96 hours, the spheroid area was 2-fold higher under coculture conditions (difference=60488, 95% CI of the difference=46181 to 74796, P<0.001, Student's t-test) (FIG. 1E, left panel). There was no difference in the Ki67 proliferation index between control and coculture conditions at 96 hours (difference=4.5, 95% CI of the difference=-15.5 to 6.5, P=0.382, Student's t-test) (FIG. 1E, right panel), despite the higher surface area in the latter.

Figure 2:
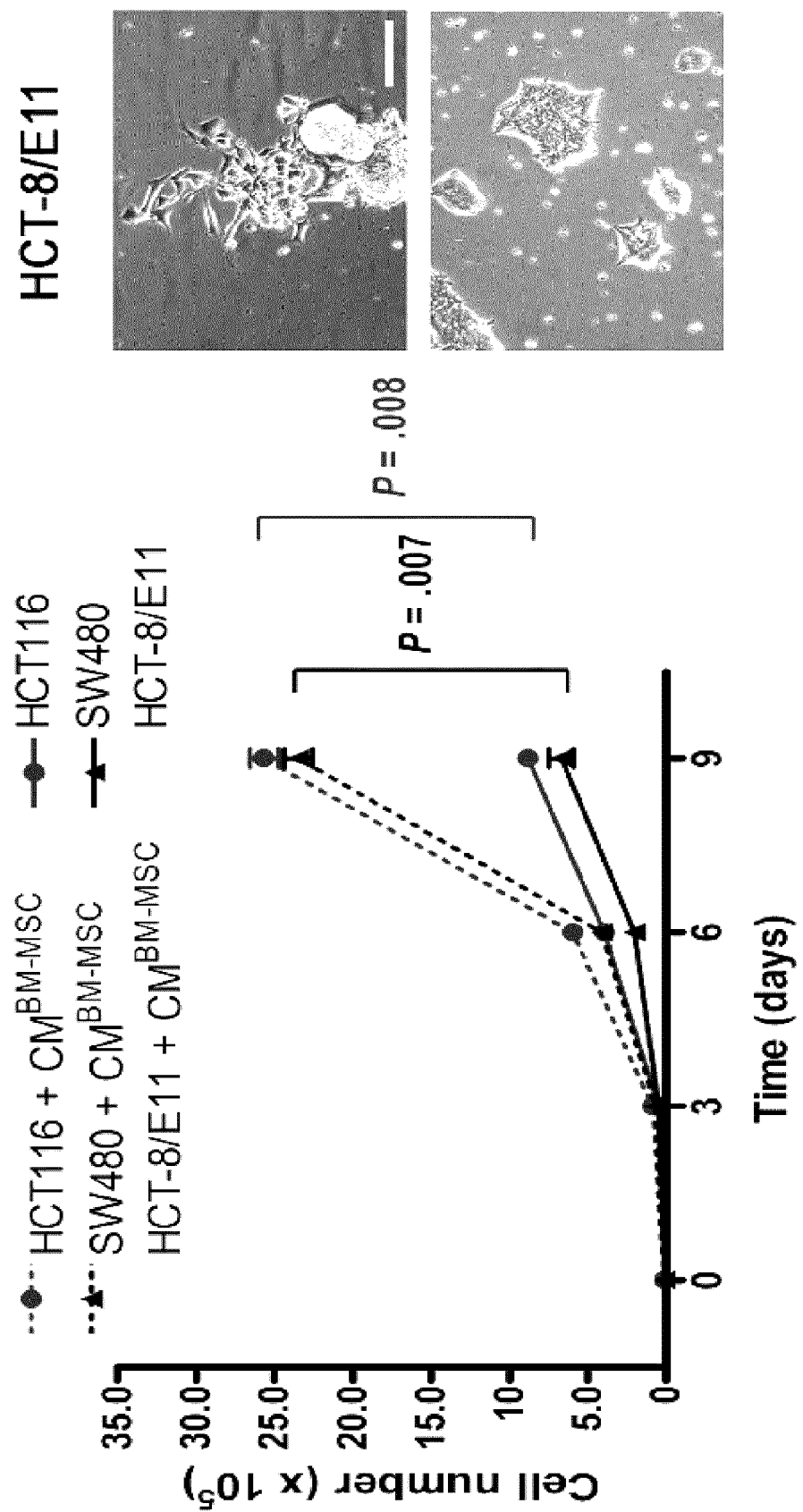
FIG. 2. Effect of BM-MSC or $CM^{BM-MSC}$ on survival and tumorigenesis of CRC cells. (A) Quantification of the total number of viable CRC cells treated with $CM^{BM-MSC}$ at different time intervals under serum-free conditions. Results are expressed as mean and standard error from three independent experiments. P values were calculated using two-way repeated measures ANOVA test; statistically significant P values are indicated (left panel). Phase-contrast images of CRC cells treated with $CM^{BM-MSC}$ for 6 days under serum-free conditions. Scale bar, 100 µm (right panel). (B) Western blot evaluation of AKT (S473) and BAD (S136) phosphorylation and AKT and BAD expression levels in HCT-8/E11 treated with $CM^{BM-MSC}$ for 15 minutes (left panel); and BAX and BCL-2 expression levels in HCT-8/E11 treated with $CM^{BM-MSC}$ for 6 hours (middle panel); and evaluation of full length (113 kDa) and cleaved (89 kDa) PARP in HCT 116 treated with $CM^{BM-MSC}$ for 6 hours (right panel). For the middle panel, tubulin was used as loading control. (C) Nude mice were injected s.c. with $10^6$ CRC cells (HCT-8/E11 or SW480 or HCT 116) with or without $2 \cdot 10^6$ BM-MSC or $CM^{BM-MSC}$ or with $2 \cdot 10^6$ BM-MSC alone. Number of animals inoculated, animals presenting tumors and tumor take rate for each condition. (D) en (E) Weekly assessment of tumor volume by measurement of the external diameter. Mice were killed at variable time points (i.e., the ethical endpoint that limits tumor volume formation (+/−1 $cm^3$). (F) Tumor weight was assessed after surgical resection. In (D), (E) en (F) results are expressed as mean and standard error from 10 xenografts from three independent experiments. For tumor volume, P values were calculated using two-way repeated measures ANOVA test. For tumor weight, P values were calculated using Mann-Whitney test; statistically significant P values are indicated. (G) Selected xenografts within two weeks of inoculation were subjected to IHC using the Ki67 proliferation marker (upper panel) or TUNEL assay to detect the percentage of cells with apoptotic nuclei in green (red arrows) (lower panel). Representative images of HCT-8/E11 vs HCT-8/E11+BM-MSC xenografts are shown. Data are expressed as the mean and standard error calculated from 12 images of two primary tumors. Scale bar, 100 µm; inset scale bar, 50 µm FIG. 3. Effect of $CM^{BM-MSC}$ on HER activation in CRC cells. (A) Lysates of HCT-8/E11 cells treated with $CM^{BM-MSC}$ were analysed for the relative level of tyrosine phosphorylation of 42 RTKs. Each RTK is spotted in duplicate and the phosphorylated HER1, HER2, HER3 and HER4 (p-HER1-4) are indicated. (B) Indicated lysates were immunoprecipitated (IP) with a rabbit polyclonal antibody against HER3 or with rabbit immunoglobulins (IgG). Immunoprecipitated complexes were resolved by SDS-PAGE and immunoblotted with anti-p-Tyr or with anti-HER3 antibody. (C) Western blot evaluation of Y 1289 p-HER3 and total HER3 expression levels in HCT-8/E11, HCT 116 and SW480 cells treated with $CM^{BM-MSC}$. (D) Western blot evaluation of Y1068 p-HER1 and Y1196, Y1248 p-HER2, and HER1 and HER2 expression levels in HCT/8E11 treated with $CM^{BM-MSC}$. (E) Western blot evaluation of Y1289 p-HER3, S473 p-AKT and S136 p-BAD, and total HER1, HER2, HER3, AKT and BAD expression levels after siHER1, 2 and 3 transfection in HCT-8/E11 treated with $CM^{BM-MSC}$. Tubulin was used as a loading control. (F) Effect of drug or antibody treatments on Y1289 p-HER3 and S473 p-AKT in HCT-8/E11 treated with $CM^{BM-MSC}$. Cetuximab was used at 3 µM, lapatinib at 1 µM and trastuzumab and pertuzumab at 25 μg/ml. In (A-F) cells were treated for 15 minutes with $CM^{BM-MSC}$.
Figure 2:
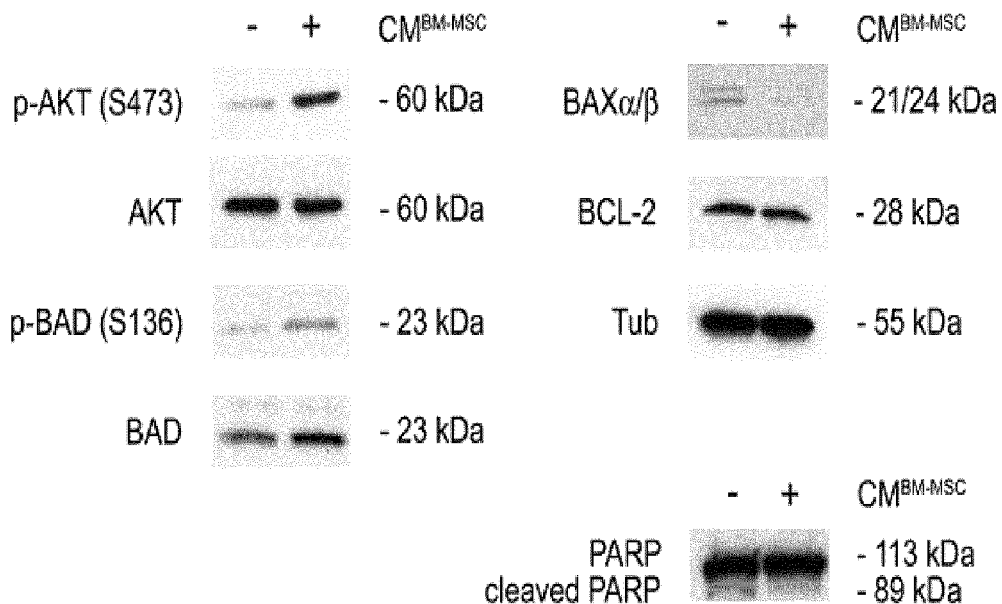
Figure 2:
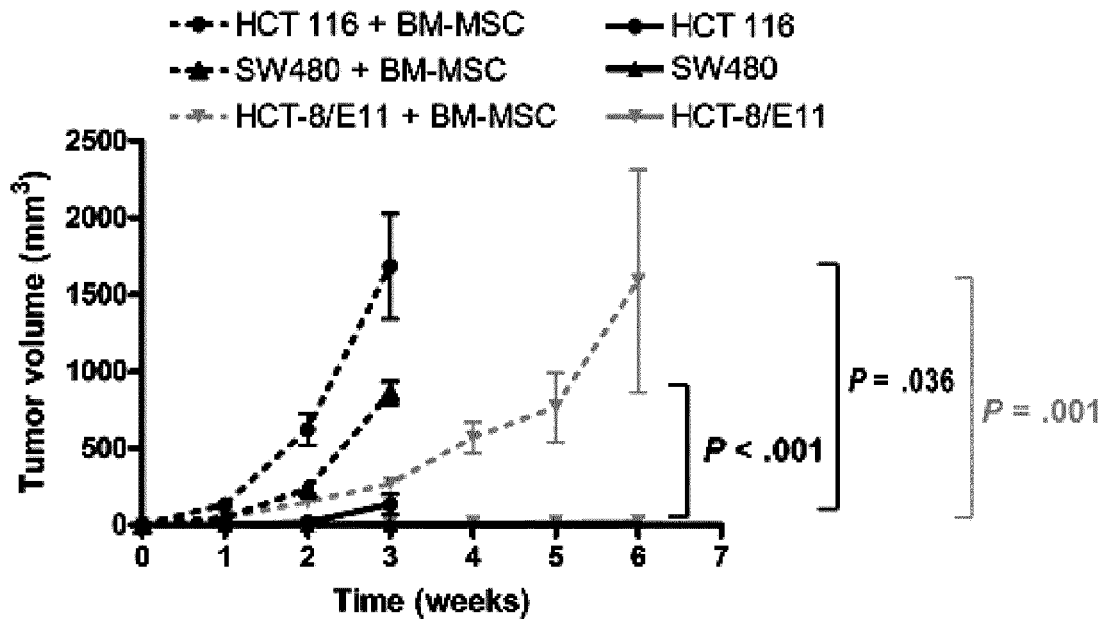
Figure 2:
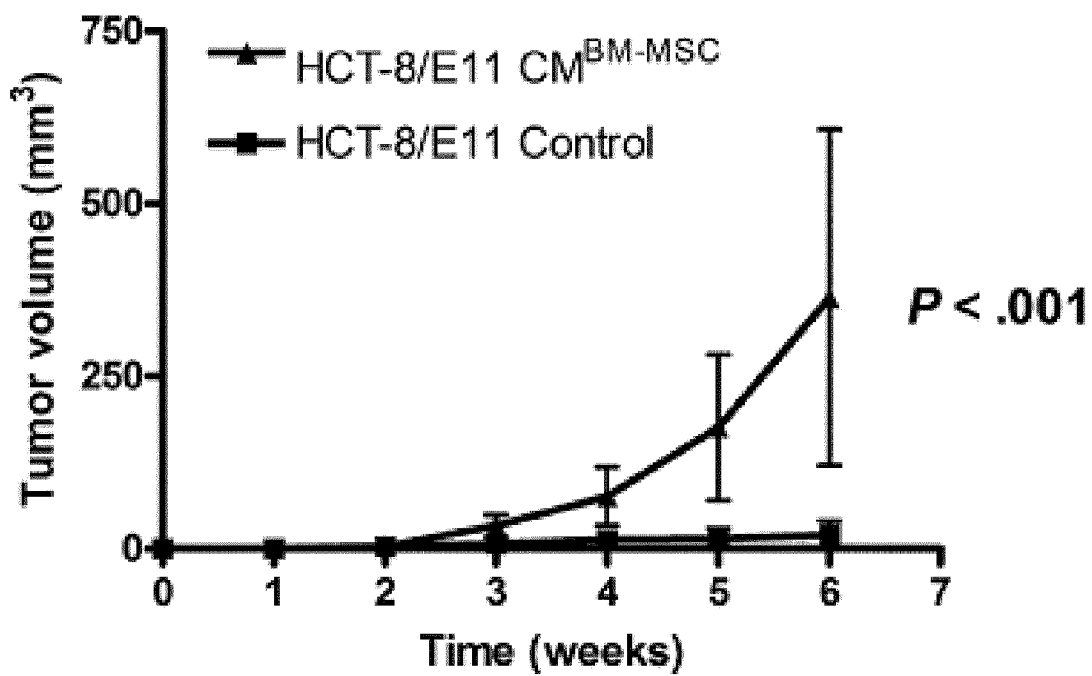
Figure 2:
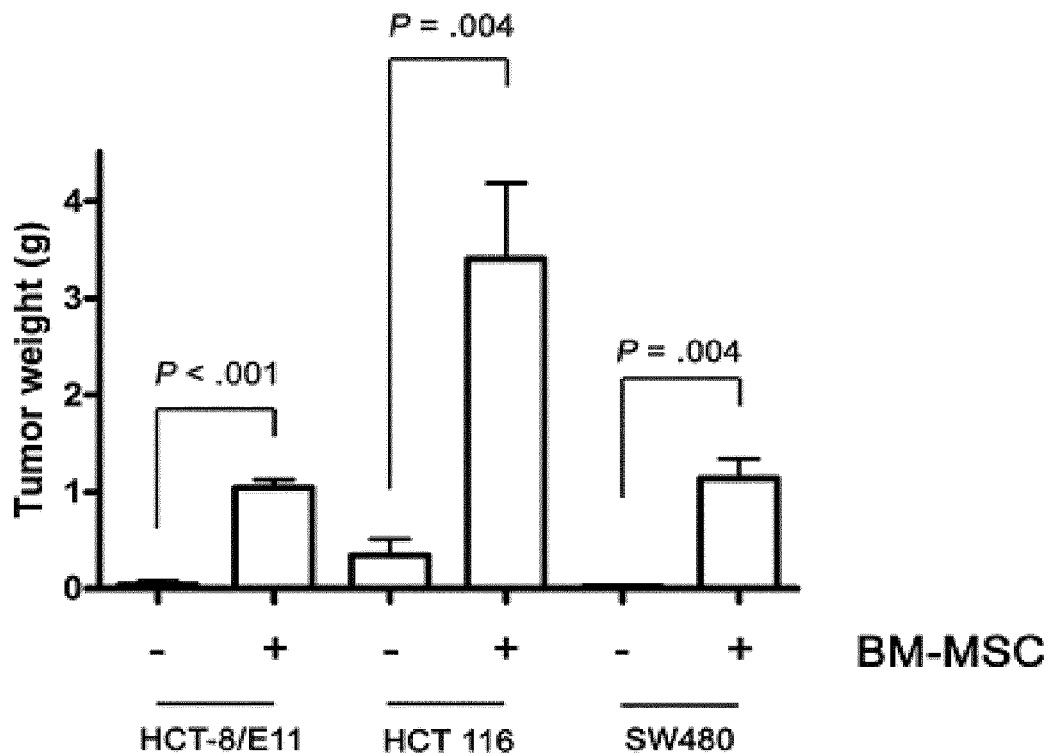
Figure 2:
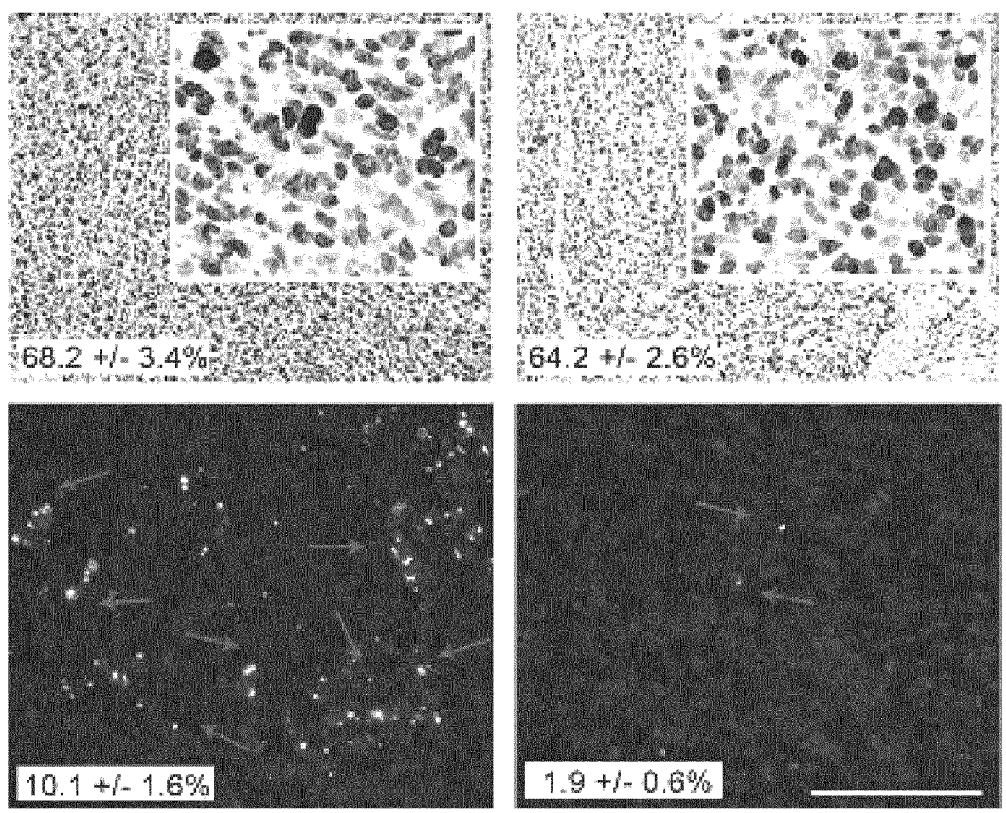
Figure 10:
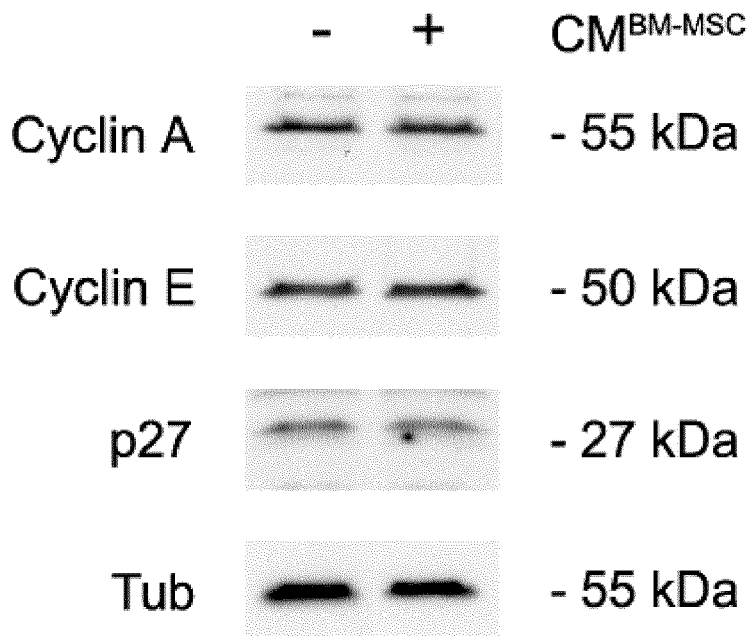
FIG. 10. Effect of BM-MSC on cell cycle progression of CRC cell lines. (A) Western blot evaluation of cyclin A, E and p27 expression levels in HCT-8/E11 treated for 24 hours with $CM^{BM-MSC}$ after 24 hours serum starvation. Tubulin was used as loading control. (B) Effect of $CM^{BM-MSC}$ on cell cycle progression. HCT-8/E11 and HCT 116 cells were grown to 50% confluence, followed by 24 hours serum starvation, and 24 hours treatment with $CM^{BM-MSC}$. Percentages of HCT-8/E11 and HCT 116 cells in G1, S, and G2 stage of the cell cycle, as measured by flow cytometry, are represented.
Figure 10:
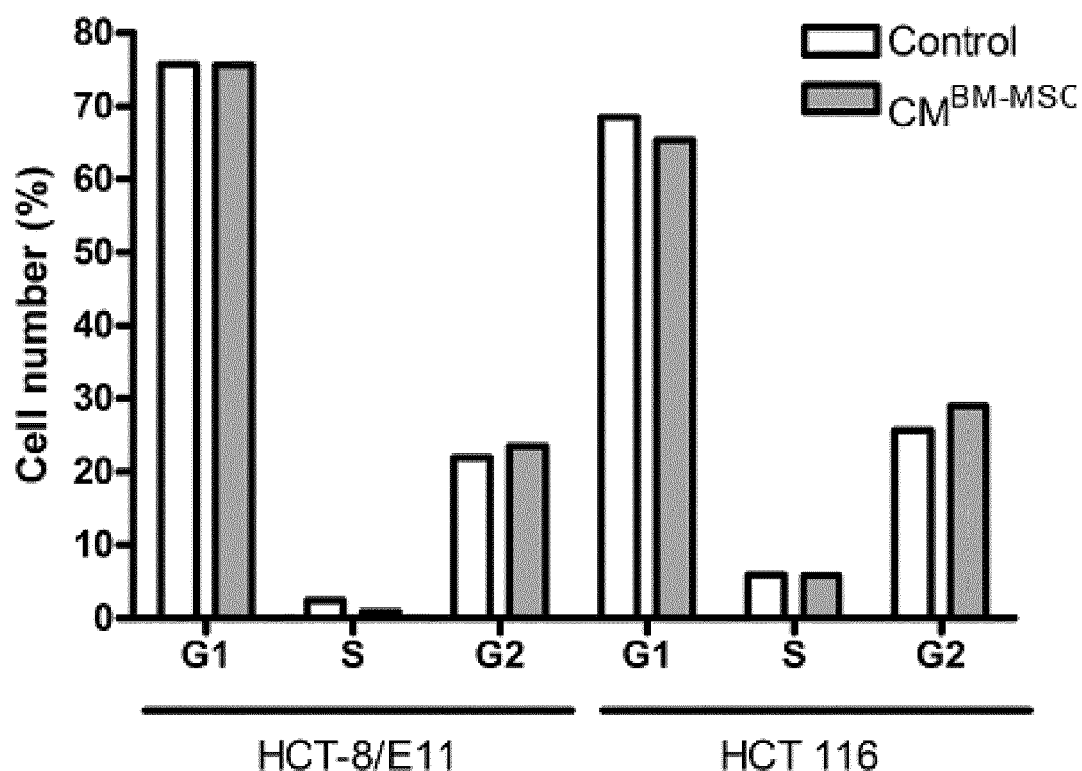

We further investigated whether $CM^{BM-MSC}$ affected cell survival and tumorigenesis. Treatment of CRC cells with $CM^{BM-MSC}$ seeded on tissue culture substrate resulted in a significantly higher increase in cell counts over time (P=0.001 for HCT-8/E11; P<0.001 for HCT 116; P=0.006 for SW480, two-way repeated measures ANOVA test) (FIG. 2A, left panel). A characteristic feature of $CM^{BM-MSC}$ treatment was the formation of numerous dome-like foci piled up over the cell islands and the relative absence of floating cells, as shown for HCT-8/E11 cells (FIG. 2A, right panel). $CM^{BM-MSC}$-enhanced cell number was not due to cell cycle progression, as we did not find altered expression of positive and negative cell cycle regulators (cyclins NE and p27; FIG. 10A). Accordingly, cell cycle analysis demonstrated a similar distribution of cells in G1, S and G2/M phases of the cell cycle in $CM^{BM-MSC}$-treated HCT-8/E11 (FIG. 10B) and HCT 116 cells and their respective controls. Because cancer cell growth can be due to increased cell survival, we tested whether $CM^{BM-MSC}$ protects against apoptosis. $CM^{BM-MSC}$ stimulated S473 phospho-AKT (p-AKT) abundance and the pro-survival AKT kinase activity (FIG. 2B) through S136 phosphorylation and inactivation of the cell death-executing protein BAD (46). $CM^{BM-MSC}$-treated CRC cells exhibited lower expression levels of BAX, and stable expression of BCL-2, thereby decreasing the BAX/BCL-2 ratio and making $CM^{BM-MSC}$-treated cells less sensitive to apoptosis (FIG. 2B, upper right panel) (47). The anti-apoptotic effect of $CM^{BM-MSC}$ was further confirmed by reduced PARP cleavage in HCT 116 cells exposed to $CM^{BM-MSC}$ (FIG. 2B, lower right panel).

Figure 11:
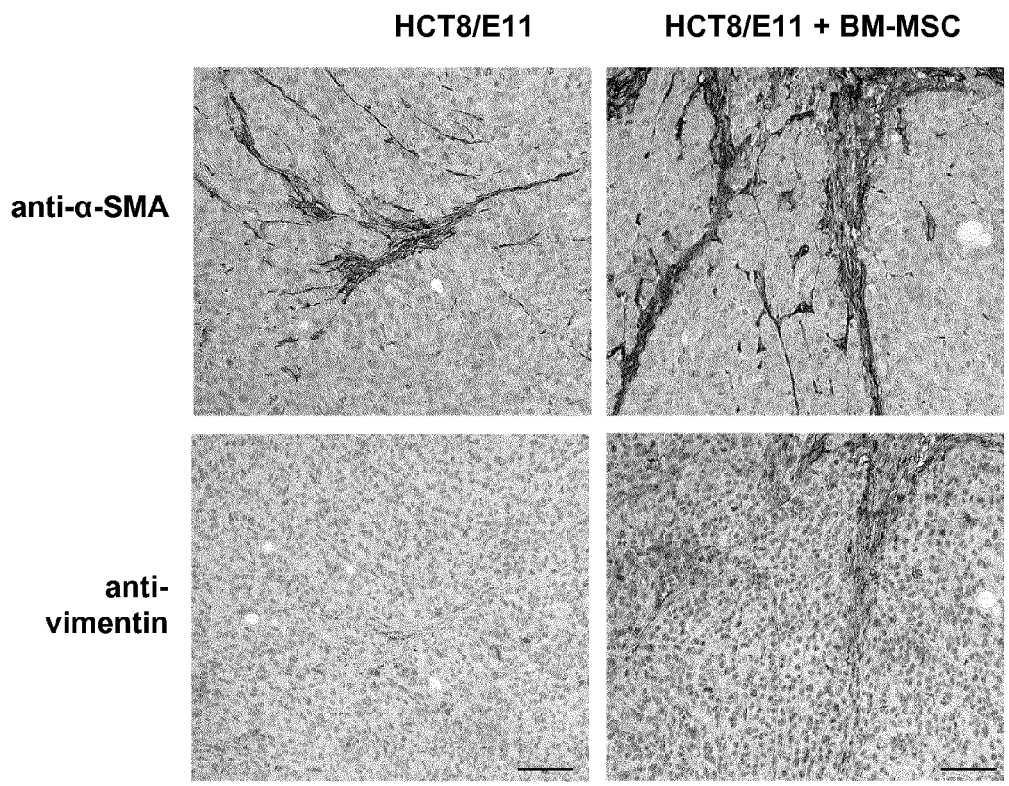
FIG. 11. Presence of murine and human mesenchymal cells in tumor xenografts established by human CRC cells in immunodeficient mice. IHC of paraffin-embedded HCT-8/E11 or HCT-8/E11+BM-MSC tumor sections using an antibody recognising both human and mouse α-SMA and a human-specific anti-vimentin antibody. Scalebar, 100 µm.
Figure 12:
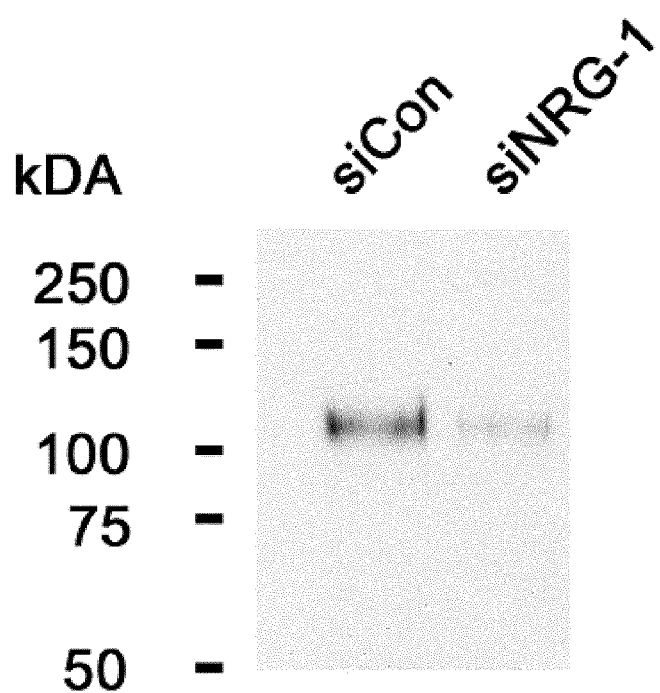
FIG. 12. Specificity of tNRG-1 antibody. BLM cells were transfected with NRG-1 siRNA targeting the Ig-like domain of NRG-1. tNRG-1 expression was analysed by Western blotting using a tNRG-1 antibody directed against an NRG-1 epitope common to the "a" type cytoplasmic tail, the most abundant variant.

To further confirm the direct role of BM-MSC or their soluble factors on cell survival and tumorigenesis of CRC cells in vivo, we implanted s.c. 1×10⁶ HCT-8/E11, SW480 or HCT116 cells, either alone or mixed with 2×10⁶ BM-MSC or $CM^{BM-MSC}$ in Swiss nu/nu mice. BM-MSC and $CM^{BM-MSC}$ boosted tumor take (FIG. 2C) and tumor growth of CRC cells (P<0.001 for HCT-8/E11; P=0.036 for HCT 116; P=0.001 for SW480, two-way repeated measures ANOVA test) (FIGS. 2D and E). S.c. injection of 2×10⁶ BM-MSC alone did not form any tumors (FIG. 2C). Notably, BM-MSC stimulated approximately 10-fold tumor growth for all CRC cells with an average 34-fold increase in tumor weight (FIG. 2F) (P<0.001 for HCT-8/E11; P=0.004 for HCT 116 and SW480; Mann-Whitney test). To examine the mechanism of increased tumorigenesis, we collected a subset of tumors within the first two weeks of inoculation. Viable areas in control and BM-MSC boosted tumors were without any concomitant change in cell cycle engagement, as revealed by Ki67 staining (difference=4.0, 95% CI of the difference=-5.6 to 13.6, P=0.375, Student's t-test) (FIG. 2G, upper panel). On the contrary, we found large areas of cell necrosis in control xenografts as well as upregulation of TUNEL staining indicative of significantly more apoptotic cells in control compared to BM-MSC xenografts (difference=8.2, 95% CI of the difference=5.0 to 11.4, P<0.001; Student's t-test) (FIG. 2G, lower panel). In addition, the co-inoculated BM-MSC survived in the xenografts for periods up to 6 weeks after injection, and made up to 10% of the tumor volume, as determined by IHC using an antibody specific for human vimentin, which HCT-8/E11 cells fail to express. Interestingly, another 10% of the tumor volume was infiltrated by mesenchymal cells of mouse origin as demonstrated by the presence of α-smooth muscle actin (α-SMA) positive mesenchymal cells which were negative for human vimentin (FIG. 11). These experiments clearly demonstrate that the massive increase in tumor volumes are primarily caused by increased cancer cell numbers.

Paracrine Activation by BM-MSC of HER3 and AKT in CRC Cells

Figure 3:
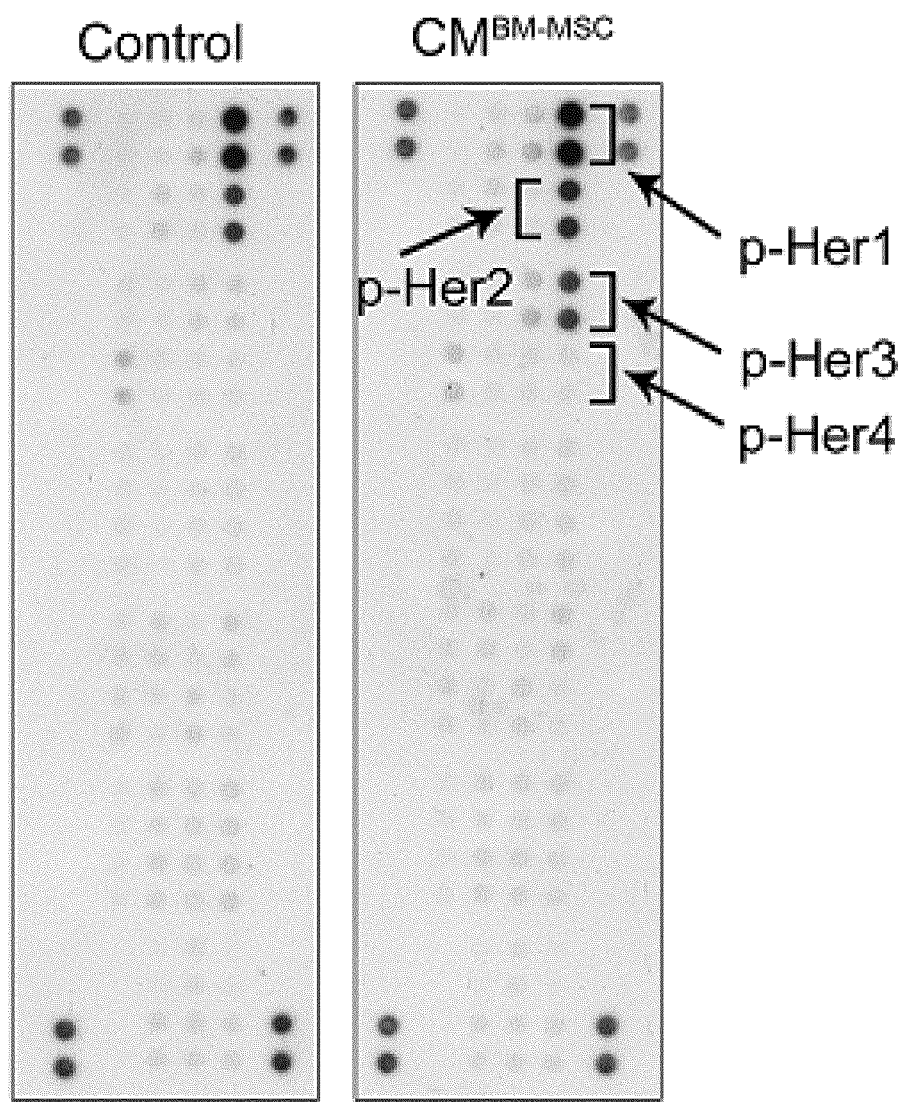
Figure 3:
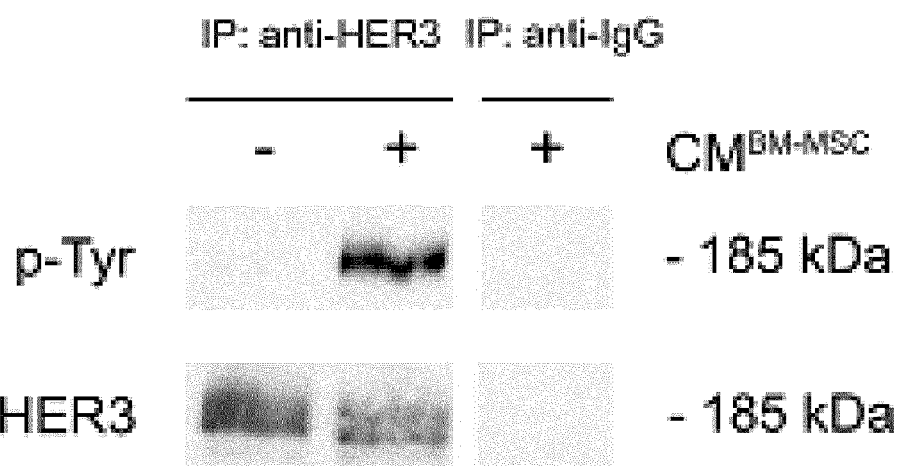
Figure 3:
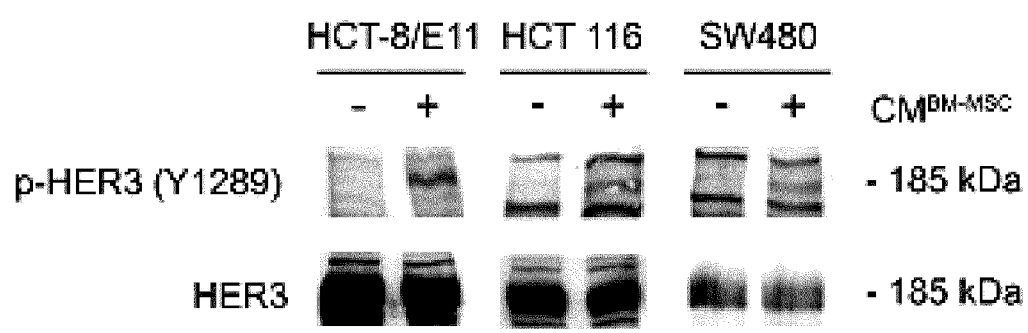
Figure 3:
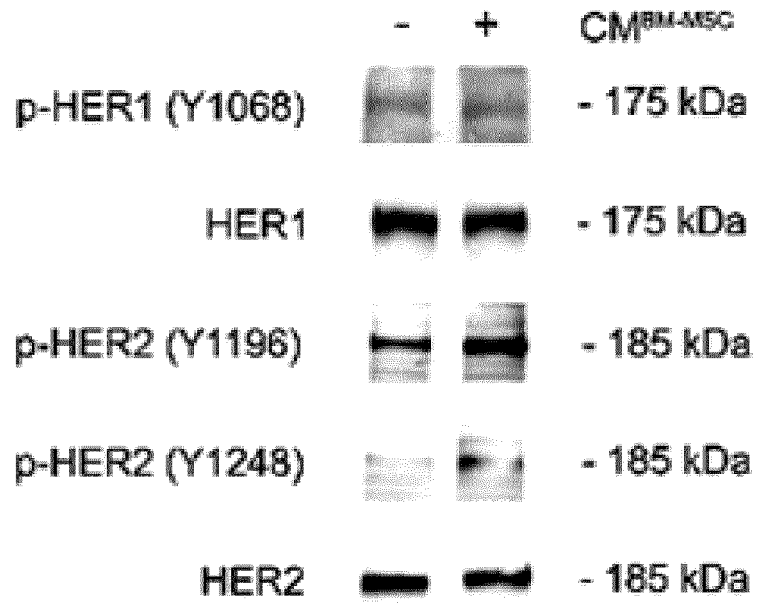
Figure 3:
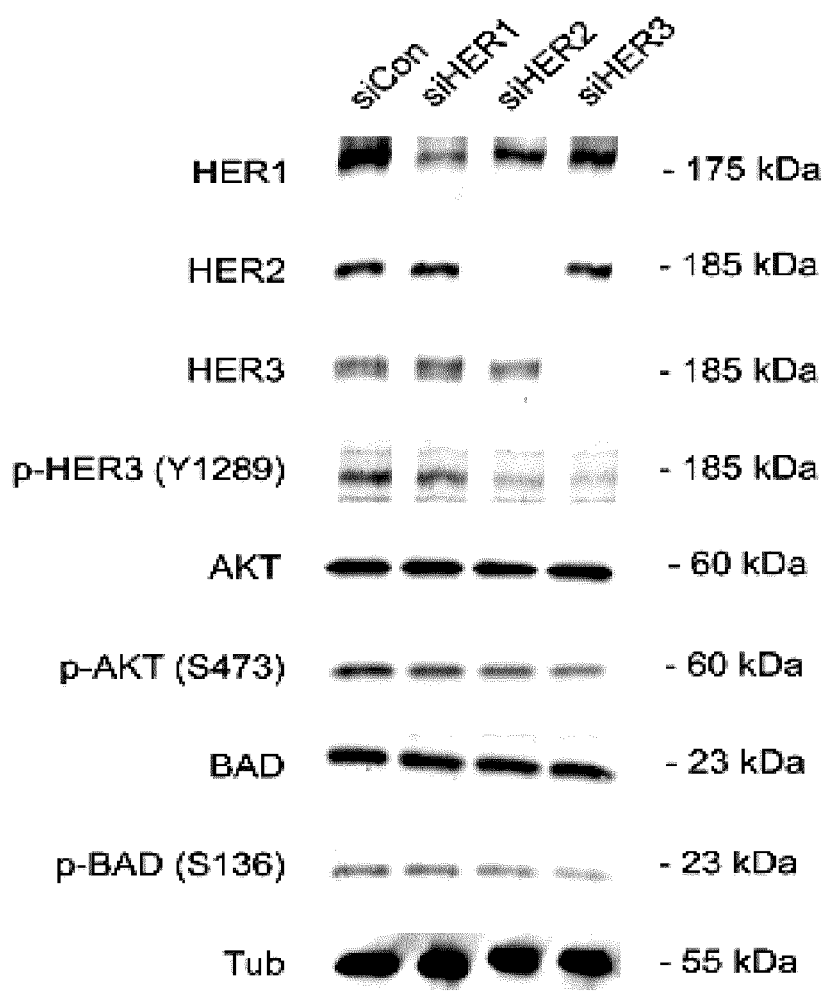
Figure 3:
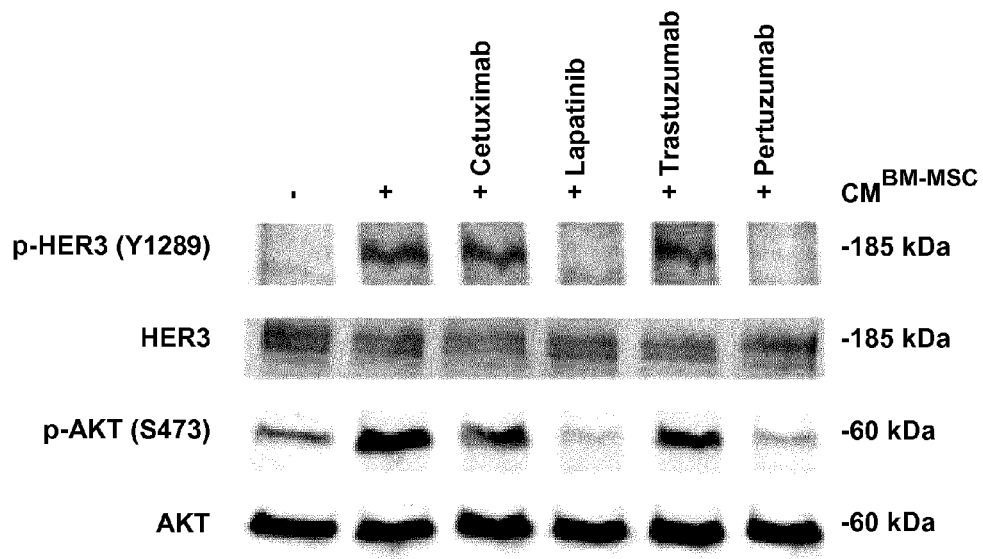

We analysed the relative tyrosine phosphorylation levels of a series of 42 different RTKs in HCT-8/E11 cells treated with $CM^{BM-MSC}$ (FIG. 3A). The screening revealed that the HER3 phosphorylation level was 10-fold higher after $CM^{BM-MSC}$ treatment, as shown in two duplicate immunoreactive spots (p-HER3). HER3 tyrosine phosphorylation after $CM^{BM-MSC}$ treatment was further confirmed by HER3 immunoprecipitation followed by detection with HRP-conjugated phospho-tyrosine (p-Tyr) antibody (FIG. 3B).

HER3 has six tyrosine containing binding sites for the p85 regulatory subunit of PI3K, including Y1289, which distinguishes HER3 signaling from other HER family members (48). One of the best characterized targets of PI3K is AKT kinase. The HER3/PI3K/AKT-pathway regulates survival, cytoskeletal rearrangements and invasion (49). As shown in FIG. 3C, $CM^{BM-MSC}$ stimulated Y1289 p-HER3 in 3 distinct CRC cell lines. Since HER3 has only minimal intrinsic tyrosine kinase activity, its phosphorylation is mainly dependent on physical association with other HER family members (50). HER2 is the preferential heterodimerisation partner of all HER receptors (51). The screening of 42 RTKs revealed that both HER1 and HER2 showed a basal activity in HCT-8/E11. $CM^{BM-MSC}$ treatment did not change HER1 phosphorylation levels but total HER2 phosphorylation increased modestly (FIG. 3A). In agreement, Western blotting revealed increased Y1196 and Y1248 p-HER2 upon $CM^{BM-MSC}$ treatment with no change in Y1068 p-HER1 (FIG. 3D).

Next, we investigated whether the activation status of HER3 was dependent on interaction with HER1 or HER2 by using siRNAs, HER neutralizing antibodies and pharmacologic inhibitors. As shown in FIG. 3E transient targeting of HER2 by single siRNA depleted HER2 protein by 99%, and was accompanied by a 54% decrease in $CM^{BM-MSC}$-induced HER3 activation, indicating that HER3 activation was dependent on HER2 expression levels. In agreement, 82% depletion of HER3 by single siRNA resulted in a 61% decrease in $CM^{BM-MSC}$-induced HER3 activation. On the contrary, 50% depletion of HER1 by pooled siRNAs had no significant effect on $CM^{BM-MSC}$-induced HER3 activation. Furthermore, we demonstrated that AKT and BAD phosphorylation was dependent on HER3 activation using HER-specific siRNAs. Control siRNA had no effect on $CM^{BM-MSC}$-induced HER, AKT and BAD phosphorylation. The requirement of functional heterodimers for HER3 activation was further substantiated by selective HER neutralizing antibodies and pharmacological inhibitors (FIG. 3F). Addition of pertuzumab, a humanized monoclonal antibody (mAb), that inhibits HER2/HER3 heterodimer formation (52) as well as lapatinib, a HER1 and HER2 tyrosine kinase inhibitor that leads to a reduction in HER3 transphosphorylation (53, 54), decreased $CM^{BM-MSC}$-induced HER3 activation in HCT-8/E11 cells by 67% and 72% respectively. Trastuzumab, another humanized mAb that binds to a different HER2 epitope then pertuzumab blocking ligand-independent HER2 dimerization and signaling (52, 55), and cetuximab, a mouse-human chimeric mAb targeting HER1 (56), did not significantly reduce $CM^{BM-MSC}$-induced HER3 activation. In addition, pertuzumab and lapatinib reduced AKT activation in $CM^{BM-MSC}$-treated cells by 79 and 82% respectively whereas cetuximab and trastuzumab only marginally reduced AKT activation.

Figure 4:
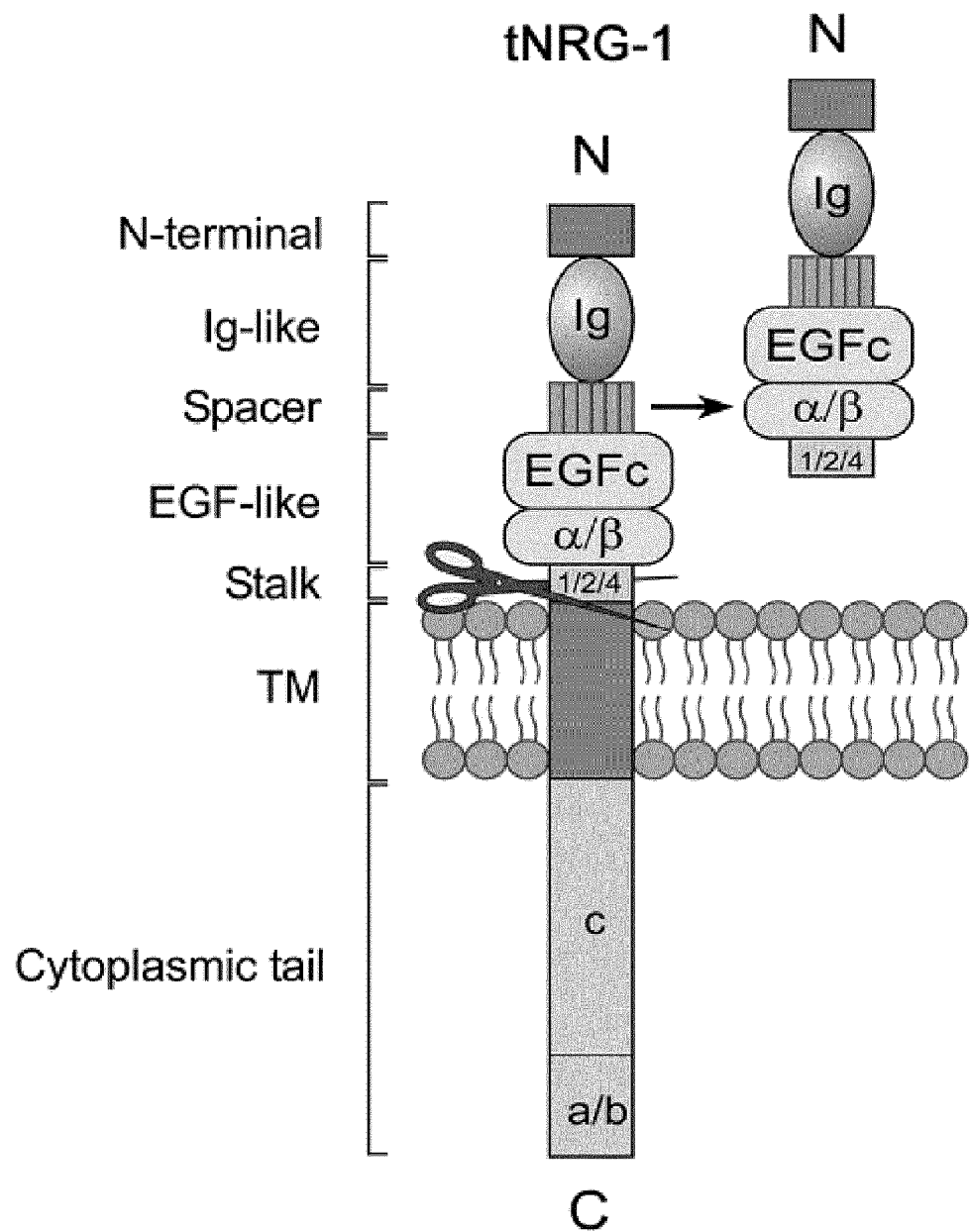
FIG. 4. Expression of tNRG-1 and release of soluble NRG-1 by BM-MSC. (A) Schematic representation of tNRG-1 and soluble NRG-1 with the distinct domains. tNRG-1 can be characterised by the presence of a type specific N-terminal region (N-term), a heparin-binding Ig-like domain (not present in type III and VI), a spacer region (sp) with putative glycosylation sites, an EGF-like domain consisting of an EGFc and a variable EGF domain (α/β), a variable stalk region (1/2/4), a transmembrane domain (TM), a common cytoplasmic tail (c) and a variable-length cytoplasmic tail (a/b). Proteolytical cleavage in the stalk region (indicated by the scissors) generates soluble, active NRG-1. (B) tNRG-1 expression was analysed by Western blotting of whole cell lysates of BLM, HCT-8/E11 and BM-MSC (left panel) or after streptavidin or control protein G-sepharose bead precipitation of biotinylated BM-MSC (right panel). (C) Relative mRNA quantity of NRG-1 by qRT-PCR in BLM, HCT-8/E11 and BM-MSC. (D) Heparin-binding factors in $CM^{BM-MSC}$ were purified by heparin precipitation. SDS-PAGE was performed on the purified heparin-binding proteins. Proteins from the 40-50 kDa region were trypsinized and peptides were identified via LC-MS/MS analysis. Four unique peptides from the EGFc domain and Ig-like domain of NRG-1 were identified (peptide sequences from top to bottom, respectively. SEQ ID NO: 1-4). (E) Western blot analysis demonstrating the presence of NRG-α1 and NRG-β1 in heparin-binding fraction of $CM^{BM-MSC}$ purified by heparin precipitation.
Figure 4:
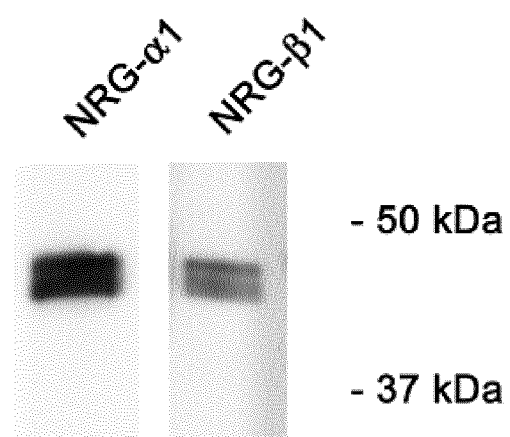

Expression of Transmembrane NRG-1 (tNRG-1) Precursor and Release of Biologically Active NRG-1 by BM-MSC Western blotting was performed using a specific anti-tNRG-1 antibody directed against an NRG-1 epitope common to the "a" type cytoplasmic tail, the most abundant variant (FIG. 4A). The 105 kDa immunoreactive band corresponding to the molecular weight of type I NRG-1, also known as heregulin (57-59), was identified in BM-MSC (FIG. 4B, left panel) and the positive control BLM (37). The localization of the 105-kDa immunoreactive band at the cell surface was confirmed for BM-MSC by biotinylation (FIG. 4B, right panel). Most importantly, a series of human CRC cell lines, including HT-29, Caco-2, LoVo, HCT 116, T84 and SW480, were negative for tNRG-1 expression in immunoblots (data not shown). In agreement, qRT-PCR analysis validated these (non-)expression levels at the mRNA level (FIG. 4C).

Proteomic analysis performed on heparin-binding proteins from $CM^{BM-MSC}$ confirmed the presence of four unique NRG-1 peptides identified by mass spectrometry in the 40-50 kDa region. As shown in FIG. 4D, the peptides were derived from the heparin-binding Ig-like domain and the common EGF (EGFc) domain of NRG-1. Western blotting using antibodies against the NRG-α1 and NRG-β1 EGF-like domains demonstrated two immunoreactive bands at the expected 40-44 kDa region, most likely as a result of glycosylation (FIG. 4E) (59, 60).

Figure 5:
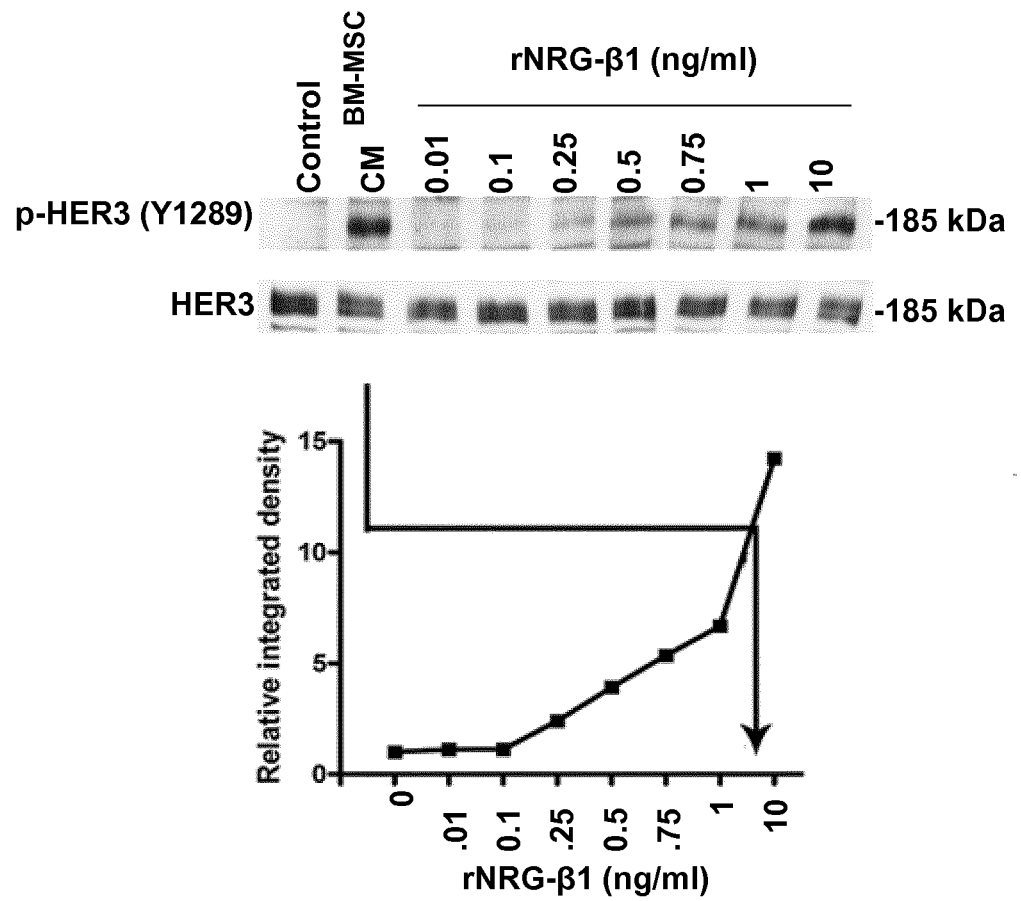
FIG. 5. Release of functionally active NRG-1 by BM-MSC. (A) Western blot evaluation (upper panel) and quantification (lower panel) of Y1289 p-HER3 induced by treating HCT-8/E11 with $CM^{BM-MSC}$ or rNRG-β1 for 15 minutes at increasing concentrations. The arrow indicates that, by extrapolation, the phosphorylating capacity of $CM^{BM-MSC}$ is equivalent to that of +/−10 ng/ml rNRG-β1. (B) Western blot evaluation of Y1068 p-HER1 and Y1196 and Y1248 p-HER2 and total HER1 and HER2 expression levels in HCT-8/E11 treated with rNRG-β1 (10 ng/ml) for 15 minutes. (C) Quantification of collagen invasion of HCT-8/E11, HCT116 and SW480 CRC cells treated for 24 hours with rNRG-β1 at the indicated concentrations. Invasion indices are mean and standard error of at least three independent experiments. P values were calculated using the chi-square test; statistically significant P values are indicated. (D) Quantification of the total number of viable HCT-8/E11 cells at different time intervals treated with increasing concentrations of rNRG-β1 under serum-free conditions. Results are expressed as mean and standard error from three independent experiments. P values were calculated using two-way repeated measures ANOVA test; statistically significant P values are indicated (left panel). Phase-contrast images of HCT-8/E11 cells treated for 6 days with rNRG-β1 (10 ng/ml) under serum-free conditions. Scale bar, 100 μm (right panel). (E) Western blot evaluation of S473 p-AKT and S136 p-BAD and total AKT and BAD expression levels in HCT-8/E11 treated with $CM^{BM-MSC}$ for 15 minutes (left panel); and BAX and BCL-2 expression levels in HCT-8/E11 treated with rNRG-β1 (10 ng/ml) for 6 hours (upper right panel); and full length (113 kDa) and cleaved (89 kDa) PARP in HCT 116 treated with rNRG-β1 (10 ng/ml) for 6 hours (lower right panel). For the upper right panel, tubulin was used as a loading control. (F) Western blot evaluation of Y1289 p-HER3 and total HER3 expression levels in HCT-8/E11 treated with $CM^{BM-MSC}$ supplemented with anti-NRG-α1/β1 neutralizing antibodies (2.5 μg/ml) or a combination of both or the control IgG isotype for 15 minutes.
Figure 5:
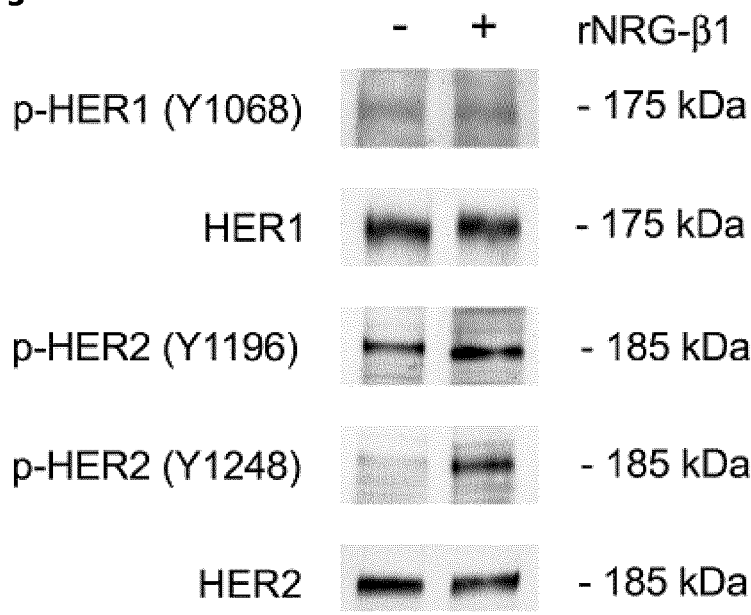
Figure 5:
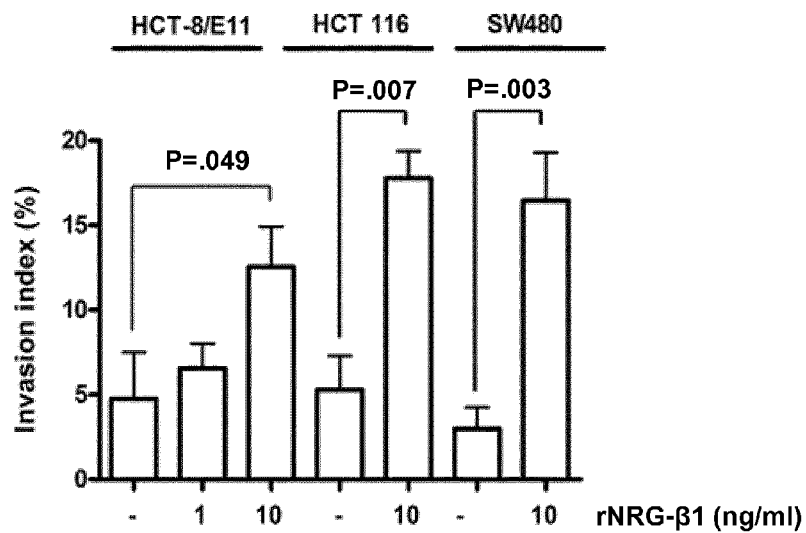
Figure 5:
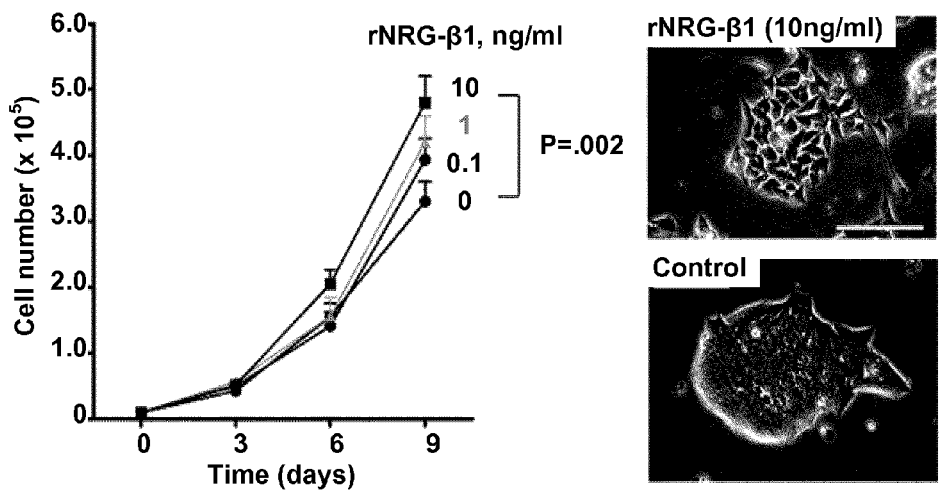
Figure 5:
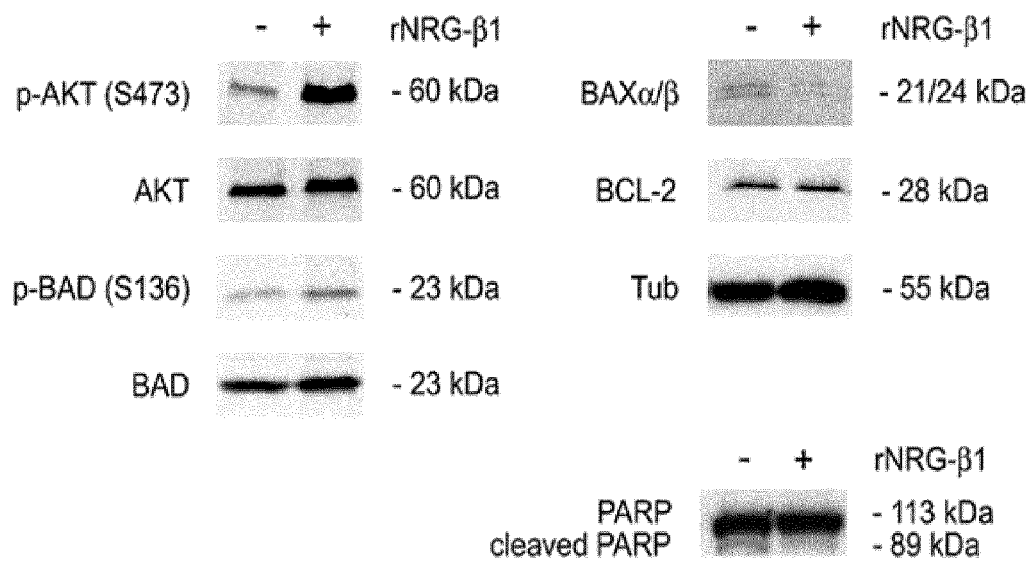
Figure 5:
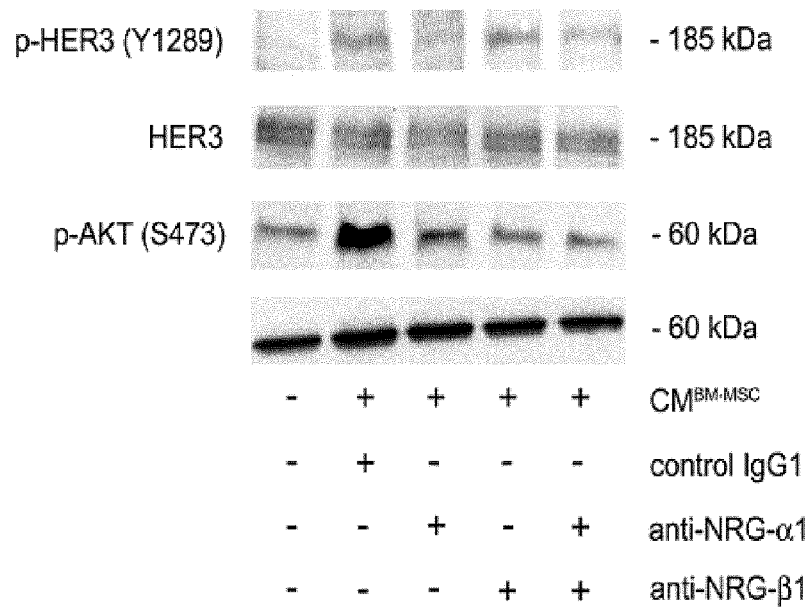

To quantify the potency of $CM^{BM-MSC}$ on HER3 tyrosine phosphorylation, we compared HCT-8/E11 cells treated with different concentrations of rNRG-β1 (FIG. 5A). Phosphorylation of HER3 was significant at 0.25 ng/ml rNRG-β1. Treatment with $CM^{BM-MSC}$ resulted in a HER3 phosphorylation equivalent to ±10 ng/ml rNRG-β1. In addition, rNRG-β1 (10 ng/ml) treatment induced HER2 activation in HCT-8/E11 cells, comparable to the effect of $CM^{BM-MSC}$ (FIG. 5B). Treatment of HCT-8/E11, HCT 116 and SW480 cells with rNRG-β1 (at 10 ng/ml) induced morphological changes (FIG. 5C) and invasion into a collagen matrix (P=0.049 for HCT-8/E11; P=0.007 for HCT 116; P=0.003 for SW480, chi-square test) (FIG. 5C). Addition of rNRG-β1 induced a dose-dependent increase in HCT-8/E11 cell number (P=0.473 at 0.1 ng/ml; P=0.087 at 1 ng/ml; P=0.002 at 10 ng/ml; two-way repeated measures ANOVA test) (FIG. 5D, left panel). rNRG-β1-treated HCT-8/E11 cells exhibited higher levels of S473 p-AKT and S136 p-BAD (FIG. 5E, upper left panel) and a reduced BAX/BCL-2 ratio (FIG. 5E, upper right panel). Furthermore, reduced PARP cleavage was observed in rNRG-β1-treated HCT 116 cells compared to controls (FIG. 5E, lower right panel).

Both biologically active NRG-α1 and NRG-β1 were released by BM-MSC in the culture medium, as shown by preincubation of $CM^{BM-MSC}$ with NRG-α1/β1 neutralizing antibodies, reversing the $CM^{BM-MSC}$-induced HER3 and AKT activation (FIG. 5F).

Functional Role of the BM-MSC-Mediated Paracrine NRG-1/HER3 Signaling

Figure 6:
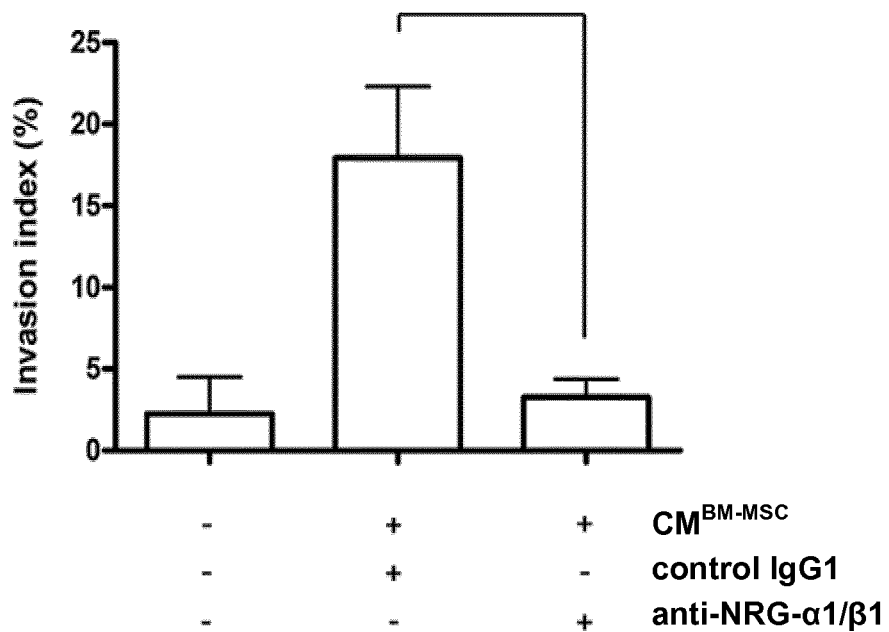
FIG. 6. Functional implication of paracrine $CM^{BM-MSC}$ and NRG-1-mediated activation of HER3/PI-3K/AKT in CRC cells. (A) Quantification of collagen invasion of HCT-8/E11 cells treated for 24 hours with $CM^{BM-MSC}$ supplemented with a combination of anti-NRG-α1/β1 neutralizing antibodies (2.5 μg/ml each) or the control IgG isotype. (B) Quantification of collagen invasion of HCT-8/E11 cells treated with $CM^{BM-MSC}$ for 24 hours after siHER1, 2 and 3 transfection. (C) Effect of drug or antibody treatments on $CM^{BM-MSC}$-induced morphological changes and collagen invasion. Cetuximab was used at 3 μM, lapatinib at 1 μM, and trastuzumab and pertuzumab at 25 μg/ml. Upper panels show phase-contrast images of HCT-8/E11 cells on collagen type I matrix and quantification of collagen invasion. Arrows indicate invasive extensions. Scalebar, 50 μm. Lower panels show F-actin images of HCT-8/E11 cells on collagen type I matrix and box and whisker plot showing quantification of the morphology with the factor shape. Scalebar, 20 μm. Median, quartiles and highest and lowest values are indicated on box and whisker plots. Factor shape was calculated as $(\text{perimeter})^2/(4\pi\text{area})$. P values were calculated using chi-square test (invasion index), and Mann-Whitney test (factor shape); statistically significant P values are indicated. (D) Quantification of collagen invasion of HCT-8/E11 cells treated with $CM^{BM-MSC}$ for 24 hours in combination with the PI3K inhibitors LY294002 and wortmannin and the AKT inhibitor GSK2141795 in concentrations as indicated. (E) Quantification of collagen invasion HCT-8/E11 cells treated with $CM^{BM-MSC}$ for 24 hours after siAKT transfection. The inset panel shows Western blot evaluation of AKT expression levels after siAKT transfection. Tubulin was used as a loading control. In (A-E) invasion indices are mean and standard error of at least three independent experiments. P values were calculated using the chi-square test; statistically significant P values are indicated.
Figure 6:
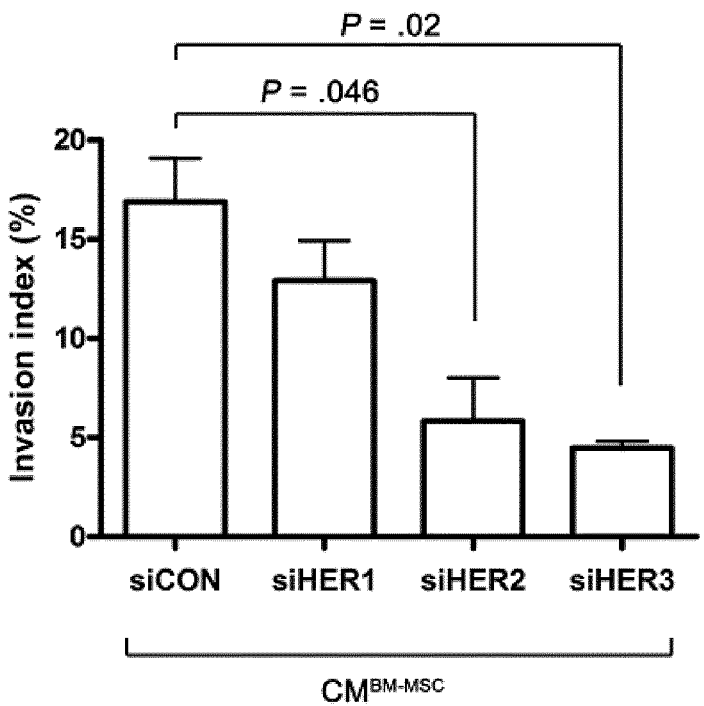
Figure 6:
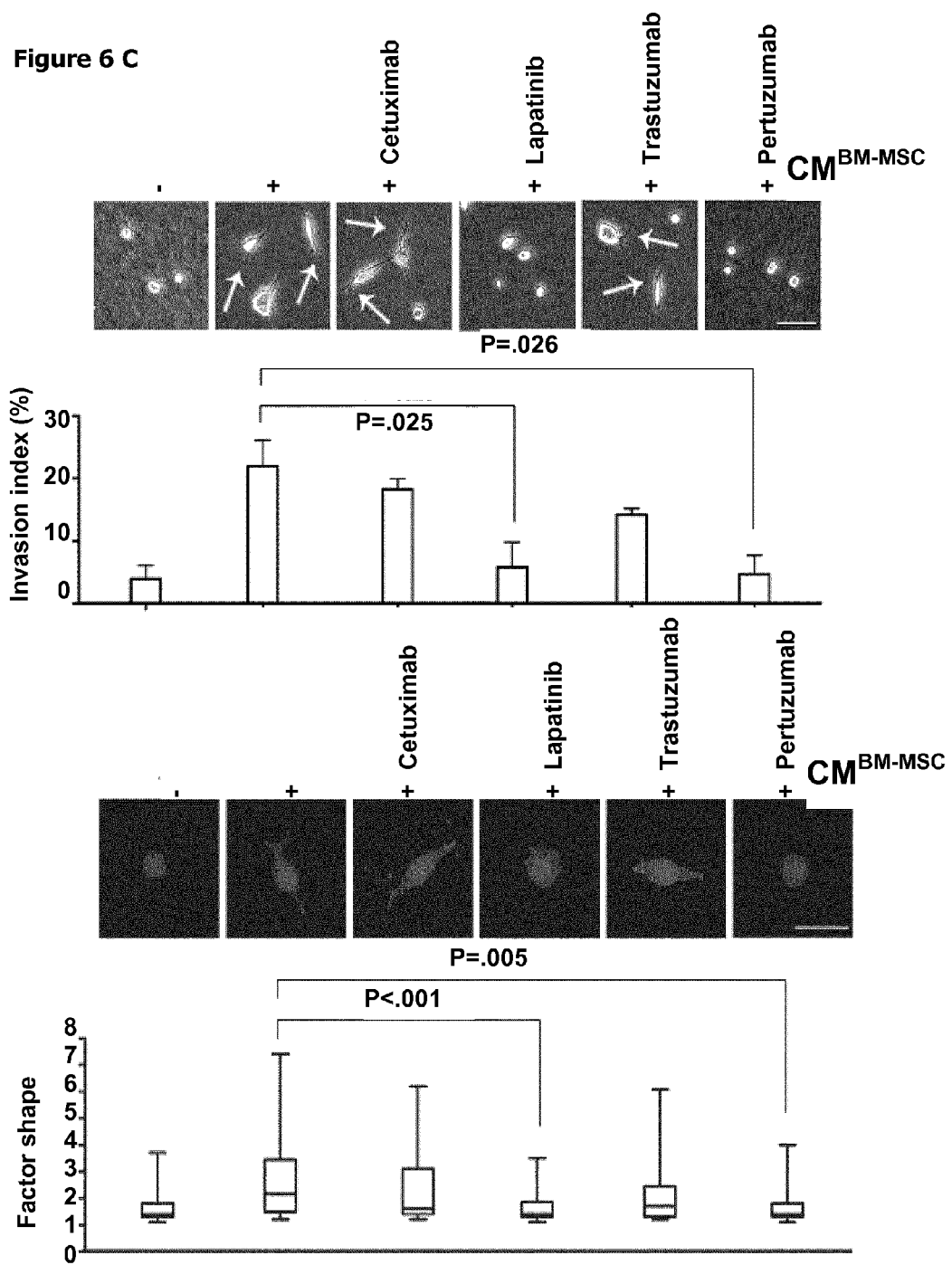
Figure 6:
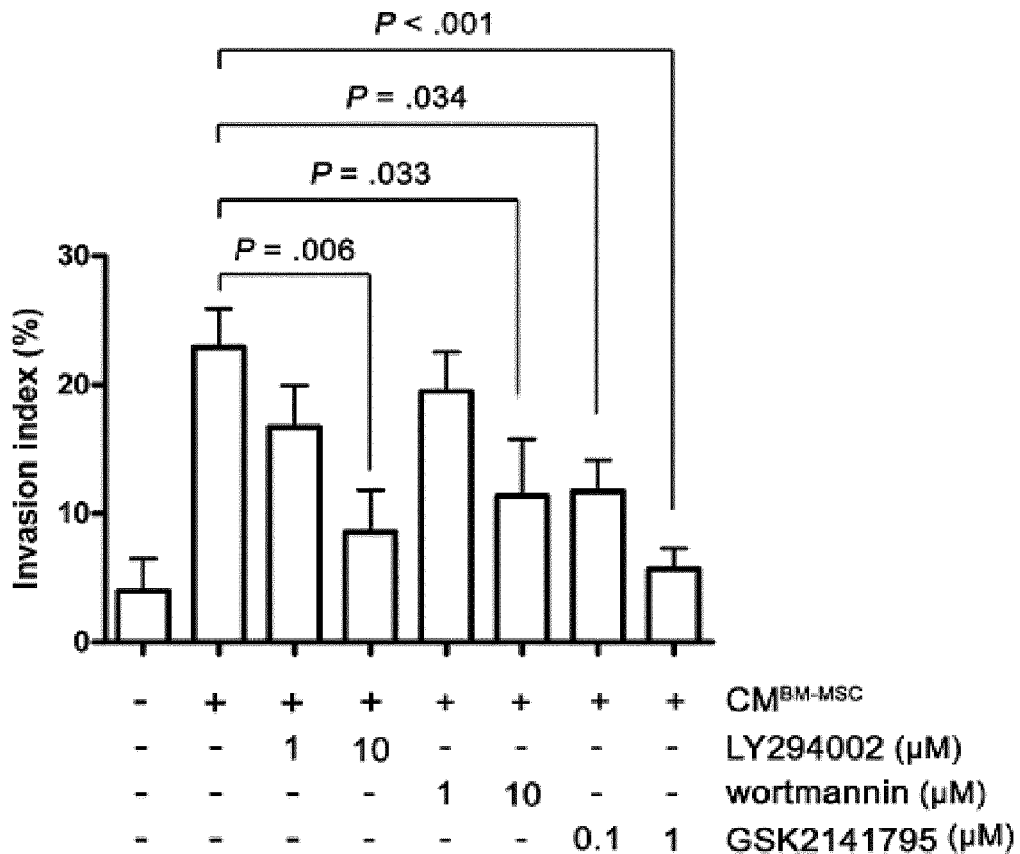
Figure 6:
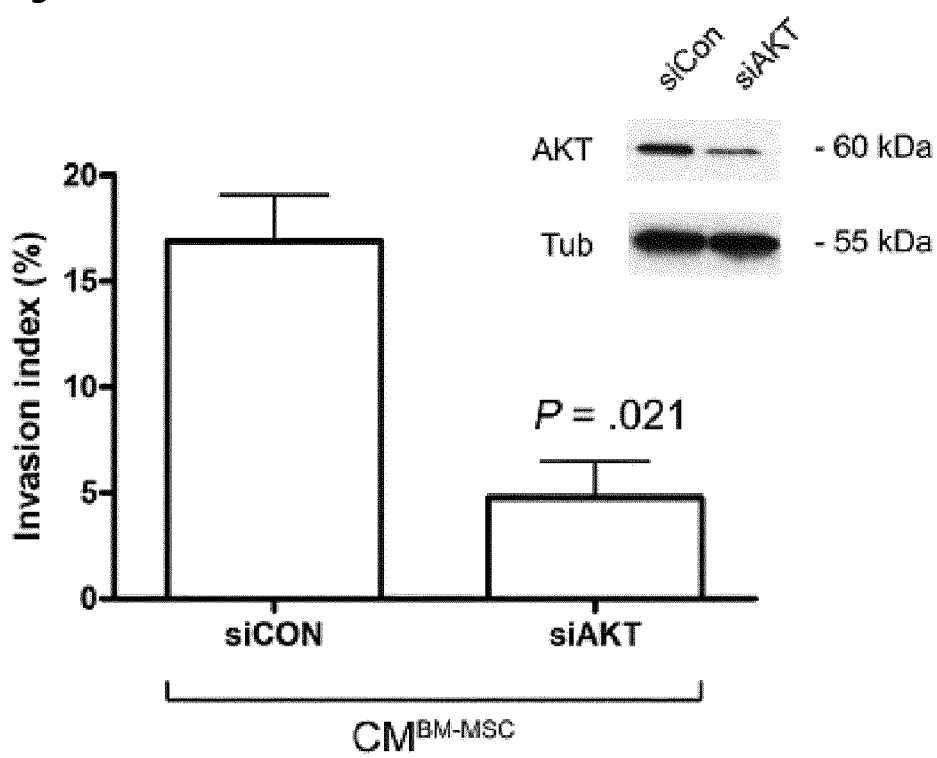

Depletion of NRG-1 in $CM^{BM-MSC}$ by NRG-α1/β1 neutralizing antibodies inhibited $CM^{BM-MSC}$-induced invasion by 82% whereas treatment with mouse IgG did not inhibit invasion (P=0.004, chi-square test) (FIG. 6A). Treatment with HER2 or HER3 siRNAs significantly reduced $CM^{BM-MSC}$-induced invasion by 66-74% (P=0.046 for siHER2, and P=0.02 for siHER3, chi-square test); a combination of both HER2 and HER3 siRNA did not show an additive response. HER1 siRNA did not significantly reduce $CM^{BM-MSC}$-induced invasion (FIG. 6B) (P=0.617, chi-square test). Lapatinib and pertuzumab blocked $CM^{BM-MSC}$-induced morphological and functional responses, as measured by the factor shape (P<0.001 for lapatinib and P=0.005 for pertuzumab, Mann-Whitney test), and invasion (P=0.025 for lapatinib and pertuzumab, chi-square test). No significant effects were observed with the other HER neutralizing antibodies and inhibitors on $CM^{BM-MSC}$-induced functional responses (for invasion index: P=0.824 for cetuximab, and P=0.374 for trastuzumab, chi-square test; for factor shape: P=0.333 for cetuximab, and P=0.153 for trastuzumab, Mann-Whitney test) (FIG. 6C). Next, we investigated the role of PI3K/AKT in $CM^{BM-MSC}$-induced invasion. Cancer cells were treated with the PI3K inhibitors LY294002 and wortmannin, the pan-AKT kinase inhibitor GSK2141795, and AKT siRNA (FIG. 6D). Drug concentrations that did not inhibit the basal invasion of HCT-8/E11, were able to block the $CM^{BM-MSC}$-induced invasion (P=0.006 for LY294002 (10 μM), P=0.033 for wortmannin (10 μM), P=0.034 for GSK2141795 (0.1 μM), and P<0.001 for GSK2141795 (1 μM), chi-square test). Transfection of HCT-8/E11 cells with AKT siRNA decreased $CM^{BM-MSC}$-induced invasion by 72% (P=0.021, chi-square test) (FIG. 6E).

Figure 7:
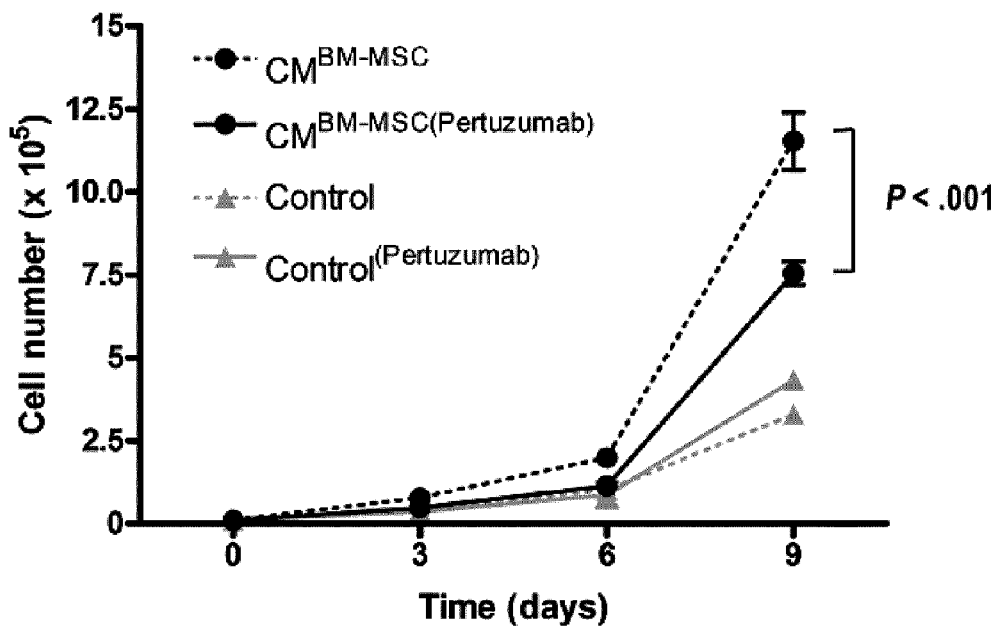
FIG. 7. Effect of pertuzumab on cells counts and tumor development in vivo. (A) Effect of pertuzumab (25 μg/ml) and vehicle only on $CM^{BM-MSC}$-induced total number of viable HCT-8/E11 cells. (B) Tumor volume and tumor weight (C) of s.c. xenografts derived from $10^6$ HCT-8/E11 cells with or without $2\cdot10^6$ BM-MSC. After one week, mice were either treated with vehicle only or with pertuzumab (600 μg/mouse) injected i.p. three times a week. Tumor volume was assessed weekly by measurement of the external diameter. Mice were killed at variable time points (i.e., the ethical endpoint that limits tumor volume formation (+/−1 $cm^3$). Tumor weight was assessed after surgical resection. In (A), (B) and (C), results are expressed as mean and standard error from 10 xenografts from two independent experiments. In (A) and (B), P values were calculated using two-way repeated measures ANOVA test. In (C), P values were calculated using Mann-Whitney test; statistically significant P values are indicated. (D) Ki67 labelling in resected xenografts derived from HCT-8/E11+BM-MSC within weeks of vehicle only or pertuzumab treatment. The mean number of Ki67-positive cells; and their respective standard error calculated from 12 images of two primary tumors is indicated. Scale bar, 100 μm; inset scale bar, 50 μm.
Figure 7:
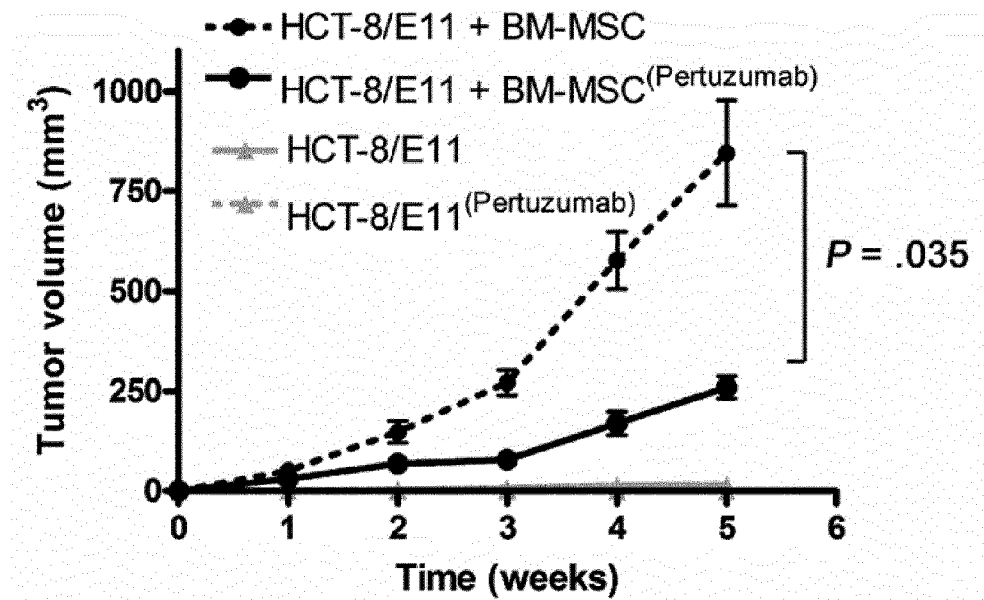
Figure 7:
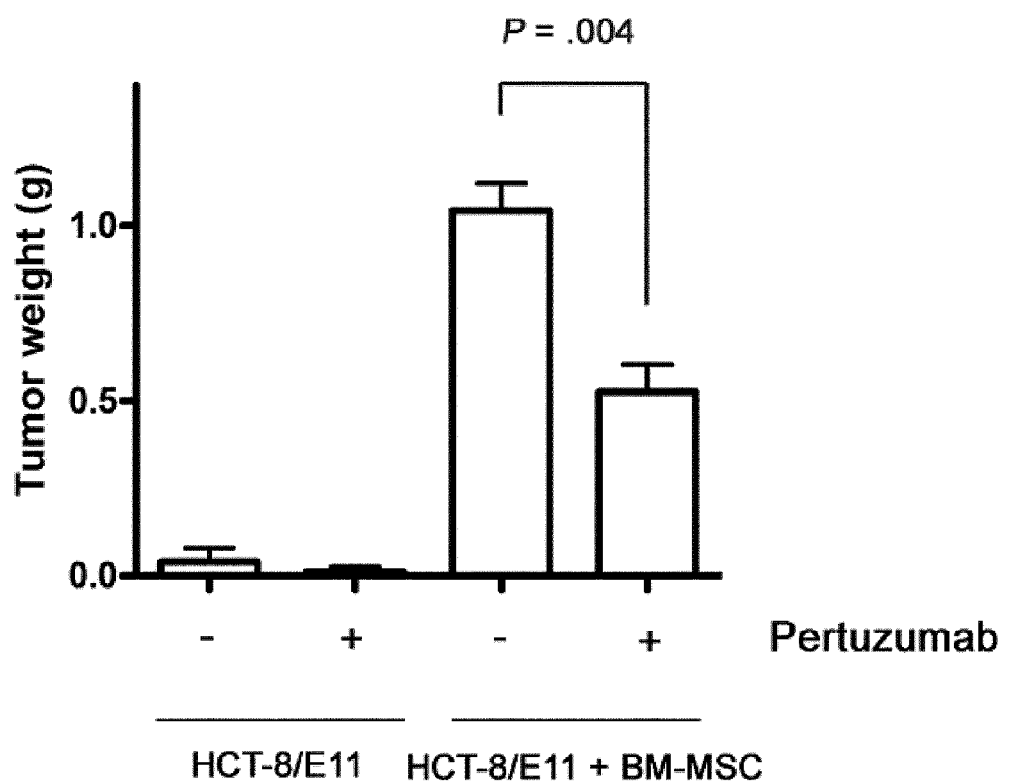
Figure 7:
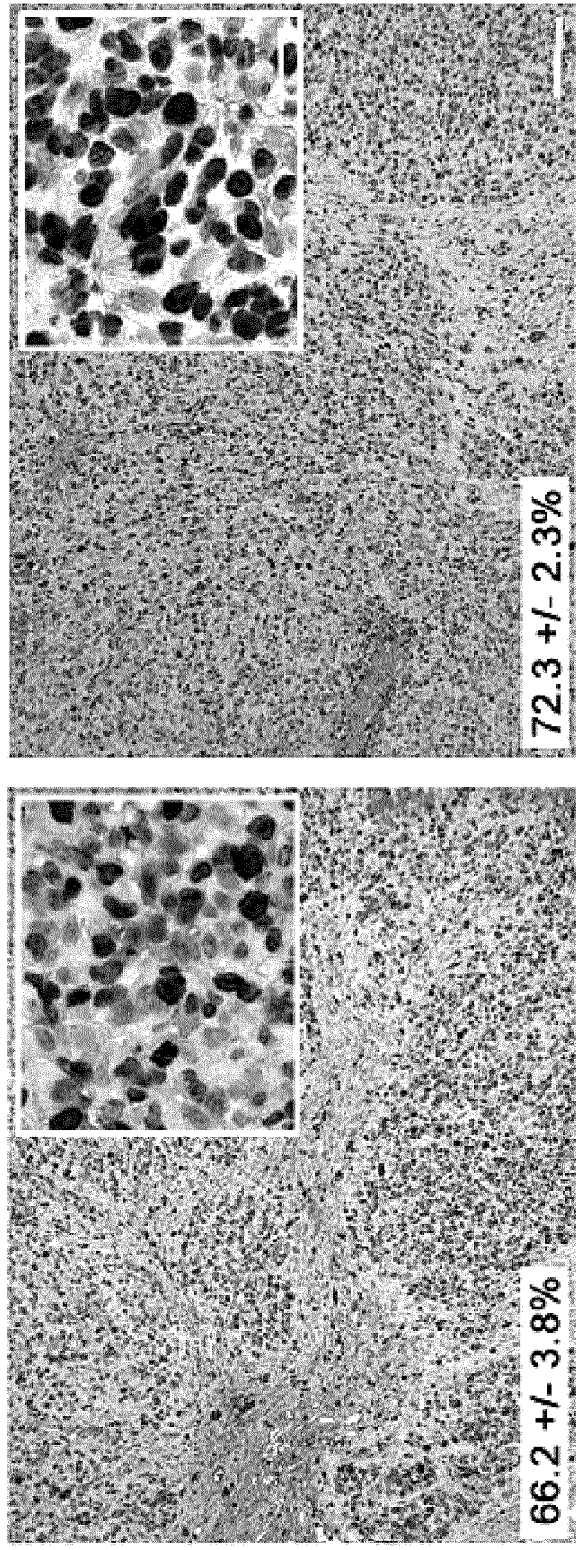

We further examined whether HER2-HER3 dimerization and signaling in HCT-8/E11 cells play an essential role in BM-MSC-enhanced survival and tumorigenesis. Pertuzumab significantly decreased $CM^{BM-MSC}$-induced CRC cell survival, as shown in FIG. 7A for HCT-8/E11 cells (P<0.001, two-way repeated measures ANOVA test), with no statistically significant effect of pertuzumab under control conditions (P=0.715, two-way repeated measures ANOVA). In agreement, i.p. injections of pertuzumab (600 μg/mouse) significantly delayed BM-MSC-enhanced tumorigenesis of HCT-8/E11 cells, as demonstrated by reduced tumor volume (P=0.035, two-way repeated measures ANOVA test) (FIG. 7B) and decreased tumor weight (P=0.004, Mann-Whitney test). Vehicle treated mice did not show these responses (FIG. 7C). In viable areas, pertuzumab treatment did not significantly affect the Ki67 proliferation index (difference=5.2, 95% CI of the difference=−4.8 to 15.2, P=0.276, Student's t-test) (FIG. 7D). These data indicate a role for HER2-HER3-mediated survival signals in BM-MSC-induced tumorigenesis of HCT-8/E11 cells.

Expression of tNRG-1 in Human CRCs

Figure 8:
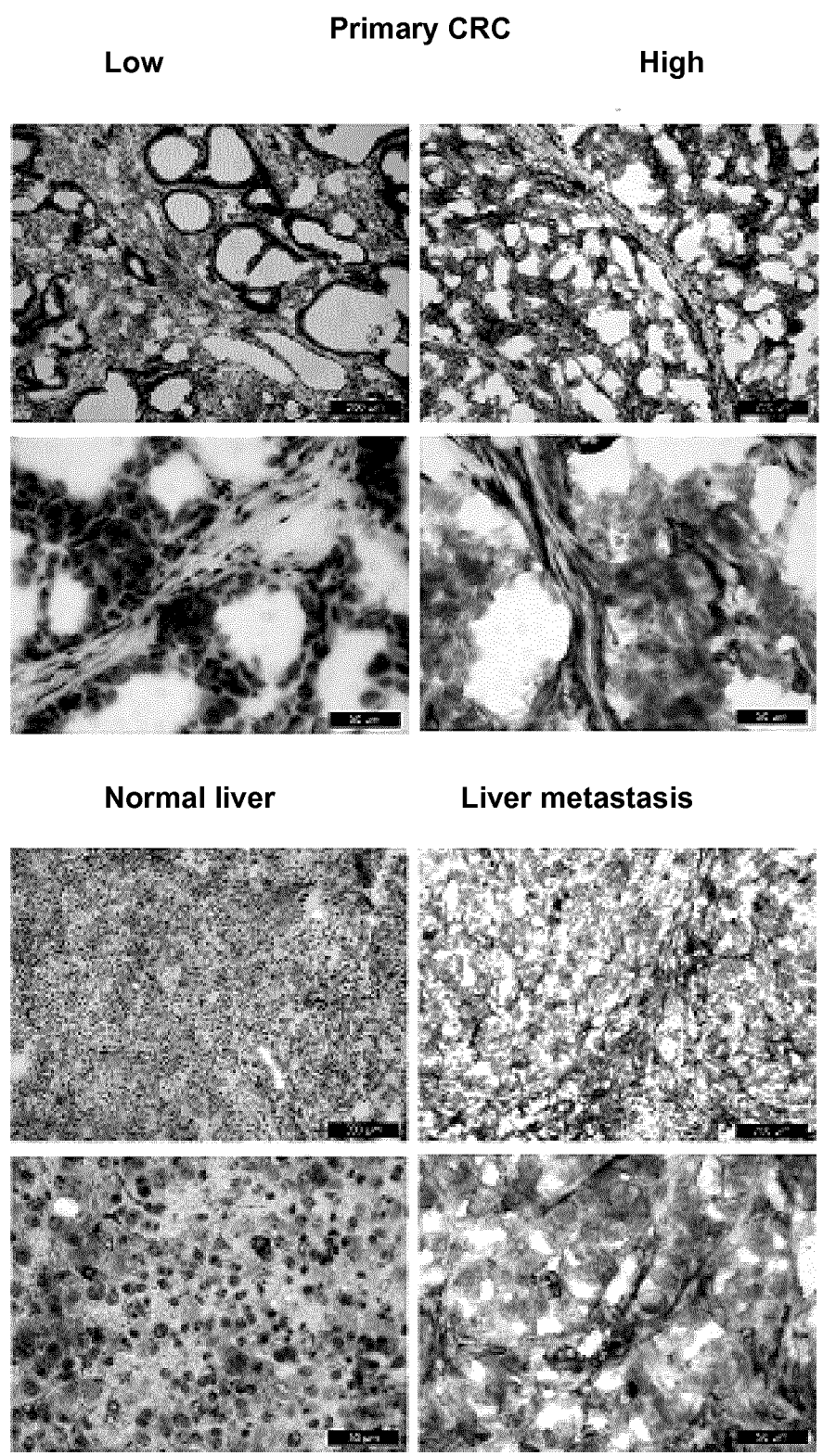
FIG. 8. Expression of tNRG-1 in primary human CRCs. A) Representative tNRG-1 stained primary human CRC samples that illustrate IHC scores of low and high expression (upper panel) and normal liver and liver metastasis sample (lower panel). (B) Expression levels of tNRG-1 in normal and CRC tissue and associations of tNRG-1 IHC scores with invasion depth, UICC stage, and 5-year PFS. Comparisons of tNRG-1 expression between normal versus tumor tissue and tNRG-1 association with 5-year PFS were performed using chi-square test. tNRG-1 association with clinicopathological parameters was analysed by the chi-square test for trend. (C) Western blot analysis of tNRG-1 precursor expression in 3 matched pairs of primary mesenchymal cells from tumor tissue (T) or adjacent normal tissue (N). (D) Western blot evaluation of Y1289 p-HER3 and S473 p-AKT and total HER3 and AKT expression levels in HCT-8/E11 treated with CM from primary mesenchymal cells from tumor tissue (T) and adjacent normal tissue (N) obtained from patient 1 or (E) treated with interstitial fluid from CRC tissue (T) and adjacent normal colorectal tissue (N) from the same patient. (F) Quantification of collagen invasion of HCT-8/E11 cells treated for 24 hours with $CM^{T-MC}$ supplemented with pertuzumab (25 µg/ml). Invasion indices are mean and standard error of at least three independent experiments. P values were calculated using the chi-square test; statistically significant P values are indicated. (G) Quantification of the total number of viable CRC cells at different time intervals treated with $CM^{T-MC}$ under serum-free conditions. Pertuzumab was used at 25 µg/ml. Results are presented as mean and standard error from three independent experiments. P values were calculated using two-way repeated measures ANOVA test; statistically significant P values are indicated.
Figure 8:
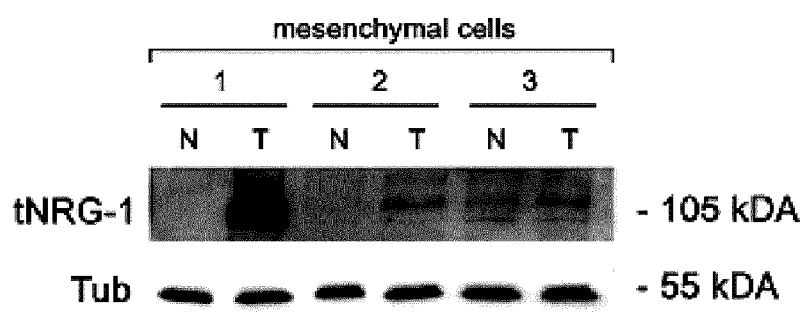
Figure 8:
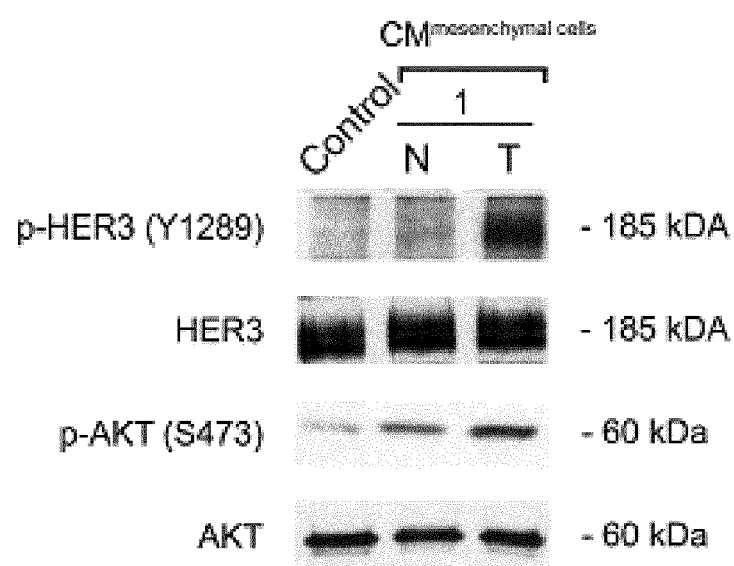
Figure 8:
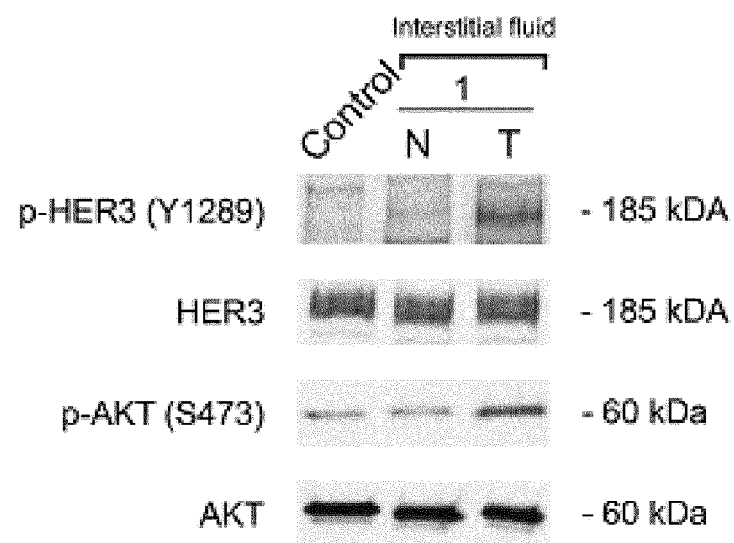
Figure 8:
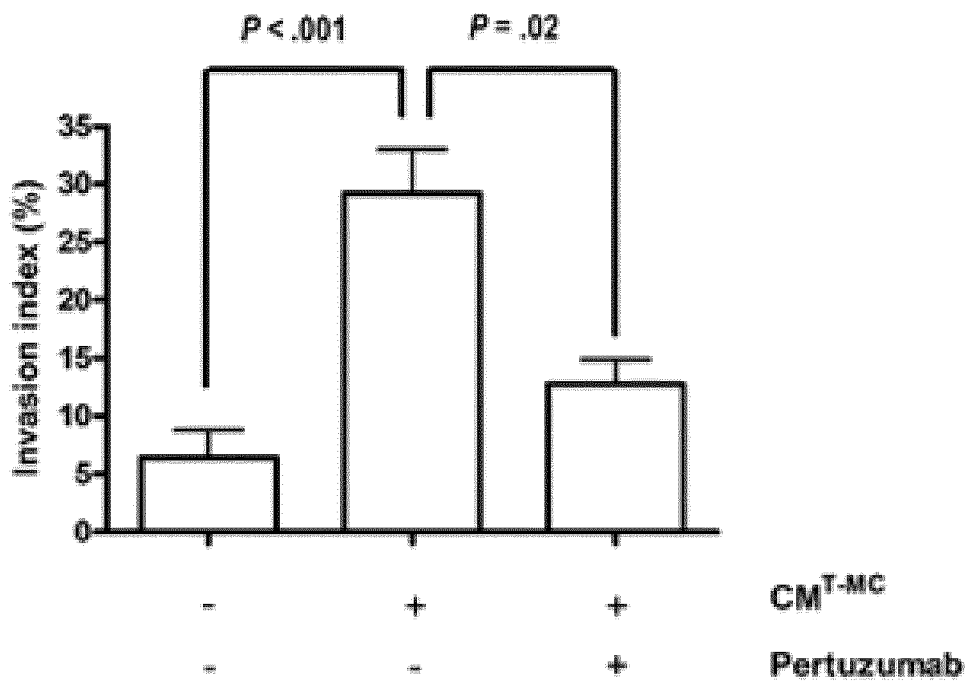
Figure 8:
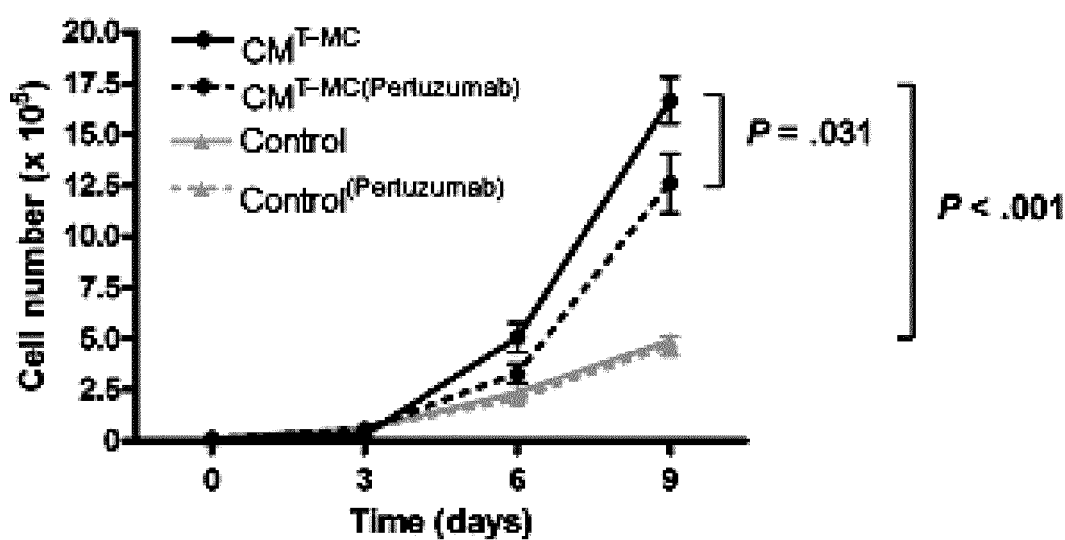
Figure 13:
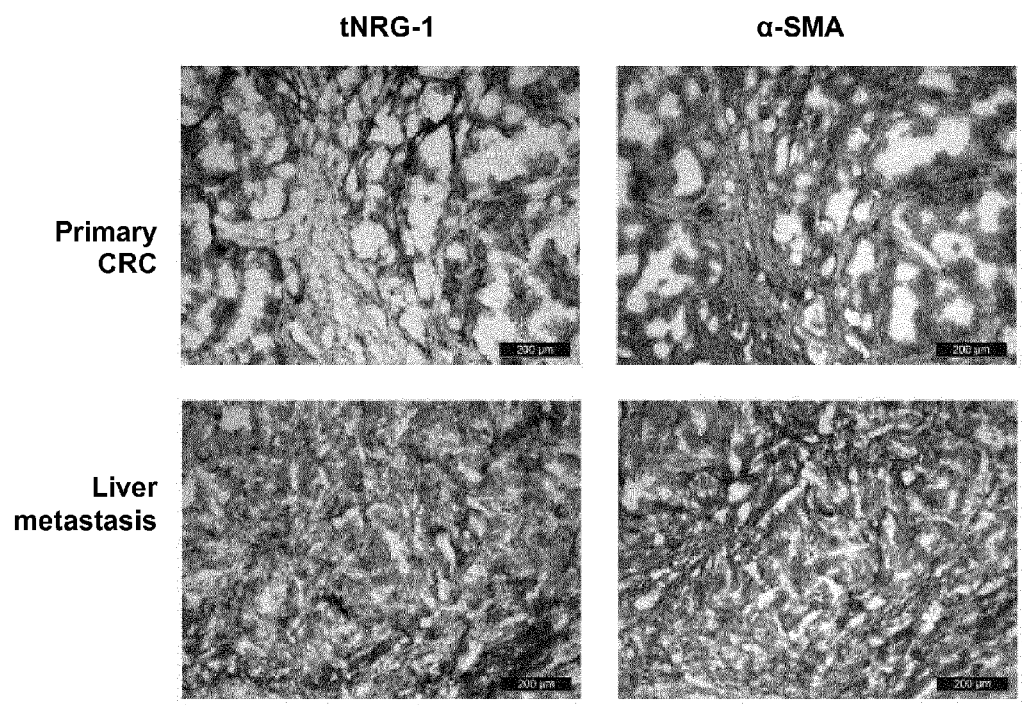
FIG. 13. tNRG-1 expressing mesenchymal cells are α-SMA-positive. Representative examples of tNRG-1 (left panel) and α-SMA (right panel) IHC staining in primary CRC (upper panel) and liver metastasis (lower panel).
Figure 14:
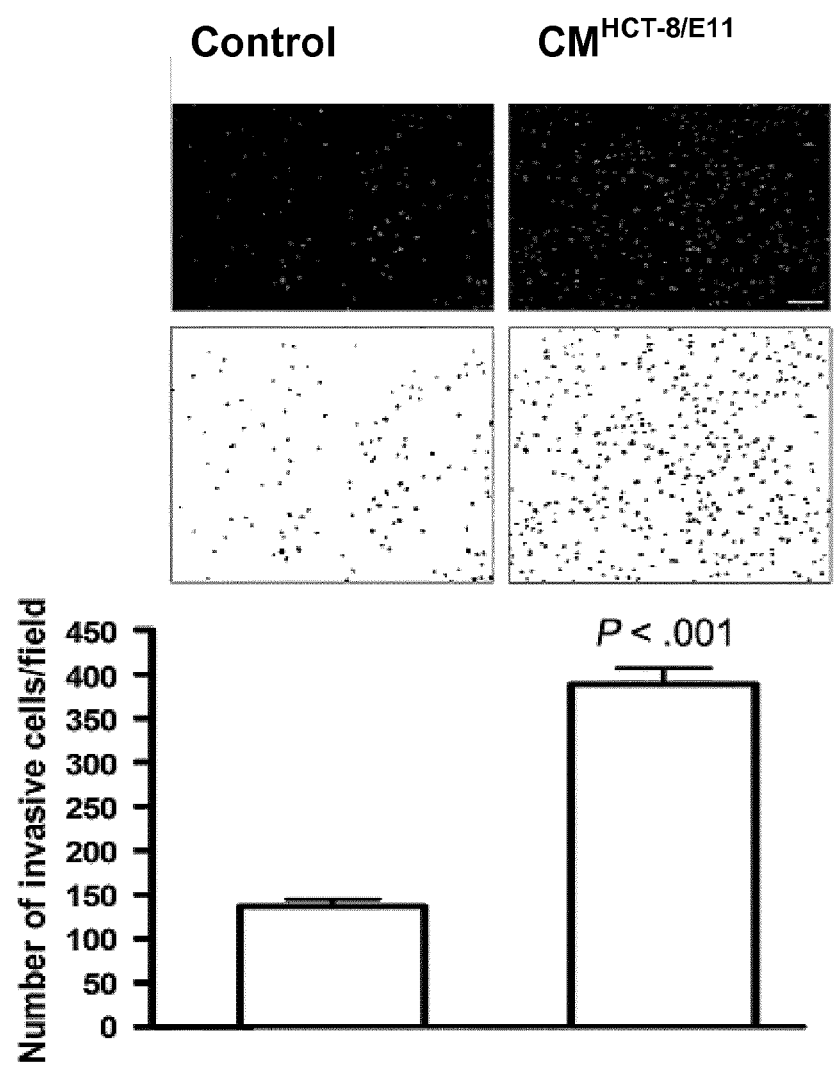
FIG. 14. $CM^{HCT-8/E11}$ stimulates invasion of BM-MSC through a Matrigel membrane. $2 \times 10^4$ BM-MSC were seeded upon a Matrigel coated filter with control medium or $CM^{HCT-8/E11}$ as chemoattractant in the lower compartment. Cells on the lower surface of the membrane were stained with DAPI. Scale bar, 100 µm (upper panel). Fluorescent images were converted to binary images (middle panel) and invasive cells were counted using Image J analysis (lower panel). Results are expressed as mean and standard error from three independent experiments. P values were calculated using Student's t-test; statistically significant P values are indicated.

We studied the expression of tNRG-1 in primary CRCs (n=54), adjacent normal colorectal tissues (n=4), liver metastases (n=3) and adjacent normal liver tissues (n=3) by IHC (FIGS. 8A and B, and Table 2). 41 out of 54 of CRCs (76%) and 3 out of 3 liver metastases (100%) demonstrated high stromal tNRG-1 expression. On the contrary, tNRG-1 expression was negative in the stroma of adjacent normal tissue (0/4; 0%) (P=0.006; chi-square test), and in the epithelial cancer cells in most CRC specimens (47/54, 87%). Stromal tNRG-1 expression was confined to the spindle-shaped mesenchymal cells around the neoplastic tubules or glands (FIG. 8A, upper panel), especially at the invasion front. The frequency of tNRG-1 expression by mesenchymal cells increased markedly from normal to tumor tissue. Furthermore, we observed a gradient in the pattern of tNRG-1 staining in the primary tumors with prominent expression in the stroma directly surrounding the cancer cells and minimal or absent expression in the distal part of the peritumoral stroma. In contrast, α-SMA, a marker for activated tumo-associated mesenchymal cells or myofibroblasts, was expressed in almost all of the stromal cells in the primary tumors and liver metastases (FIG. 13). Invasion depth and UICC stage were significantly associated with stromal tNRG-1 expression (P=0.04 and P=0.005; chi-square test for trend). Moreover, high stromal tNRG-1 expression was significantly related to a decreased 5-year PFS (P=0.002; chi-square test) (FIG. 8B).

To further confirm our data, we collected 3 additional pairs of CRC tissue and adjacent normal colorectal tissue. Mesenchymal cells associated with the tumor (T-MC) and adjacent normal tissue (N-MC) were isolated. T-MC were morphologically similar to BM-MSC (FIG. 9A). Flow cytometry of T-MC revealed a similar expression pattern of antigens characteristic of BM-MSC (FIG. 9B) (61). A marked osteogenic but limited adipogenic differentiation was inducible in T-MC (FIG. 9C), suggesting that T-MC maintain traits of multipotency. Western blot analysis from these cultured mesenchymal cells revealed tNRG-1 expression in all 3 tumor cultures and in 1 out of 3 normal cultures (FIG. 8C). In agreement, CM from T-MC obtained from the first patient with the strongest tNRG-1 expression level was more potent in inducing HER3 and AKT activation in HCT-8/E11 cells compared to CM from N-MC (FIG. 8D). Additionally, we collected interstitial fluids from tumor tissue and adjacent normal tissue (44) and found that the tumor interstitial fluid was able to activate HER3/AKT in cultured HCT-8/E11 CRC cells (FIG. 8E), suggesting the release of functionally active NRG-1 into the extracellular space. We next tested whether $CM^{T-MC}$-induced HER3 activation played a functional role in stimulating HCT-8/E11 invasion and cell number. We found a 5-fold increase in the invasion index of HCT-8/E11 when exposed to $CM^{T-MC}$ compared to controls (P<0.001, chi-square test). Treatment with pertuzumab partly inhibited $CM^{T-MC}$-increased invasion (P=0.02, chi-square test), whereas cetuximab failed to mimic this effect (FIG. 8F). In addition, the growth of HCT-8/E11 cells treated with $CM^{T-MC}$ was significantly increased (P<0.001, two-way repeated measures ANOVA test). This trophic effect was blocked by pertuzumab (P=0.014, two-way repeated measures ANOVA test) (FIG. 8G).

TABLE 2 tNRG-1 association with clinicopathological characteristics and 5-year PFS in CRC patients

|   | Age | Sex | Localisation | TNM | UICC stage | 5-year PFS | Cause of progression | tNRG-1 IHC score |
|---|-----|-----|--------------|-----|------------|------------|----------------------|------------------|
| 1 | 86 | M | Sigmoid | $T_2N_0M_0$ | I | Yes | | Low |
| 2 | 55 | M | Colon descendens | $T_2N_0M_0$ | I | Yes | | Low |
| 3 | 65 | M | Sigmoid | $T_3N_2M_0$ | III | Yes | | Low |
| 4 | 73 | F | Sigmoid | $T_3N_2M_0$ | III | Unknown | | Low |
| 5 | 76 | F | Cecum | $T_3N_0M_0$ | II | Yes | | Low |
| 6 | 73 | F | Colon descendens | $T_2N_0M_0$ | I | Yes | | Low |
| 7 | 61 | F | Sigmoid | $T_3N_0M_0$ | II | Yes | | Low |
| 8 | 61 | M | Sigmoid | $T_4N_1M_0$ | III | No | Local recurrence | Low |
| 9 | 59 | F | Right hemicolon | $T_2N_0M_0$ | I | Yes | | Low |
| 10 | 87 | F | Colon ascendens | $T_3N_1M_0$ | III | No | Cerebral metastasis | Low |
| 11 | 55 | M | Sigmoid | $T_3N_0M_0$ | II | Yes | | Low |
| 12 | 66 | F | Cecum | $T_1N_0M_0$ | I | Unknown | | low |

TABLE 2-continued tNRG-1 association with clinicopathological characteristics and 5-year PFS in CRC patients

|    | Age | Sex | Localisation | TNM | UICC stage | 5-year PFS | Cause of progression | tNRG-1 IHC score |
|----|-----|-----|--------------|-----|------------|------------|---------------------|------------------|
| 13 | 80  | F   | Sigmoid      | $T_2N_0M_0$ | I   | Unknown |  | Low |
| 14 | 86  | M   | Colon transversum | $T_2N_0M_0$ | I | Unknown |  | High |
| 15 | 81  | M   | Rectum | $T_3N_1M_0$ | III | No | Lung and bone metastasis | High |
| 16 | 76  | M   | Cecum | $T_4N_2M_0$ | III | No | Peritoneal metastasis | High |
| 17 | 72  | M   | Cecum | $T_xN_xM_1$ | IV | No | Metastatic disease | High |
| 18 | 65  | F   | Cecum | $T_3N_0M_0$ | II | Yes |  | High |
| 19 | 73  | M   | Sigmoid | $T_3N_0M_0$ | II | Yes |  | High |
| 20 | 88  | M   | Low rectum | $T_3N_0M_0$ | II | Yes |  | High |
| 21 | 54  | F   | Right hemicolon | $T_3N_0M_0$ | II | Unknown |  | High |
| 22 | 80  | F   | Cecum | $T_3N_0M_0$ | II | Unknown |  | High |
| 23 | 94  | F   | Colon ascendens | $T_3N_0M_0$ | II | Unknown |  | High |
| 24 | 79  | M   | Low rectum | $T_1N_0M_0$ | I | Unknown |  | High |
| 25 | 74  | F   | Rectum | $T_3N_2M_0$ | III | Yes |  | High |
| 26 | 82  | M   | Colon transversum | $T_2N_0M_0$ | I | Unknown |  | High |
| 27 | 79  | M   | Sigmoid | $T_3N_2M_0$ | III | Unknown |  | High |
| 28 | 54  | M   | Cecum | $T_4N_2M_0$ | III | No | Bone metastasis | High |
| 29 | 73  | F   | Sigmoid | $T_2N_0M_0$ | I | Unknown |  | High |
| 30 | 69  | M   | Rectum | $T_3N_1M_0$ | III | Unknown |  | High |
| 31 | 85  | F   | Sigmoid | $T_3N_0M_0$ | II | Unknown |  | High |
| 32 | 65  | F   | Right hemicolon | $T_4N_0M_0$ | II | No | Local recurrence | High |
| 33 | 65  | F   | Ileum | $T_4N_2M_0$ | III | Unknown |  | High |
| 34 | 69  | F   | Left hemicolon | $T_xN_xM_1$ | IV | No | Metastatic disease | High |
| 35 | 86  | M   | Right hemicolon | $T_3N_0M_0$ | II | Unknown |  | High |
| 36 | 71  | M   | Hepatic corner | $T_3N_0M_0$ | II | Yes |  | High |
| 37 | 66  | M   | Sigmoid | $T_4N_1M_0$ | III | Unknown |  | High |
| 38 | 75  | M   | Colon transversum | $T_4N_1M_0$ | III | No | Recurrence small intestine | High |
| 39 | 55  | F   | Left hemicolon | $T_xN_xM_1$ | IV | No | Metastatic disease | High |
| 40 | 72  | F   | Sigmoid | $T_2N_1M_0$ | III | No | Liver metastasis | High |
| 41 | 80  | M   | Left hemicolon | $T_3N_1M_0$ | III | No | Liver metastasis | High |
| 42 | 53  | F   | Left hemicolon | $T_4N_1M_0$ | III | No | Lung metastasis | High |
| 43 | 69  | F   | Sigmoid | $T_xN_xM_1$ | IV | No | Metastatic disease | High |
| 44 | 74  | M   | Hepatic corner | $T_xN_xM_1$ | IV | No | Metastatic disease | High |
| 45 | 61  | M   | Rectum | $T_xN_xM_1$ | IV | No | Metastatic disease | High |
| 46 | 85  | F   | Low rectum | $T_3N_2M_0$ | III | No | Local recurrence and lung metastasis | High |
| 47 | 75  | M   | Low rectum | $T_3N_0M_0$ | II | No | Local recurrence | High |
| 48 | 67  | F   | Sigmoid | $T_3N_2M_0$ | III | No | Liver metastasis | High |
| 49 | 43  | F   | Unknown | $T_xN_xM_1$ | IV | No | Metastatic disease | High |
| 50 | 41  | M   | Right hemicolon | $T_3N_2M_0$ | III | No | Local recurrence | High |
| 51 | 70  | M   | Unknown | $T_xN_xM_1$ | IV | No | Metastatic disease | High |
| 52 | 64  | F   | Sigmoid | $T_3N_0M_0$ | II | No | Liver and lung metastasis | High |
| 53 | 69  | F   | Sigmoid | $T_3N_1M_0$ | III | No | Lung and bone metastasis | High |
| 54 | 82  | F   | Cecum | $T_3N_1M_0$ | III | Yes |  | High |

REFERENCES

1. Siegel R, Ward E, Brawley O, Jemal A. Cancer statistics, 2011: the impact of eliminating socioeconomic and racial disparities on premature cancer deaths. *CA Cancer J Clin.* 2011; 61(4):212-236.
2. De Wever O, Mareel M. Role of tissue stroma in cancer cell invasion. *J Pathol.* 2003; 200(4):429-447.
3. Caplan A I. Adult mesenchymal stem cells for tissue engineering versus regenerative medicine. *J Cell Physiol.* 2007; 213(2):341-347.
4. Menon L G, Picinich S, Koneru R, Gao H, Lin S Y, Koneru M, et al. Differential Gene Expression Associated with Migration of Mesenchymal Stem Cells to Conditioned Medium from Tumor Cells or Bone Marrow Cells. *Stem Cells.* 2007; 25(2):520-528.
5. Hung S-C, Deng W-P, Yang W K, Liu R-S, Lee C-C, Su T-C, et al. Mesenchymal stem cell targeting of microscopic tumors and tumor stroma development monitored by non-invasive in vivo positron emission tomography imaging. *Clin Cancer Res.* 2005; 11(21):7749-7756.
6. Karnoub A E, Dash A B, Vo A P, Sullivan A, Brooks M W, Bell G W, et al. Mesenchymal stem cells within tumour stroma promote breast cancer metastasis. *Nature.* 2007; 449(7162):557-563.
7. Studeny M, Marini F C, Dembinski J L, Zompetta C, Cabreira-Hansen M, Bekele B N, et al. Mesenchymal stem cells: Potential precursors for tumor stroma and targeted-delivery vehicles for anticancer agents. *J Natl Cancer Inst.* 2004; 96(21):1593-1603.
8. De Boeck A, Narine K, De Neve W, Mareel M, Bracke M, De Wever O. Resident and bone marrow-derived mesenchymal stem cells in head and neck squamous cell carcinoma. *Oral Oncol.* 2010; 46(5):336-342.
9. De Wever O, Nguyen Q D, Van Hoorde L, Bracke M, Bruyneel E, Gespach C, et al. Tenascin-C and SF/HGF produced by myofibroblasts in vitro provide convergent pro-invasive signals to human colon cancer cells through RhoA and Rac. *FASEB J.* 2004; 18(9):1016-1018.
10. De Wever O, Demetter P, Mareel M, Bracke M. Stromal myofibroblasts are drivers of invasive cancer growth. *Int J Cancer.* 2008; 123(10):2229-2238.
11. Haddow A, George Klein S W, Alexander H. Molecular Repair, Wound Healing, And Carcinogenesis: Tumor Production A Possible Overhealing? In: *Adv Cancer Res*: Academic Press; 1973:181-234.
12. Flier J S, Underhill L H, Dvorak H F. Tumors: Wounds That Do Not Heal. *N Engl J Med.* 1986; 315(26):1650-1659.

13. Mayer A, Takimoto M, Fritz E, Schellander G, Kofler K, Ludwig H. The prognostic significance of proliferating cell nuclear antigen, epidermal growth factor receptor, and mdr gene expression in colorectal cancer. *Cancer.* 1993; 71(8): 2454-2460.
14. Hemming A W, Davis N L, Kluftinger A, Robinson B, Quenville N F, Liseman B, et al. Prognostic markers of colorectal cancer: an evaluation of DNA content, epidermal growth factor receptor, and Ki-67. *J Surg Oncol.* 1992; 51(3):147-152.
15. Grivas P D, Antonacopoulou A, Tzelepi V, Sotiropoulou-Bonikou G, Kefalopoulou Z, Papavassiliou A G, et al. HER-3 in colorectal tumourigenesis: from mRNA levels through protein status to clinicopathologic relationships. *Eur J Cancer.* 2007; 43(17):2602-2611.
16. Kapitanovic S, Radosevic S, Slade N, Kapitanovic M, Andelinovic S, Ferencic Z, et al. Expression of erbB-3 protein in colorectal adenocarcinoma: correlation with poor survival. *J Cancer Res Clin Oncol.* 2000; 126(4):205-211.
17. Ho-Pun-Cheung A, Assenat E, Bascoul-Mollevi C, Bibeau F, Boissière-Michot F, Cellier D, et al. EGFR and HER3 mRNA expression levels predict distant metastases in locally advanced rectal cancer. *Int J Cancer.* 2011; 128 (12):2938-2946.
18. Jones J T, Akita R W, Sliwkowski M X. Binding specificities and affinities of egf domains for ErbB receptors. *FEBS Lett.* 1999; 447(2-3):227-231.
19. Carraway K L, 3rd, Weber J L, Unger M J, Ledesma J, Yu N, Gassmann M, et al. Neuregulin-2, a new ligand of ErbB3/ErbB4-receptor tyrosine kinases. *Nature.* 1997; 387(6632):512-516.
20. Crovello C S, Lai C, Cantley L C, Carraway K L, 3rd. Differential signaling by the epidermal growth factor-like growth factors neuregulin-1 and neuregulin-2. *J Biol Chem.* 1998; 273(41):26954-26961.
21. Massague J, Pandiella A. Membrane-anchored growth factors. *Annu Rev Biochem.* 1993; 62:515-541.
22. Montero J C, Yuste L, Diaz-Rodriguez E, Esparis-Ogando A, Pandiella A. Differential shedding of transmembrane neuregulin isoforms by the tumor necrosis factor-alpha-converting enzyme. *Mol Cell Neurosci.* 2000; 16(5):631-648.
23. Stove C, Boterberg T, Van Marck V, Mareel M, Bracke M. Bowes melanoma cells secrete heregulin, which can promote aggregation and counteract invasion of human mammary cancer cells. *Int J Cancer.* 2005; 114(4):572-578.
24. Sheng Q, Liu X, Fleming E, Yuan K, Piao H, Chen J, et al. An Activated ErbB3/NRG1 Autocrine Loop Supports In Vivo Proliferation in Ovarian Cancer Cells. *Cancer Cell.* 2010; 17(3):298-310.
25. Noguchi H, Sakamoto C, Wada K, Akamatsu T, Uchida T, Tatsuguchi A, et al. Expression of heregulin alpha, erbB2, and erbB3 and their influences on proliferation of gastric epithelial cells. *Gastroenterology.* 1999; 117(5):1119-1127.
26. de Alava E, Ocaña A, Abad M, Montero J C, Esparis-Ogando A, Rodríguez C A, et al. Neuregulin Expression Modulates Clinical Response to Trastuzumab in Patients With Metastatic Breast Cancer. *J Clin Oncol.* 2007; 25(19):2656-2663.
27. Nagata K, Wada K, Tatsuguchi A, Futagami S, Gudis K, Miyake K, et al. Heregulin-alpha and heregulin-beta expression is linked to a COX-2-PGE2 pathway in human gastric fibroblasts. *Am J Physiol Gastrointest Liver Physiol.* 2006; 290(6):G1243-1251.
28. Eschrich S, Yang I, Bloom G, Kwong K Y, Boulware D, Cantor A, et al. Molecular staging for survival prediction of colorectal cancer patients. *J Clin Oncol.* 2005; 23(15):3526-3535.
29. Yoshioka T, Nishikawa Y, Ito R, Kawamata M, Doi Y, Yamamoto Y, et al. Significance of integrin alphavbeta5 and erbB3 in enhanced cell migration and liver metastasis of colon carcinomas stimulated by hepatocyte-derived heregulin. *Cancer Sci.* 2010; 101(9):2011-2018.
30. Liles J S, Arnoletti J P, Kossenkov A V, Mikhaylina A, Frost A R, Kulesza P, et al. Targeting ErbB3-mediated stromal-epithelial interactions in pancreatic ductal adenocarcinoma. *Br J Cancer.* 105(4):523-533.
31. Hurwitz H, Fehrenbacher L, Novotny W, Cartwright T, Hainsworth J, Heim W, et al. Bevacizumab plus Irinotecan, Fluorouracil, and Leucovorin for Metastatic Colorectal Cancer. *New England Journal of Medicine.* 2004; 350(23):2335-2342.
32. Van Cutsem E, KÃ¶hne C-H, Hitre E, Zaluski J, Chang Chien C-R, Makhson A, et al. Cetuximab and Chemotherapy as Initial Treatment for Metastatic Colorectal Cancer. *New England Journal of Medicine.* 2009; 360(14):1408-1417.
33. Allegra C J, Jessup J M, Somerfield M R, Hamilton S R, Hammond E H, Hayes D F, et al. American Society of Clinical Oncology Provisional Clinical Opinion: Testing for KRAS Gene Mutations in Patients With Metastatic Colorectal Carcinoma to Predict Response to Antiâ€ "Epidermal Growth Factor Receptor Monoclonal Antibody Therapy. *Journal of Clinical Oncology.* 2009; 27(12):2091-2096.
34. Franklin M C, Carey K D, Vajdos F F, Leahy D J, de Vos A M, Sliwkowski M X. Insights into ErbB signaling from the structure of the ErbB2-pertuzumab complex. *Cancer Cell.* 2004; 5(4):317-328.
35. Agus D B, Akita R W, Fox W D, Lewis G D, Higgins B, Pisacane P I, et al. Targeting ligand-activated ErbB2 signaling inhibits breast and prostate tumor growth. *Cancer Cell.* 2002; 2(2):127-137.
36. http://clinicaltrials.gov/.
37. Stove C, Stove V, Derycke L, Van Marck V, Mareel M, Bracke M. The heregulin/human epidermal growth factor receptor as a new growth factor system in melanoma with multiple ways of deregulation. *J Invest Dermatol.* 2003; 121(4):802-812.
38. Falls D L. Neuregulins: functions, forms, and signaling strategies. *Exp Cell Res.* 2003; 284(1):14-30.
39. Wolpin B M, Mayer R J. Systemic Treatment of Colorectal Cancer. *Gastroenterology.* 2008; 134(5):1296-1310.e1291.
40. Koninckx R, Hensen K, Daniels A, Moreels M, Lambrichts I, Jongen H, et al. Human bone marrow stem cells co-cultured with neonatal rat cardiomyocytes display limited cardiomyogenic plasticity. *Cytotherapy.* 2009; 11(6):778-792.
41. Vermeulen S J, Bruyneel E A, Bracke M E, De Bruyne G K, Vennekens K M, Vleminckx K L, et al. Transition from the noninvasive to the invasive phenotype and loss of alpha-catenin in human colon cancer cells. *Cancer Res.* 1995; 55(20):4722-4728.
42. Maynard D M, Heijnen H F G, Horne M K, White J G, Gahl W A. Proteomic analysis of platelet α-granules using mass spectrometry. *J Thromb Haemost.* 2007; 5(9):1945-1955.
43. Perkins D N, Pappin D J C, Creasy D M, Cottrell J S. Probability-based protein identification by searching 44. Celis J E, Gromov P, Cabezón T, Moreira J M A, Ambartsumian N, Sandelin K, et al. Proteomic Characterization of the Interstitial Fluid Perfusing the Breast Tumor Microenvironment. *Mol Cell Proteomics*. 2004; 3(4):327-344.
45. De Wever O, Hendrix A, De Boeck A, Westbroek W, Braems G, Emami S, et al. Modeling and quantification of cancer cell invasion through collagen type I matrices. *Int J Dev Biol*. 2009.
46. Datta S R, Dudek H, Tao X, Masters S, Fu H, Gotoh Y, et al. Akt phosphorylation of BAD couples survival signals to the cell-intrinsic death machinery. *Cell*. 1997; 91(2):231-241.
47. Oltval Z N, Milliman C L, Korsmeyer S J. Bcl-2 heterodimerizes in vivo with a conserved homolog, Bax, that accelerates programmed cell death. *Cell*. 1993; 74(4):609-619.
48. Jones R B, Gordus A, Krall J A, MacBeath G. A quantitative protein interaction network for the ErbB receptors using protein microarrays. *Nature*. 2006; 439(7073):168-174.
49. Yarden Y, Sliwkowski M X. Untangling the ErbB signalling network. *Nat Rev Mol Cell Biol*. 2001; 2(2):127-137.
50. Shi F, Telesco S E, Liu Y, Radhakrishnan R, Lemmon M A. ErbB3/HER3 intracellular domain is competent to bind ATP and catalyze autophosphorylation. *Proc Natl Acad Sci USA*. 2010; 107(17):7692-7697.
51. Graus-Porta D, Beerli R R, Daly J M, Hynes N E. ErbB-2, the preferred heterodimerization partner of all ErbB receptors, is a mediator of lateral signaling. *EMBO J*. 1997; 16(7):1647-1655.
52. Badache A, Hynes N E. A new therapeutic antibody masks ErbB2 to its partners. *Cancer Cell*. 2004; 5(4):299-301.
53. Xia W, Liu L-H, Ho P, Spector N L. Truncated ErbB2 receptor (p95ErbB2) is regulated by heregulin through heterodimer formation with ErbB3 yet remains sensitive to the dual EGFR//ErbB2 kinase inhibitor GW572016. *Oncogene*. 2004; 23(3):646-653.
54. Moasser M M. The oncogene HER2: its signaling and transforming functions and its role in human cancer pathogenesis. *Oncogene*. 2007; 26(45):6469-6487.
55. Cho H-S, Mason K, Ramyar K X, Stanley A M, Gabelli S B, Denney D W, et al. Structure of the extracellular region of HER2 alone and in complex with the Herceptin Fab. *Nature*. 2003; 421(6924):756-760.
56. Harding J, Burtness B. Cetuximab: an epidermal growth factor receptor chemeric human-murine monoclonal antibody. *Drugs Today (Barc)*. 2005; 41(2):107-127.
57. Stove C, Bracke M. Roles for neuregulins in human cancer. *Clin Exp Metastasis*. 2004; 21(8):665-684.
58. Frenzel K E, Falls D L. Neuregulin-1 proteins in rat brain and transfected cells are localized to lipid rafts. *J Neurochem*. 2001; 77(1):1-12.
59. Burgess T L, Ross S L, Qian Y-x, Brankow D, Hu S. Biosynthetic Processing of neu Differentiation Factor. *J Biol Chem*. 1995; 270(32):19188-19196.
60. Lu H S, Hara S, Wong L W-I, Jones M D, Katta V, Trail G, et al. Post-translational Processing of Membrane-associated neu Differentiation Factor Proisoforms Expressed in Mammalian Cells. *J Biol Chem*. 1995; 270(9):4775-4783.
61. Dominici M, Blanc K L, Mueller I, Slaper-Cortenbach I, Marini F, Krause D, et al. Minimal criteria for defining multipotent mesenchymal stromal cells. The International Society for Cellular Therapy position statement. *Cytotherapy*. 2006; 8(4):315-317.

The invention claimed is:

1. A method for treating colorectal cancer in a subject comprising:
   measuring the level of transmembrane type 1 neuregulin-1 in tumor-associated mesenchymal cells present in a biological sample taken from said subject, and
   comparing said level of transmembrane type 1 neuregulin-1 with a reference level of transmembrane type 1 neuregulin-1 obtained from a sample of healthy tissue of a subject,
   wherein said tumor-associated mesenchymal cells are spindle-shaped, mesenchymal, non-cancer cells which are bone-marrow derived or recruited from other compartments and tissues within the human body and which are present around the cancer cells in a biological sample taken from said subject; and
   administering a treatment for colorectal cancer upon a determination that transmembrane type 1 neuregulin-1 in tumor-associated mesenchymal cells present in a sample from the subject is significantly increased as compared to that of said healthy tissue.

2. A method according to claim 1,
   wherein said method incorporates the decision whether or not a patient having colorectal cancer would benefit from a therapy based on the prevention of neuregulin-1 activity or the prevention of the tyrosine kinase activity of HER3, and wherein said significantly increased level of transmembrane type 1 neuregulin-1 in tumor-associated mesenchymal cells present in a sample of the patient as compared to that of said healthy tissue indicates that said patient would benefit from a therapy based on the prevention of neuregulin-1 activity or the prevention of the tyrosine kinase activity of HER3, or,
   wherein said method incorporates the decision or determination whether a patient having colorectal cancer has developed resistance to a therapy based on the prevention of HER1 activity, and wherein said significantly increased level of transmembrane type 1 neuregulin-1 in tumor-associated mesenchymal cells present in a sample of the patient as compared to that of said healthy tissue indicates that said patient has resistance to a therapy based on the prevention of the tyrosine kinase activity of HER 1.

3. A method according to claim 1 wherein said biological sample is colorectal cancer tissue taken from said subject.

4. A method according to claim 1 wherein said transmembrane type 1 neuregulin-1 is measured by immunohistochemistry on frozen samples.

5. A method according to claim 1 wherein said level of transmembrane type 1 neuregulin-1 is significantly increased when more than 25% of said tumor-associated mesenchymal cells within said sample contain transmembrane type 1 neuregulin-1 staining.

6. A method according to claim 1 wherein a worse prognosis corresponds to having a significantly increased chance to belong to the higher cancer stages according to the Union for International Cancer Control, and/or, to having a significantly increased chance to have an increased invasion depth of the tumor, and/or, to have a significantly increased chance to have a decreased progression-free survival.

7. A method according to claim 1, further comprising identifying tumor-associated mesenchymal cells in a biological sample from said subject.

8. A method according to claim 7, wherein the biological sample is stained using Mayer's hematoxylin solution.

* * * * *

SEQUENCE LISTING

```
<160> NUMBER OF SEQ ID NOS: 10

<210> SEQ ID NO 1
<211> LENGTH: 12
<212> TYPE: PRT
<213> ORGANISM: Homo sapiens

<400> SEQUENCE: 1

Ala Ser Leu Ala Asp Ser Gly Glu Tyr Met Cys Lys
1               5                   10

<210> SEQ ID NO 2
<211> LENGTH: 11
<212> TYPE: PRT
<213> ORGANISM: Homo sapiens

<400> SEQUENCE: 2

Cys Glu Thr Ser Ser Glu Tyr Ser Ser Leu Arg
1               5                   10

<210> SEQ ID NO 3
<211> LENGTH: 15
<212> TYPE: PRT
<213> ORGANISM: Homo sapiens

<400> SEQUENCE: 3

Leu Val Leu Arg Cys Glu Thr Ser Ser Glu Tyr Ser Ser Leu Arg
1               5                   10                  15
```

```
<210> SEQ ID NO 4
<211> LENGTH: 13
<212> TYPE: PRT
<213> ORGANISM: Homo sapiens

<400> SEQUENCE: 4

Thr Phe Cys Val Asn Gly Gly Glu Cys Phe Met Val Lys
1               5                   10

<210> SEQ ID NO 5
<211> LENGTH: 21
<212> TYPE: DNA
<213> ORGANISM: Artificial Sequence
<220> FEATURE:
<223> OTHER INFORMATION: siRNA targeting HER1

<400> SEQUENCE: 5
tacgaatatt aaacacttca a                                              21

<210> SEQ ID NO 6
<211> LENGTH: 21
<212> TYPE: DNA
<213> ORGANISM: Artificial Sequence
<220> FEATURE:
<223> OTHER INFORMATION: siRNA targeting HER1

<400> SEQUENCE: 6
ataggtattg gtgaatttaa a                                              21

<210> SEQ ID NO 7
<211> LENGTH: 21
<212> TYPE: DNA
<213> ORGANISM: Artificial Sequence
<220> FEATURE:
<223> OTHER INFORMATION: siRNA targeting HER2

<400> SEQUENCE: 7
cacgtttgag tccatgccca a                                              21

<210> SEQ ID NO 8
<211> LENGTH: 21
<212> TYPE: DNA
<213> ORGANISM: Artificial Sequence
<220> FEATURE:
<223> OTHER INFORMATION: siRNA targeting HER3

<400> SEQUENCE: 8
cttcgtcatg ttgaactata a                                              21

<210> SEQ ID NO 9
<211> LENGTH: 21
<212> TYPE: DNA
<213> ORGANISM: Artificial Sequence
<220> FEATURE:
<223> OTHER INFORMATION: siRNA targeting AKT

<400> SEQUENCE: 9
cacgcttggt cccgaggcca a                                              21

<210> SEQ ID NO 10
<211> LENGTH: 21
<212> TYPE: DNA
<213> ORGANISM: Artificial Sequence
<220> FEATURE:
<223> OTHER INFORMATION: siRNA targeting NRG-1
```

```
<400> SEQUENCE: 10
tcggctgcag gttccaaact a                                            21
```